(12) United States Patent
Brown et al.

(10) Patent No.: US 11,572,562 B2
(45) Date of Patent: Feb. 7, 2023

(54) COMPOSITIONS AND METHODS FOR INHIBITING GYS2 EXPRESSION

(71) Applicant: Dicerna Pharmaceuticals, Inc., Lexington, MA (US)

(72) Inventors: Bob D. Brown, Littleton, MA (US); Natalie Pursell, Lexington, MA (US); Henryk T. Dudek, Belmont, MA (US); Cheng Lai, Lexington, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 16/977,152

(22) PCT Filed: Feb. 15, 2019

(86) PCT No.: PCT/US2019/018189
§ 371 (c)(1),
(2) Date: Sep. 1, 2020

(87) PCT Pub. No.: WO2019/168687
PCT Pub. Date: Sep. 6, 2019

(65) Prior Publication Data
US 2021/0062197 A1 Mar. 4, 2021

Related U.S. Application Data

(60) Provisional application No. 62/637,574, filed on Mar. 2, 2018.

(51) Int. Cl.
*C12N 15/113* (2010.01)
*A61K 31/7088* (2006.01)

(52) U.S. Cl.
CPC ...... *C12N 15/1137* (2013.01); *A61K 31/7088* (2013.01); *C12N 2310/14* (2013.01); *C12N 2310/3519* (2013.01); *C12N 2310/533* (2013.01); *C12N 2320/11* (2013.01); *C12Y 204/01011* (2013.01)

(58) Field of Classification Search
None
See application file for complete search history.

(56) References Cited

U.S. PATENT DOCUMENTS

| | | | |
|---|---|---|---|
| 2003/0004122 A1 | 1/2003 | Beigelman et al. | |
| 2005/0255487 A1* | 11/2005 | Khvorova | A61P 37/02 435/6.11 |
| 2006/0078902 A1* | 4/2006 | Bunting | C12N 15/111 435/6.11 |
| 2008/0113351 A1 | 5/2008 | Naito et al. | |
| 2011/0105591 A1* | 5/2011 | Feinstein | A61P 35/00 514/44 A |
| 2021/0115438 A1* | 4/2021 | Bleicher | C07H 19/16 |

FOREIGN PATENT DOCUMENTS

| | | | |
|---|---|---|---|
| WO | WO-2005001092 A2 * | 1/2005 | ........... C07K 14/705 |
| WO | WO-2010105372 A1 | 9/2010 | |
| WO | WO-2016100401 A1 | 6/2016 | |
| WO | WO-2017141109 A1 | 8/2017 | |
| WO | WO-2019168687 A1 | 9/2019 | |

OTHER PUBLICATIONS

Pursell et al. Molecular Therapy vol. Jul. 26, 2018, pp. 1771-1782 (Year: 2018).*
Gusarov et al., "Glycogen controls Caenorhabditis elegans lifespan and resistance to oxidative stress," Nat Commun. 8:15868 (2017).
International Search Report and Written Opinion issued by the United States Patent and Trademark Office as International Searching Authority for International Application No. PCT/US2019/018189, dated Jul. 17, 2019 (13 pages).
Dicerna Pharmaceuticals, Inc., "Taking RNAi under the skin," Nature.com. 2016:B12; Retrieved from the Internet: https://media.nature.com/original/magazine-assets/d43747-020-00189-y/d43747-020-00189-y.pdf.
Huang, "Preclinical and Clinical Advances of GalNAc-Decorated Nucleic Acid Therapeutics," Mol Ther Nucleic Acids. 2017;6:116-132.

* cited by examiner

*Primary Examiner* — Brian Whiteman
(74) *Attorney, Agent, or Firm* — Dechert LLP; Andrea L. C. Reid; Gang Wang

(57) ABSTRACT

This disclosure relates to oligonucleotides, compositions and methods useful for reducing GYS2 expression, particularly in hepatocytes. Disclosed oligonucleotides for the reduction of GYS2 expression may be double-stranded or single-stranded, and may be modified for improved characteristics such as stronger resistance to nucleases and lower immunogenicity. Disclosed oligonucleotides for the reduction of GYS2 expression may also include targeting ligands to target a particular cell or organ, such as the hepatocytes of the liver, and may be used to treat glycogen storage diseases (e.g., GSDIa, GSDIII, GSDIV, GSDVI, and GSDIX) and related conditions.

35 Claims, 14 Drawing Sheets
Specification includes a Sequence Listing.

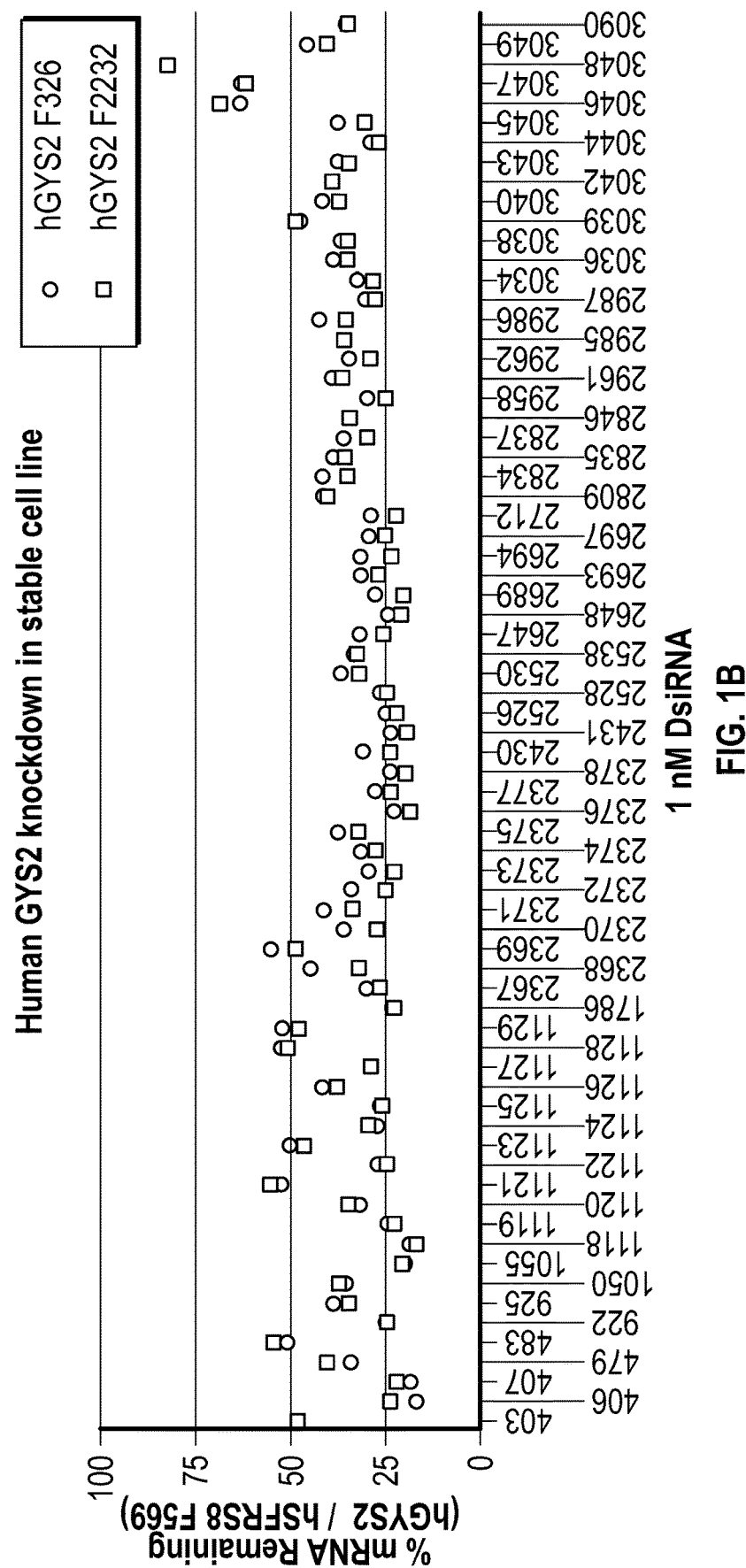

SEQUENCE LISTING

<160> NUMBER OF SEQ ID NOS: 627

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1
caggugcauu uggaagaug gcuga                                          25

<210> SEQ ID NO 2
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 2
aggugcauuu uggaagaugg cugat                                         25

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 3
ggugcauuuu ggaagauggc ugata                                         25

<210> SEQ ID NO 4
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 4
gugcauuuug gaagauggcu gauag                                         25

<210> SEQ ID NO 5
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 5
ugcauuuugg aagauggcug auaga                                         25

<210> SEQ ID NO 6
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 6
aaggaagucc uuauguggua cuutt                                         25

<210> SEQ ID NO 7
<211> LENGTH: 25
<212> TYPE: RNA
<213> ORGANISM: Artificial Sequence

```
<220> FEATURE:
<223> OTHER INFORMATION: Synthetic Polynucleotide

<400> SEQUENCE: 7
gaaguccuua ugugguacuu uuuga                                        25

<210> SEQ ID NO 8
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 8
aaguccuuau gugguacuuu uugac                                        25

<210> SEQ ID NO 9
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 9
aguccuuaug ugguacuuuu ugaca                                        25

<210> SEQ ID NO 10
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 10
guccuuaugu gguacuuuuu gacat                                        25

<210> SEQ ID NO 11
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 11
ccuuaugugg uacuuuuuga cauag                                        25

<210> SEQ ID NO 12
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 12
guacuuuuug acauaggcua uucag                                        25

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 13
cgagaagcca augauaugcu gauat                                        25
```

```
<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 14
gagaagccaa ugauaugcug auatt                                              25

<210> SEQ ID NO 15
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 15
agaagccaau gauaugcuga uautt                                              25

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 16
gaagccaaug auaugcugau auutg                                              25

<210> SEQ ID NO 17
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 17
agccaaugau augcugauau uugga                                              25

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 18
gccaaugaua ugcugauauu uggat                                              25

<210> SEQ ID NO 19
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 19
ccaaugauau gcugauauuu ggatc                                              25

<210> SEQ ID NO 20
<211> LENGTH: 25
<212> TYPE: DNA
<213> ORGANISM: Artificial Sequence
<220> FEATURE:
<223> OTHER INFORMATION: Synthetic Polynucleotide
```

```
<400> SEQUENCE: 20
aaugauaugc ugauauuugg auctt                                      25

<210> SEQ ID NO 21
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 21
augauaugcu gauauuugga ucutt                                      25

<210> SEQ ID NO 22
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 22
ugauaugcug auauuuggau cuuta                                      25

<210> SEQ ID NO 23
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 23
auaugcugau auuggaucu uuaac                                       25

<210> SEQ ID NO 24
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 24
augcugauau uuggaucuuu aactg                                      25

<210> SEQ ID NO 25
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 25
ucuuuaacug ccugguucuu aaaag                                      25

<210> SEQ ID NO 26
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 26
cuuuaacugc cugguucuua aaaga                                      25

<210> SEQ ID NO 27
```

```
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 27
uuuaacugcc ugguucuuaa aagag                                25

<210> SEQ ID NO 28
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 28
uuaacugccu gguucuuaaa agagg                                25

<210> SEQ ID NO 29
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 29
uaacugccug guucuuaaaa gaggt                                25

<210> SEQ ID NO 30
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 30
uugcccaauu ccaugaaugg caggc                                25

<210> SEQ ID NO 31
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 31
ugcccaauuc caugaauggc aggct                                25

<210> SEQ ID NO 32
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 32
gcccaauucc augaauggca ggctg                                25

<210> SEQ ID NO 33
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 33
```

```
cccaauucca ugaauggcag gcugg                                          25

<210> SEQ ID NO 34
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 34
ccaauuccau gaauggcagg cugga                                          25

<210> SEQ ID NO 35
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 35 caauccaug aauggcaggc uggaa                                           25

<210> SEQ ID NO 36
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 36
aauuccauga auggcaggcu ggaat                                          25

<210> SEQ ID NO 37
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 37
auuccaugaa uggcaggcug gaatt                                          25

<210> SEQ ID NO 38
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 38
uuccaugaau ggcaggcugg aautg                                          25

<210> SEQ ID NO 39
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 39
uccaugaaug gcaggcugga auugg                                          25

<210> SEQ ID NO 40
<211> LENGTH: 25
<212> TYPE: DNA
```

```
<213> ORGANISM: Artificial Sequence
<220> FEATURE:
<223> OTHER INFORMATION: Synthetic Polynucleotide

<400> SEQUENCE: 40
ggaaacuucc uauugccaca auauu                                              25

<210> SEQ ID NO 41
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 41
gguaucucug ugcagcaaau auuga                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 42
guaucucugu gcagcaaaua uugat                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 43
uaucucugug cagcaaauau ugatt                                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 44
aucucugugc agcaaauauu gauuu                                              25

<210> SEQ ID NO 45
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 45
ucucugugca gcaaauauug auutc                                              25

<210> SEQ ID NO 46
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 46
cucugugcag caaauauuga uuuct                                              25
```

<210> SEQ ID NO 47
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 47
ucugugcagc aaauauugau uucta                                    25

<210> SEQ ID NO 48
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 48
cugugcagca aauauugauu ucuac                                    25

<210> SEQ ID NO 49
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 49
ugugcagcaa auauugauuu cuaca                                    25

<210> SEQ ID NO 50
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 50
gugcagcaaa uauugauuuc uacaa                                    25

<210> SEQ ID NO 51
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 51
ugcagcaaau auugauuucu acaac                                    25

<210> SEQ ID NO 52
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 52
gcagcaaaua uugauuucua caacc                                    25

<210> SEQ ID NO 53
<211> LENGTH: 25
<212> TYPE: RNA
<213> ORGANISM: Artificial Sequence
<220> FEATURE:

<223> OTHER INFORMATION: Synthetic Polynucleotide

<400> SEQUENCE: 53
cagcaaauau ugauuucuac aacca                                    25

<210> SEQ ID NO 54
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 54
agcaaauauu gauuucuaca accat                                    25

<210> SEQ ID NO 55
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 55
gcaaauauug auuucuacaa ccatc                                    25

<210> SEQ ID NO 56
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 56
auauugauuu cuacaaccau cuuga                                    25

<210> SEQ ID NO 57
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 57
uugauuucua caaccaucuu gauaa                                    25

<210> SEQ ID NO 58
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 58
gauuucuaca accaucuuga uaagt                                    25

<210> SEQ ID NO 59
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 59
auuucuacaa ccaucuugau aagtt                                    25

```
<210> SEQ ID NO 60
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 60
uucuacaacc aucuugauaa guuta                                          25

<210> SEQ ID NO 61
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 61
cuacaaccau cuugauaagu uuaac                                          25

<210> SEQ ID NO 62
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 62
uacaaccauc uugauaaguu uaaca                                          25

<210> SEQ ID NO 63
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 63
acaaccaucu ugauaaguuu aacat                                          25

<210> SEQ ID NO 64
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 64
caaccaucuu gauaaguuua acatt                                          25

<210> SEQ ID NO 65
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 65
aaccaucuug auaaguuuaa caug                                           25

<210> SEQ ID NO 66
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 66
accaucuuga uaaguuuaac auuga                                  25

<210> SEQ ID NO 67
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 67
ccaucuugau aaguuuaaca uugac                                  25

<210> SEQ ID NO 68
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 68
caucuugaua aguuuaacau ugaca                                  25

<210> SEQ ID NO 69
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 69
aucuugauaa guuuaacauu gacaa                                  25

<210> SEQ ID NO 70
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 70
guucaccacg guuucugaaa uaaca                                  25

<210> SEQ ID NO 71
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 71
caccacgguu ucugaaauaa cagca                                  25

<210> SEQ ID NO 72
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 72
ccacgguuuc ugaaauaaca gcaat                                  25

<210> SEQ ID NO 73
<211> LENGTH: 25
```

```
<212> TYPE: DNA
<213> ORGANISM: Artificial Sequence
<220> FEATURE:
<223> OTHER INFORMATION: Synthetic Polynucleotide

<400> SEQUENCE: 73
cacgguuucu gaaauaacag caata                                              25

<210> SEQ ID NO 74
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 74
cgguuucuga auaacagca auaga                                               25

<210> SEQ ID NO 75
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 75
gguuucugaa auaacagcaa uagaa                                              25

<210> SEQ ID NO 76
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 76
guuucugaaa uaacagcaau agaag                                              25

<210> SEQ ID NO 77
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 77
cugaaauaac agcaauagaa gcuga                                              25

<210> SEQ ID NO 78
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 78
aagagaaagc cugauguagu uacuc                                              25

<210> SEQ ID NO 79
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 79
```
agagaaagcc ugauguaguu acucc                                          25

<210> SEQ ID NO 80
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 80
ggcuugaaug uuaagaaauu uucag                                          25

<210> SEQ ID NO 81
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 81
gcuugaaugu uaagaaauuu ucagc                                          25

<210> SEQ ID NO 82
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 82
cuugaauguu aagaaauuuu cagca                                          25

<210> SEQ ID NO 83
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 83
uugaauguua agaaauuuuc agcag                                          25

<210> SEQ ID NO 84
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 84
ugaauguuaa gaaauuuuca gcagt                                          25

<210> SEQ ID NO 85
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 85
gaauguuaag aaauuuucag cagtg                                          25

<210> SEQ ID NO 86
<211> LENGTH: 25
<212> TYPE: RNA
<213> ORGANISM: Artificial Sequence

```
<220> FEATURE:
<223> OTHER INFORMATION: Synthetic Polynucleotide

<400> SEQUENCE: 86
auguuaagaa auuucagca gugca                                         25

<210> SEQ ID NO 87
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 87 agaaauuuc agcagugcau gagtt                                         25

<210> SEQ ID NO 88
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 88
agcagugcau gaguuucaaa aucta                                        25

<210> SEQ ID NO 89
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 89
agauuuuguu cgaggucauu ucuat                                        25

<210> SEQ ID NO 90
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 90
guucgagguc auuucuaugg ucatc                                        25

<210> SEQ ID NO 91
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 91
uucgagguca uuucuauggu cauct                                        25

<210> SEQ ID NO 92
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 92
ucgaggucau uucuaugguc auctc                                        25
```

```
<210> SEQ ID NO 93
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 93
cgaggucauu ucuaugguca ucucg                                           25

<210> SEQ ID NO 94
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 94
gaggucauuu cuaugucau cucga                                            25

<210> SEQ ID NO 95
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 95
aggucauuuc uauggucauc ucgac                                           25

<210> SEQ ID NO 96
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 96
ggucauuucu auggucaucu cgact                                           25

<210> SEQ ID NO 97
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 97
gucauuucua uggucaucuc gactt                                           25

<210> SEQ ID NO 98
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 98
ugaaaagacu uuguuccuuu ucatt                                           25

<210> SEQ ID NO 99
<211> LENGTH: 25
<212> TYPE: DNA
<213> ORGANISM: Artificial Sequence
<220> FEATURE:
<223> OTHER INFORMATION: Synthetic Polynucleotide
```

<400> SEQUENCE: 99
gaaaagacuu uguuccuuuu caug                                    25

<210> SEQ ID NO 100
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 100
aaagacuuug uuccuuuuca uugct                                   25

<210> SEQ ID NO 101
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 101
cugaggaugc auaaaaguga cauca                                   25

<210> SEQ ID NO 102
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 102
gaggaugcau aaaagugaca ucaca                                   25

<210> SEQ ID NO 103
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 103
uuuuucauua ugccugccaa gacaa                                   25

<210> SEQ ID NO 104
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 104
ucauuaugcc ugccaagaca aauaa                                   25

<210> SEQ ID NO 105
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 105
cauuaugccu gccaagacaa auaat                                   25

<210> SEQ ID NO 106

```
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 106
auuaugccug ccaagacaaa uaatt                                    25

<210> SEQ ID NO 107
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 107
augccugcca agacaaauaa uuuca                                    25

<210> SEQ ID NO 108
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 108
aauuucaacg uggaacccu gaaag                                     25

<210> SEQ ID NO 109
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 109
auuucaacgu ggaacccug aaagg                                     25

<210> SEQ ID NO 110
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 110
uuucaacgug gaacccuga aagga                                     25

<210> SEQ ID NO 111
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 111
uucaacgugg aacccugaa aggac                                     25

<210> SEQ ID NO 112
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 112
```
ucaacgugga aacccugaaa ggaca                                              25

<210> SEQ ID NO 113
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 113
uugcacauuc ugugaaggaa aagtt                                              25

<210> SEQ ID NO 114
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 114
ugcacauucu gugaaggaaa agutt                                              25

<210> SEQ ID NO 115
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 115
gcacauucug ugaaggaaaa guutg                                              25

<210> SEQ ID NO 116
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 116
auucugugaa ggaaaaguuu ggaaa                                              25

<210> SEQ ID NO 117
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 117
gugaaggaaa aguuuggaaa aaaac                                              25

<210> SEQ ID NO 118
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 118
gaaaaaaacu cuaugaugca uuatt                                              25

<210> SEQ ID NO 119
<211> LENGTH: 25
<212> TYPE: DNA

```
<213> ORGANISM: Artificial Sequence
<220> FEATURE:
<223> OTHER INFORMATION: Synthetic Polynucleotide

<400> SEQUENCE: 119
aaaaaaacuc uaugaugcau uauta                                            25

<210> SEQ ID NO 120
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 120
aaaaaacucu augaugcauu auuaa                                            25

<210> SEQ ID NO 121
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 121
aaaaacucua ugaugcauua uuaag                                            25

<210> SEQ ID NO 122
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 122
uuauuaagag gagaaauucc ugacc                                            25

<210> SEQ ID NO 123
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 123
uauuaagagg agaaauuccu gacct                                            25

<210> SEQ ID NO 124
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 124
auuaagagga gaaauuccug acctg                                            25

<210> SEQ ID NO 125
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 125
uuaagaggag aaauuccuga ccuga                                            25
```

<210> SEQ ID NO 126
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 126
uaagaggaga aauuccugac cugaa                                          25

<210> SEQ ID NO 127
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 127
aagaggagaa auuccugacc ugaac                                          25

<210> SEQ ID NO 128
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 128
cgagaugauc uaacaauuau gaaaa                                          25

<210> SEQ ID NO 129
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 129
agaugaucua acaauuauga aaaga                                          25

<210> SEQ ID NO 130
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 130
gaugaucuaa caauuaugaa aagag                                          25

<210> SEQ ID NO 131
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 131
augaucuaac aauuaugaaa agagc                                          25

<210> SEQ ID NO 132
<211> LENGTH: 25
<212> TYPE: DNA
<213> ORGANISM: Artificial Sequence
<220> FEATURE:

```
<223> OTHER INFORMATION: Synthetic Polynucleotide

<400> SEQUENCE: 132
acaauuauga aaagagccau cuutt                                     25

<210> SEQ ID NO 133
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 133
gaaaagagcc aucuuucaa cucag                                      25

<210> SEQ ID NO 134
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 134
cccauccuca gcaccauuag acgga                                     25

<210> SEQ ID NO 135
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 135
ccauccucag caccauuaga cggat                                     25

<210> SEQ ID NO 136
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 136
cauccucagc accauuagac ggatt                                     25

<210> SEQ ID NO 137
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 137
auccucagca ccauuagacg gautg                                     25

<210> SEQ ID NO 138
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 138
uccucagcac cauuagacgg auugg                                     25
```

```
<210> SEQ ID NO 139
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 139
cccauggacu augaagaguu uguta                                              25

<210> SEQ ID NO 140
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 140
ccauggacua ugaagaguuu guuag                                              25

<210> SEQ ID NO 141
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 141
cuuggaguau uuccaucaua cuatg                                              25

<210> SEQ ID NO 142
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 142
uggaguauuu ccaucauacu augaa                                              25

<210> SEQ ID NO 143
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 143
ggaguauuuc caucauacua ugaac                                              25

<210> SEQ ID NO 144
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 144
gaguauuucc aucauacuau gaacc                                              25

<210> SEQ ID NO 145
<211> LENGTH: 25
<212> TYPE: DNA
<213> ORGANISM: Artificial Sequence
<220> FEATURE:
<223> OTHER INFORMATION: Synthetic Polynucleotide
```

<400> SEQUENCE: 145
uauuuccauc auacuaugaa ccctg    25

<210> SEQ ID NO 146
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 146
auacuccagc ugaaugcacu gugat    25

<210> SEQ ID NO 147
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 147
ggcagauauu accagcaugc cagac    25

<210> SEQ ID NO 148
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 148
gcagauauua ccagcaugcc agaca    25

<210> SEQ ID NO 149
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 149
cagauauuac cagcaugcca gacac    25

<210> SEQ ID NO 150
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 150
agauauuacc agcaugccag acacc    25

<210> SEQ ID NO 151
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 151
gauauuacca gcaugccaga cacct    25

<210> SEQ ID NO 152
<211> LENGTH: 25

```
<212> TYPE: DNA
<213> ORGANISM: Artificial Sequence
<220> FEATURE:
<223> OTHER INFORMATION: Synthetic Polynucleotide

<400> SEQUENCE: 152
auauuaccag caugccagac acctg                                          25

<210> SEQ ID NO 153
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 153
uauuaccagc augccagaca ccuga                                          25

<210> SEQ ID NO 154
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 154
auuaccagca ugccagacac cugac                                          25

<210> SEQ ID NO 155
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 155
uuaccagcau gccagacacc ugaca                                          25

<210> SEQ ID NO 156
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 156
uaccagcaug ccagacaccu gacat                                          25

<210> SEQ ID NO 157
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 157
accagcaugc cagacaccug acatt                                          25

<210> SEQ ID NO 158
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 158
```
ccagcaugcc agacaccuga cauta                                          25

<210> SEQ ID NO 159
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 159
cagcaugcca gacaccugac auuaa                                          25

<210> SEQ ID NO 160
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 160
agcaugccag acaccugaca uuaag                                          25

<210> SEQ ID NO 161
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 161
gcaugccaga caccugacau uaagc                                          25

<210> SEQ ID NO 162
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 162
ugccagacac cugacauuaa gcaga                                          25

<210> SEQ ID NO 163
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 163
ccugacauua agcagagcuu uucca                                          25

<210> SEQ ID NO 164
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 164
aagcagagcu uuccagaua aautc                                           25

<210> SEQ ID NO 165
<211> LENGTH: 25
<212> TYPE: RNA
<213> ORGANISM: Artificial Sequence

```
<220> FEATURE:
<223> OTHER INFORMATION: Synthetic Polynucleotide

<400> SEQUENCE: 165
gcagagcuuu uccagauaaa uucca                                          25

<210> SEQ ID NO 166
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 166
ccagauaaau uccaugugga acuaa                                          25

<210> SEQ ID NO 167
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 167
cagauaaauu ccauguggaa cuaac                                          25

<210> SEQ ID NO 168
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 168
uccucaguac caccuucucc uucag                                          25

<210> SEQ ID NO 169
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 169
ccucaguacc accuucuccu ucagg                                          25

<210> SEQ ID NO 170
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 170
gaaagggauc gguuaaauau caagt                                          25

<210> SEQ ID NO 171
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 171
agggaucggu uaaauaucaa gucac                                          25
```

<210> SEQ ID NO 172
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 172
aucgguuaaa uaucaaguca ccatt                                          25

<210> SEQ ID NO 173
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 173
gguuaaauau caagucacca uuutc                                          25

<210> SEQ ID NO 174
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 174
guuaaauauc aagucaccau uuuca                                          25

<210> SEQ ID NO 175
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 175
aaauaucaag ucaccauuuu cactg                                          25

<210> SEQ ID NO 176
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 176
aagaaaaagc ugcaugguga auata                                          25

<210> SEQ ID NO 177
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 177
agaaaaagcu gcauggugaa uauaa                                          25

<210> SEQ ID NO 178
<211> LENGTH: 25
<212> TYPE: RNA
<213> ORGANISM: Artificial Sequence
<220> FEATURE:
<223> OTHER INFORMATION: Synthetic Polynucleotide

```
<400> SEQUENCE: 178
aaaaagcugc auggugaaua uaaga                                 25

<210> SEQ ID NO 179
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 179
aaaagcugca uggugaauau aagaa                                 25

<210> SEQ ID NO 180
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 180
aagcugcaug gugaauauaa gaact                                 25

<210> SEQ ID NO 181
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 181
gcugcauggu gaauauaaga acuga                                 25

<210> SEQ ID NO 182
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 182
cugcauggug aauauaagaa cugaa                                 25

<210> SEQ ID NO 183
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 183
gcauggugaa uauaagaacu gaatt                                 25

<210> SEQ ID NO 184
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 184
cauggugaau auaagaacug aautc                                 25

<210> SEQ ID NO 185
```

```
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 185
auggugaaua uaagaacuga auuct                                              25

<210> SEQ ID NO 186
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 186
uggugaauau aagaacugaa uucta                                              25

<210> SEQ ID NO 187
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 187
ggugaauaua agaacugaau ucuac                                              25

<210> SEQ ID NO 188
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 188
gugaauauaa gaacugaauu cuaca                                              25

<210> SEQ ID NO 189
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 189
aauauaagaa cugaauucua caugt                                              25

<210> SEQ ID NO 190
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 190
auauaagaac ugaauucuac augtg                                              25

<210> SEQ ID NO 191
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 191
```

```
auaagaacug aauucuacau gugct                                           25

<210> SEQ ID NO 192
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 192
aagaacugaa uucuacaugu gcugc                                           25

<210> SEQ ID NO 193
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 193
ucagccaucu uccaaaaugc accggc                                          27

<210> SEQ ID NO 194
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 194
aucagccauc uuccaaaaug caccugg                                         27

<210> SEQ ID NO 195
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 195
uaucagccau cuuccaaaau gcaccug                                         27

<210> SEQ ID NO 196
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 196
cuaucagcca ucuuccaaaa ugcaccu                                         27

<210> SEQ ID NO 197
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 197
ucuaucagcc aucuuccaaa augcacc                                         27

<210> SEQ ID NO 198
<211> LENGTH: 27
<212> TYPE: RNA
```

```
<213> ORGANISM: Artificial Sequence
<220> FEATURE:
<223> OTHER INFORMATION: Synthetic Polynucleotide

<400> SEQUENCE: 198
aaaaguacca cauaaggacu uccuucu                                              27

<210> SEQ ID NO 199
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 199 ucaaaagua ccacauaagg acuuccu                                               27

<210> SEQ ID NO 200
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 200 gucaaaagu accacauaag gacuucc                                               27

<210> SEQ ID NO 201
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 201
ugucaaaaag uaccacauaa ggacuuc                                              27

<210> SEQ ID NO 202
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 202
augucaaaaa guaccacaua aggacuu                                              27

<210> SEQ ID NO 203
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 203
cuaugucaaa aaguaccaca uaaggac                                              27

<210> SEQ ID NO 204
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 204
cugaauagcc uaugucaaaa aguacca                                              27
```

<210> SEQ ID NO 205
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 205
auaucagcau aucauuggcu ucucggu                                27

<210> SEQ ID NO 206
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 206
aauaucagca uaucauuggc uucucgg                                27

<210> SEQ ID NO 207
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 207
aaauaucagc auaucauugg cuucucg                                27

<210> SEQ ID NO 208
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 208
caaauaucag cauaucauug gcuucuc                                27

<210> SEQ ID NO 209
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 209
uccaaauauc agcauaucau uggcuuc                                27

<210> SEQ ID NO 210
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 210
auccaaauau cagcauauca uuggcuu                                27

<210> SEQ ID NO 211
<211> LENGTH: 27
<212> TYPE: RNA
<213> ORGANISM: Artificial Sequence
<220> FEATURE:

<223> OTHER INFORMATION: Synthetic Polynucleotide

<400> SEQUENCE: 211
gauccaaaua ucagcauauc auuggcu                               27

<210> SEQ ID NO 212
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 212
aagauccaaa uaucagcaua ucauugg                               27

<210> SEQ ID NO 213
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 213
aaagauccaa auaucagcau aucauug                               27

<210> SEQ ID NO 214
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 214
uaaagaucca aauaucagca uaucauu                               27

<210> SEQ ID NO 215
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 215
guuaaagauc caaauaucag cauauca                               27

<210> SEQ ID NO 216
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 216
caguuaaaga uccaaauauc agcauau                               27

<210> SEQ ID NO 217
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 217
cuuuuaagaa ccaggcaguu aaagauc                               27

<210> SEQ ID NO 218
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 218
ucuuuuaaga accaggcagu uaaagau                                                27

<210> SEQ ID NO 219
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 219
cucuuuuaag aaccaggcag uuaaaga                                                27

<210> SEQ ID NO 220
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 220
ccucuuuuaa gaaccaggca guuaaag                                                27

<210> SEQ ID NO 221
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 221
accucuuuua agaaccaggc aguuaaa                                                27

<210> SEQ ID NO 222
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 222
gccugccauu cauggaauug ggcaacg                                                27

<210> SEQ ID NO 223
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 223
agccugccau ucauggaauu gggcaac                                                27

<210> SEQ ID NO 224
<211> LENGTH: 27
<212> TYPE: RNA
<213> ORGANISM: Artificial Sequence
<220> FEATURE:
<223> OTHER INFORMATION: Synthetic Polynucleotide

```
<400> SEQUENCE: 224
cagccugcca uucauggaau ugggcaa                                    27

<210> SEQ ID NO 225
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 225
ccagccugcc auucauggaa uugggca                                    27

<210> SEQ ID NO 226
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 226
uccagccugc cauucaugga auugggc                                    27

<210> SEQ ID NO 227
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 227
uuccagccug ccauucaugg aauuggg                                    27

<210> SEQ ID NO 228
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 228
auuccagccu gccauucaug gaauugg                                    27

<210> SEQ ID NO 229
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 229
aauuccagcc ugccauucau ggaauug                                    27

<210> SEQ ID NO 230
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 230
caauuccagc cugccauuca uggaauu                                    27

<210> SEQ ID NO 231
<211> LENGTH: 27
```

```
<212> TYPE: RNA
<213> ORGANISM: Artificial Sequence
<220> FEATURE:
<223> OTHER INFORMATION: Synthetic Polynucleotide

<400> SEQUENCE: 231
ccaauuccag ccugccauuc auggaau                                              27

<210> SEQ ID NO 232
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 232
aauauugugg caauaggaag uuuccug                                              27

<210> SEQ ID NO 233
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 233
ucaauauuug cugcacagag auaccuc                                              27

<210> SEQ ID NO 234
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 234
aucaauauuu gcugcacaga gauaccu                                              27

<210> SEQ ID NO 235
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 235
aaucaauauu ugcugcacag agauacc                                              27

<210> SEQ ID NO 236
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 236
aaaucaauau uugcugcaca gagauac                                              27

<210> SEQ ID NO 237
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 237
```
gaaaucaaua uuugcugcac agagaua						27

<210> SEQ ID NO 238
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 238
agaaaucaau auuugcugca cagagau						27

<210> SEQ ID NO 239
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 239
uagaaaucaa uauuugcugc acagaga						27

<210> SEQ ID NO 240
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 240
guagaaauca auauuugcug cacagag						27

<210> SEQ ID NO 241
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 241
uguagaaauc aauauuugcu gcacaga						27

<210> SEQ ID NO 242
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 242
uuguagaaau caauauuugc ugcacag						27

<210> SEQ ID NO 243
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 243
guuguagaaa ucaauauuug cugcaca						27

<210> SEQ ID NO 244
<211> LENGTH: 27
<212> TYPE: RNA
<213> ORGANISM: Artificial Sequence

```
<220> FEATURE:
<223> OTHER INFORMATION: Synthetic Polynucleotide

<400> SEQUENCE: 244
gguuguagaa aucaauauuu gcugcac                                               27

<210> SEQ ID NO 245
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 245
ugguuguaga aaucaauauu ugcugca                                               27

<210> SEQ ID NO 246
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 246
augguuguag aaaucaauau uugcugc                                               27

<210> SEQ ID NO 247
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 247
gaugguugua gaaaucaaua uuugcug                                               27

<210> SEQ ID NO 248
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 248
ucaagauggu uguagaaauc aauauuu                                               27

<210> SEQ ID NO 249
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 249
uuaucaagau gguuguagaa aucaaua                                               27

<210> SEQ ID NO 250
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 250
acuuaucaag augguuguag aaaucaa                                               27
```

<210> SEQ ID NO 251
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 251
aacuuaucaa gaugguugua gaaauca                                              27

<210> SEQ ID NO 252
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 252
uaaacuuauc aagaugguug uagaaau                                              27

<210> SEQ ID NO 253
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 253
guuaaacuua ucaagauggu uguagaa                                              27

<210> SEQ ID NO 254
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 254
uguuaaacuu aucaagaugg uuguaga                                              27

<210> SEQ ID NO 255
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 255
auguuaaacu uaucaagaug guuguag                                              27

<210> SEQ ID NO 256
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 256
aauguuaaac uuaucaagau gguugua                                              27

<210> SEQ ID NO 257
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 257
caauguuaaa cuuaucaaga ugguugu                                    27

<210> SEQ ID NO 258
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 258
ucaauguuaa acuuaucaag augguug                                    27

<210> SEQ ID NO 259
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 259
gucaauguua aacuuaucaa gaugguu                                    27

<210> SEQ ID NO 260
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 260
ugucaauguu aaacuuauca agauggu                                    27

<210> SEQ ID NO 261
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 261
uugucaaugu uaaacuuauc aagaugg                                    27

<210> SEQ ID NO 262
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 262
uguuauuuca gaaaccgugg ugaacac                                    27

<210> SEQ ID NO 263
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 263
ugcuguuauu ucagaaaccg uggugaa                                    27

<210> SEQ ID NO 264

```
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 264
auugcuguua uuucagaaac cguggug                                            27

<210> SEQ ID NO 265
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 265
uauugcuguu auuucagaaa ccguggu                                            27

<210> SEQ ID NO 266
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 266
ucuauugcug uuauuucaga aaccgug                                            27

<210> SEQ ID NO 267
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 267
uucuauugcu guuauuucag aaaccgu                                            27

<210> SEQ ID NO 268
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 268
cuucuauugc uguuauuuca gaaaccg                                            27

<210> SEQ ID NO 269
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 269
ucagcuucua uugcuguuau uucagaa                                            27

<210> SEQ ID NO 270
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 270
```
gaguaacuac aucaggcuuu cucuuca        27

<210> SEQ ID NO 271
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 271
ggaguaacua caucaggcuu ucucuuc        27

<210> SEQ ID NO 272
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 272
cugaaaauuu cuuaacauuc aagccgu        27

<210> SEQ ID NO 273
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 273
gcugaaaauu ucuuaacauu caagccg        27

<210> SEQ ID NO 274
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 274
ugcugaaaau uucuuaacau ucaagcc        27

<210> SEQ ID NO 275
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 275
cugcugaaaa uuucuuaaca uucaagc        27

<210> SEQ ID NO 276
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 276
acugcugaaa auucuuaac auucaag        27

<210> SEQ ID NO 277
<211> LENGTH: 27
<212> TYPE: RNA

-continued

```
<213> ORGANISM: Artificial Sequence
<220> FEATURE:
<223> OTHER INFORMATION: Synthetic Polynucleotide

<400> SEQUENCE: 277
cacugcugaa aauuucuuaa cauucaa                                          27

<210> SEQ ID NO 278
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 278
ugcacugcug aaaauuucuu aacauuc                                          27

<210> SEQ ID NO 279
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 279
aacucaugca cugcugaaaa uuucuua                                          27

<210> SEQ ID NO 280
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 280
uagauuuuga aacucaugca cugcuga                                          27

<210> SEQ ID NO 281
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 281
auagaaauga ccucgaacaa aaucuug                                          27

<210> SEQ ID NO 282
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 282
gaugaccaua gaaaugaccu cgaacaa                                          27

<210> SEQ ID NO 283
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 283
agaugaccau agaaaugacc ucgaaca                                          27
```

```
<210> SEQ ID NO 284
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 284
gagaugacca uagaaaugac cucgaac                                          27

<210> SEQ ID NO 285
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 285
cgagaugacc auagaaauga ccucgaa                                          27

<210> SEQ ID NO 286
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 286
ucgagaugac cauagaaaug accucga                                          27

<210> SEQ ID NO 287
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 287
gucgagauga ccauagaaau gaccucg                                          27

<210> SEQ ID NO 288
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 288
agucgagaug accauagaaa ugaccuc                                          27

<210> SEQ ID NO 289
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 289
aagucgagau gaccauagaa augaccu                                          27

<210> SEQ ID NO 290
<211> LENGTH: 27
<212> TYPE: RNA
<213> ORGANISM: Artificial Sequence
<220> FEATURE:
```

<223> OTHER INFORMATION: Synthetic Polynucleotide

<400> SEQUENCE: 290
aaugaaaagg aacaaagucu uuucaag                                              27

<210> SEQ ID NO 291
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 291
caaugaaaag gaacaaaguc uuuucaa                                              27

<210> SEQ ID NO 292
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 292
agcaaugaaa aggaacaaag ucuuuuc                                              27

<210> SEQ ID NO 293
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 293
ugaugucacu uuuaugcauc cucagca                                              27

<210> SEQ ID NO 294
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 294
ugugauguca cuuuuaugca uccucag                                              27

<210> SEQ ID NO 295
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 295
uugucuuggc aggcauaaug aaaaaca                                              27

<210> SEQ ID NO 296
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 296
uuauuugucu uggcaggcau aaugaaa                                              27

-continued

```
<210> SEQ ID NO 297
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 297
auuauuuguc uuggcaggca uaaugaa                                            27

<210> SEQ ID NO 298
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 298
aauuauuugu cuuggcaggc auaauga                                            27

<210> SEQ ID NO 299
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 299
ugaaauuauu ugucuuggca ggcauaa                                            27

<210> SEQ ID NO 300
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 300
cuuucagggu uuccacguug aaauuau                                            27

<210> SEQ ID NO 301
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 301
ccuuucaggg uuccacguu gaaauua                                             27

<210> SEQ ID NO 302
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 302
uccuuucagg guuccacgu ugaaauu                                             27

<210> SEQ ID NO 303
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 303
guccuuucag gguuuccacg uugaaau                                               27

<210> SEQ ID NO 304
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 304
uguccuuuca ggguuccac guugaaa                                                27

<210> SEQ ID NO 305
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 305
aacuuuuccu ucacagaaug ugcaaca                                               27

<210> SEQ ID NO 306
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 306
aaacuuuucc uucacagaau gugcaac                                               27

<210> SEQ ID NO 307
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 307
caaacuuuuc cuucacagaa ugugcaa                                               27

<210> SEQ ID NO 308
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 308
uuuccaaacu uuuccuucac agaaugu                                               27

<210> SEQ ID NO 309
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 309
guuuuuuucc aaacuuuucc uucacag                                               27

<210> SEQ ID NO 310
<211> LENGTH: 27
```

```
<212> TYPE: RNA
<213> ORGANISM: Artificial Sequence
<220> FEATURE:
<223> OTHER INFORMATION: Synthetic Polynucleotide

<400> SEQUENCE: 310
aauaaugcau cauagaguuu uuuucca                                              27

<210> SEQ ID NO 311
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 311
uaauaaugca ucauagaguu uuuuucc                                              27

<210> SEQ ID NO 312
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 312
uuaauaaugc aucauagagu uuuuuuc                                              27

<210> SEQ ID NO 313
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 313
cuuaauaaug caucauagag uuuuuuu                                              27

<210> SEQ ID NO 314
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 314
ggucaggaau uucccucuu aauaaug                                               27

<210> SEQ ID NO 315
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 315
aggucaggaa uuucccucu uaauaau                                               27

<210> SEQ ID NO 316
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 316
```
caggucagga auuucuccuc uuaauaa                                       27

<210> SEQ ID NO 317
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 317
ucaggucagg aauuucuccu cuuaaua                                       27

<210> SEQ ID NO 318
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 318
uucaggucag gaauuucucc ucuuaau                                       27

<210> SEQ ID NO 319
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 319
guucagguca ggaauuucuc cucuuaa                                       27

<210> SEQ ID NO 320
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 320
uuuucauaau uguuagauca ucucgau                                       27

<210> SEQ ID NO 321
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 321
ucuuuucaua auuguuagau caucucg                                       27

<210> SEQ ID NO 322
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 322
cucuuuucau aauuguuaga ucaucuc                                       27

<210> SEQ ID NO 323
<211> LENGTH: 27
<212> TYPE: RNA
<213> ORGANISM: Artificial Sequence

```
<220> FEATURE:
<223> OTHER INFORMATION: Synthetic Polynucleotide

<400> SEQUENCE: 323
gcucuuuuca uaauuguuag aucaucu                                              27

<210> SEQ ID NO 324
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 324
aaaagauggc ucuuuucaua auuguua                                              27

<210> SEQ ID NO 325
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 325
cugaguugaa aagauggcuc uuuucau                                              27

<210> SEQ ID NO 326
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 326
uccgucuaau ggugcugagg auggggu                                              27

<210> SEQ ID NO 327
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 327
auccgucuaa uggugcugag gaugggg                                              27

<210> SEQ ID NO 328
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 328
aauccgucua auggugcuga ggauggg                                              27

<210> SEQ ID NO 329
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 329
caauccgucu aauggugcug aggaugg                                              27
```

```
<210> SEQ ID NO 330
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 330
ccaauccguc uaauggugcu gaggaug                                      27

<210> SEQ ID NO 331
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 331
uaacaaacuc uucauagucc augggua                                      27

<210> SEQ ID NO 332
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 332
cuaacaaacu cuucauaguc caugggu                                      27

<210> SEQ ID NO 333
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 333
cauaguauga uggaaauacu ccaagau                                      27

<210> SEQ ID NO 334
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 334
uucauaguau gauggaaaua cuccaag                                      27

<210> SEQ ID NO 335
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 335
guucauagua ugauggaaau acuccaa                                      27

<210> SEQ ID NO 336
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 336
gguucauagu augauggaaa uacucca                                               27

<210> SEQ ID NO 337
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 337 cagguucau aguaugaugg aaauacu                                                27

<210> SEQ ID NO 338
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 338
aucacagugc auucagcugg aguauaa                                               27

<210> SEQ ID NO 339
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 339
gucuggcaug cugguaauau cugccua                                               27

<210> SEQ ID NO 340
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 340
ugucuggcau gcugguaaua ucugccu                                               27

<210> SEQ ID NO 341
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 341
gugucuggca ugcugguaau aucugcc                                               27

<210> SEQ ID NO 342
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 342
ggugucuggc augcugguaa uaucugc                                               27

<210> SEQ ID NO 343
```

```
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 343
aggugucugg caugcuggua auaucug                                              27

<210> SEQ ID NO 344
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 344
caggugucug gcaugcuggu aauaucu                                              27

<210> SEQ ID NO 345
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 345
ucaggugucu ggcaugcugg uaauauc                                              27

<210> SEQ ID NO 346
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 346
gucagguguc uggcaugcug guaauau                                              27

<210> SEQ ID NO 347
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 347
ugucaggugu cuggcaugcu gguaaua                                              27

<210> SEQ ID NO 348
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 348
augucaggug ucuggcaugc ugguaau                                              27

<210> SEQ ID NO 349
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 349
```
aaugucaggu gucuggcaug cugguaa                                      27

<210> SEQ ID NO 350
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 350
uaaugucagg ugucuggcau gcuggua                                      27

<210> SEQ ID NO 351
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 351
uuaaugucag gugucuggca ugcuggu                                      27

<210> SEQ ID NO 352
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 352
cuuaauguca ggugucuggc augcugg                                      27

<210> SEQ ID NO 353
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 353
gcuuaauguc aggugucugg caugcug                                      27

<210> SEQ ID NO 354
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 354
ucugcuuaau gucagguguc uggcaug                                      27

<210> SEQ ID NO 355
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 355
uggaaaagcu cugcuuaaug ucaggug                                      27

<210> SEQ ID NO 356
<211> LENGTH: 27
<212> TYPE: RNA

<213> ORGANISM: Artificial Sequence
<220> FEATURE:
<223> OTHER INFORMATION: Synthetic Polynucleotide

<400> SEQUENCE: 356
gaauuuaucu ggaaaagcuc ugcuuaa                                27

<210> SEQ ID NO 357
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 357
uggaauuuau cuggaaaagc ucugcuu                                27

<210> SEQ ID NO 358
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 358 uuaguccac auggaauuua ucuggaa                                 27

<210> SEQ ID NO 359
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 359
guuaguucca cauggaauuu aucugga                                27

<210> SEQ ID NO 360
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 360
cugaaggaga aggugguacu gaggaag                                27

<210> SEQ ID NO 361
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 361
ccugaaggag aaggugguac ugaggaa                                27

<210> SEQ ID NO 362
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 362
acuugauauu uaaccgaucc cuuucag                                27

<210> SEQ ID NO 363
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 363
gugacuugau auuaaccga ucccuuu                                          27

<210> SEQ ID NO 364
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 364
aauggugacu ugauauuuaa ccgaucc                                         27

<210> SEQ ID NO 365
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 365
gaaaauggug acuugauauu uaaccga                                         27

<210> SEQ ID NO 366
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 366
ugaaaauggu gacuugauau uuaaccg                                         27

<210> SEQ ID NO 367
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 367
cagugaaaau ggugacuuga uauuuaa                                         27

<210> SEQ ID NO 368
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 368
uauauucacc augcagcuuu uucuucc                                         27

<210> SEQ ID NO 369
<211> LENGTH: 27
<212> TYPE: RNA
<213> ORGANISM: Artificial Sequence
<220> FEATURE:

<223> OTHER INFORMATION: Synthetic Polynucleotide

<400> SEQUENCE: 369
uuauauucac caugcagcuu uuucuuc                                              27

<210> SEQ ID NO 370
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 370
ucuuauauuc accaugcagc uuuuucu                                              27

<210> SEQ ID NO 371
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 371
uucuuauauu caccaugcag cuuuuuc                                              27

<210> SEQ ID NO 372
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 372
aguucuuaua uucaccaugc agcuuuu                                              27

<210> SEQ ID NO 373
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 373
ucaguucuua uauucaccau gcagcuu                                              27

<210> SEQ ID NO 374
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 374
uucaguucuu auauucacca ugcagcu                                              27

<210> SEQ ID NO 375
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 375
aauucaguuc uuauauucac caugcag                                              27

```
<210> SEQ ID NO 376
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 376
gaauucaguu cuuauauuca ccaugca                                      27

<210> SEQ ID NO 377
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 377
agaauucagu ucuuauauuc accaugc                                      27

<210> SEQ ID NO 378
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 378
uagaauucag uucuuauauu caccaug                                      27

<210> SEQ ID NO 379
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 379
guagaauuca guucuuauau ucaccau                                      27

<210> SEQ ID NO 380
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 380
uguagaauuc aguucuuaua uuccacca                                     27

<210> SEQ ID NO 381
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 381
acauguagaa uucaguucuu auauuca                                      27

<210> SEQ ID NO 382
<211> LENGTH: 27
<212> TYPE: RNA
<213> ORGANISM: Artificial Sequence
<220> FEATURE:
<223> OTHER INFORMATION: Synthetic Polynucleotide
```

<400> SEQUENCE: 382
cacauguaga auucaguucu uauauuc     27

<210> SEQ ID NO 383
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 383
agcacaugua gaauucaguu cuuauau     27

<210> SEQ ID NO 384
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 384
gcagcacaug uagaauucag uucuuau     27

<210> SEQ ID NO 385
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 385
aggugcauuu uggaagaugg gcagccgaaa ggcugc     36

<210> SEQ ID NO 386
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 386
aggugcauuu uggaagaugg cagccgaaag gcugc     35

<210> SEQ ID NO 387
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 387
ggugcauuuu ggaagauggc gcagccgaaa ggcugc     36

<210> SEQ ID NO 388
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 388
ggugcauuuu ggaagauggg cagccgaaag gcugc     35

<210> SEQ ID NO 389
<211> LENGTH: 36

```
<212> TYPE: RNA
<213> ORGANISM: Artificial Sequence
<220> FEATURE:
<223> OTHER INFORMATION: Synthetic Polynucleotide

<400> SEQUENCE: 389
aaggaagucc uuauguggua gcagccgaaa ggcugc                              36

<210> SEQ ID NO 390
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 390
aaggaagucc uuaugugguɡ cagccgaaag gcugc                               35

<210> SEQ ID NO 391
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 391
augauaugcu gauauuugga gcagccgaaa ggcugc                              36

<210> SEQ ID NO 392
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 392
augauaugcu gauauuuggg cagccgaaag gcugc                               35

<210> SEQ ID NO 393
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 393
agcaaauauu gauuucuaca gcagccgaaa ggcugc                              36

<210> SEQ ID NO 394
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 394
agcaaauauu gauuucuacg cagccgaaag gcugc                               35

<210> SEQ ID NO 395
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 395
```

```
ccacgguuuc ugaaauaaca gcagccgaaa ggcugc                              36
```

<210> SEQ ID NO 396
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 396

```
ccacgguuuc ugaaauaacg cagccgaaag gcugc                               35
```

<210> SEQ ID NO 397
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 397

```
cuugaauguu aagaaauuuu gcagccgaaa ggcugc                              36
```

<210> SEQ ID NO 398
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 398

```
cuugaauguu aagaaauuug cagccgaaag gcugc                               35
```

<210> SEQ ID NO 399
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 399

```
ugaauguuaa gaaauuuuca gcagccgaaa ggcugc                              36
```

<210> SEQ ID NO 400
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 400

```
ugaauguuaa gaaauuucg cagccgaaag gcugc                                35
```

<210> SEQ ID NO 401
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 401

```
cgaggucauu ucuaugguca gcagccgaaa ggcugc                              36
```

<210> SEQ ID NO 402
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 402
cgaggucauu ucuauggucg cagccgaaag gcugc    35

<210> SEQ ID NO 403
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 403 auucgugaa ggaaaaguuu gcagccgaaa ggcugc    36

<210> SEQ ID NO 404
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 404 auucgugaa ggaaaaguug cagccgaaag gcugc    35

<210> SEQ ID NO 405
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 405
cuuggaguau uuccaucaua gcagccgaaa ggcugc    36

<210> SEQ ID NO 406
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 406
cuuggaguau uuccaucaug cagccgaaag gcugc    35

<210> SEQ ID NO 407
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 407
uggaguauuu ccaucauacu gcagccgaaa ggcugc    36

<210> SEQ ID NO 408
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 408
uggaguauuu ccaucauacg cagccgaaag gcugc    35

```
<210> SEQ ID NO 409
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 409
gaguauuucc aucauacuau gcagccgaaa ggcugc                         36

<210> SEQ ID NO 410
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 410
gaguauuucc aucauacuag cagccgaaag gcugc                          35

<210> SEQ ID NO 411
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 411
ccagcaugcc agacaccuga gcagccgaaa ggcugc                         36

<210> SEQ ID NO 412
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 412
ccagcaugcc agacaccugg cagccgaaag gcugc                          35

<210> SEQ ID NO 413
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 413
agaaaaagcu gcauggugaa gcagccgaaa ggcugc                         36

<210> SEQ ID NO 414
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 414
agaaaaagcu gcauggugag cagccgaaag gcugc                          35

<210> SEQ ID NO 415
<211> LENGTH: 36
<212> TYPE: RNA
<213> ORGANISM: Artificial Sequence
<220> FEATURE:
<223> OTHER INFORMATION: Synthetic Polynucleotide
```

<400> SEQUENCE: 415
uggugaauau aagaacugaa gcagccgaaa ggcugc    36

<210> SEQ ID NO 416
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 416
uggugaauau aagaacugag cagccgaaag gcugc    35

<210> SEQ ID NO 417
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 417
ccaucuucca aaaugcaccu gg    22

<210> SEQ ID NO 418
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 418
caucuuccaa aaugcaccug g    21

<210> SEQ ID NO 419
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 419
gccaucuucc aaaaugcacc ug    22

<210> SEQ ID NO 420
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 420
ccaucuucca aaaugcaccu g    21

<210> SEQ ID NO 421
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 421
uaccacauaa ggacuuccuu cu    22

<210> SEQ ID NO 422

```
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 422
uaccacauaa ggacuucctu cu                                                  22

<210> SEQ ID NO 423
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 423
accacauaag gacuuccuc u                                                    21

<210> SEQ ID NO 424
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 424
accacauaag gacuuccuuc u                                                   21

<210> SEQ ID NO 425
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 425
uccaaauauc agcauaucau ug                                                  22

<210> SEQ ID NO 426
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 426
uccaaauauc agcauatcau ug                                                  22

<210> SEQ ID NO 427
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 427
ccaaauauca gcauatcauu g                                                   21

<210> SEQ ID NO 428
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 428
```

-continued

```
ccaaauauca gcauaucauu g                                        21

<210> SEQ ID NO 429
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 429
uguagaaauc aauauuugcu gc                                       22

<210> SEQ ID NO 430
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 430
uguagaaauc aatauutgcu gc                                       22

<210> SEQ ID NO 431
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 431
gtagaaauca atauutgcug c                                        21

<210> SEQ ID NO 432
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 432
guagaaauca auauuugcug c                                        21

<210> SEQ ID NO 433
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 433
uguuauuuca gaaaccgugg ug                                       22

<210> SEQ ID NO 434
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 434
gtuauuucag aaaccguggu g                                        21

<210> SEQ ID NO 435
<211> LENGTH: 21
<212> TYPE: RNA
```

```
<213> ORGANISM: Artificial Sequence
<220> FEATURE:
<223> OTHER INFORMATION: Synthetic Polynucleotide

<400> SEQUENCE: 435
guuauuucag aaaccguggu g                                              21

<210> SEQ ID NO 436
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 436
aaaauuucuu aacauucaag cc                                             22

<210> SEQ ID NO 437
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 437
aaauuucuua acauucaagc c                                              21

<210> SEQ ID NO 438
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 438
ugaaaauuuc uuaacauuca ag                                             22

<210> SEQ ID NO 439
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 439
ugaaaauuuc uuaacatuca ag                                             22

<210> SEQ ID NO 440
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 440
gaaaauuucu aacatucaa g                                               21

<210> SEQ ID NO 441
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 441
gaaaauuucu uaacauucaa g                                              21
```

-continued

<210> SEQ ID NO 442
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 442
ugaccauaga aaugaccucg aa                                              22

<210> SEQ ID NO 443
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 443
ugaccauaga aatgaccucg aa                                              22

<210> SEQ ID NO 444
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 444
gaccauagaa atgaccucga a                                               21

<210> SEQ ID NO 445
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 445
gaccauagaa augaccucga a                                               21

<210> SEQ ID NO 446
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 446
aaacuuuucc uucacagaau gu                                              22

<210> SEQ ID NO 447
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 447
aacuuuuccu ucacagaaug u                                               21

<210> SEQ ID NO 448
<211> LENGTH: 22
<212> TYPE: RNA
<213> ORGANISM: Artificial Sequence
<220> FEATURE:

<223> OTHER INFORMATION: Synthetic Polynucleotide

<400> SEQUENCE: 448
uaugauggaa auacuccaag au                                    22

<210> SEQ ID NO 449
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 449
atgauggaaa uacuccaaga u                                     21

<210> SEQ ID NO 450
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 450
augauggaaa uacuccaaga u                                     21

<210> SEQ ID NO 451
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 451
aguaugaugg aaauacucca ag                                    22

<210> SEQ ID NO 452
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 452
aguaugaugg aaauactcca ag                                    22

<210> SEQ ID NO 453
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 453
gtaugaugga aauactccaa g                                     21

<210> SEQ ID NO 454
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 454
guaugaugga aauacuccaa g                                     21

```
<210> SEQ ID NO 455
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 455
auaguaugau ggaaauacuc ca                                             22

<210> SEQ ID NO 456
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 456
ataguaugau ggaaauactc ca                                             22

<210> SEQ ID NO 457
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 457
uaguaugaug gaaauactcc a                                              21

<210> SEQ ID NO 458
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 458
uaguaugaug gaaauacucc a                                              21

<210> SEQ ID NO 459
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 459
ucaggugucu ggcaugcugg ua                                             22

<210> SEQ ID NO 460
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 460
caggugucug gcaugcuggu a                                              21

<210> SEQ ID NO 461
<211> LENGTH: 22
<212> TYPE: RNA
<213> ORGANISM: Artificial Sequence
<220> FEATURE:
<223> OTHER INFORMATION: Synthetic Polynucleotide
```

<400> SEQUENCE: 461
uucaccaugc agcuuuuucu uc                                    22

<210> SEQ ID NO 462
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 462
utcaccaugc agcuuutucu uc                                    22

<210> SEQ ID NO 463
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 463
ucaccaugca gcuuutucuu c                                     21

<210> SEQ ID NO 464
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 464
ucaccaugca gcuuuuucuu c                                     21

<210> SEQ ID NO 465
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 465
uucaguucuu auauucacca ug                                    22

<210> SEQ ID NO 466
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 466
ucaguucuua uauucaccau g                                     21

<210> SEQ ID NO 467
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 467
ggaggcaucu auacugugau ucaga                                 25

<210> SEQ ID NO 468
<211> LENGTH: 25

```
<212> TYPE: RNA
<213> ORGANISM: Artificial Sequence
<220> FEATURE:
<223> OTHER INFORMATION: Synthetic Polynucleotide

<400> SEQUENCE: 468
ggcaucuaua cugugauuca gacaa                                   25

<210> SEQ ID NO 469
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 469
gcaucuauac ugugauucag acaaa                                   25

<210> SEQ ID NO 470
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 470
guccauauuu ugagcauaau augaa                                   25

<210> SEQ ID NO 471
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 471 auauuugag cauaauauga agact                                    25

<210> SEQ ID NO 472
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 472
acggcuugaa uguuaagaaa uuutc                                   25

<210> SEQ ID NO 473
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 473
cggcuugaau guuaagaaau uuuca                                   25

<210> SEQ ID NO 474
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 474
```
aauguuaaga aauuuucagc agugc                                              25

<210> SEQ ID NO 475
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 475
uguuaagaaa uuuucagcag ugcat                                              25

<210> SEQ ID NO 476
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 476
guuaagaaau uuucagcagu gcatg                                              25

<210> SEQ ID NO 477
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 477
ugcaugguga auauaagaac ugaat                                              25

<210> SEQ ID NO 478
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 478
ugaauauaag aacugaauuc uacat                                              25

<210> SEQ ID NO 479
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 479
gaauauaaga acugaauucu acatg                                              25

<210> SEQ ID NO 480
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 480
caaaguaaga cuaauuauuu aaaat                                              25

<210> SEQ ID NO 481
<211> LENGTH: 25
<212> TYPE: DNA
<213> ORGANISM: Artificial Sequence

```
<220> FEATURE:
<223> OTHER INFORMATION: Synthetic Polynucleotide

<400> SEQUENCE: 481
aaaguaagac uaauuauuua aaata                                              25

<210> SEQ ID NO 482
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 482
agaaauugag ugaaugacaa uuutg                                              25

<210> SEQ ID NO 483
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 483
aaauugagug augacaauu uugta                                               25

<210> SEQ ID NO 484
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 484
auugagugaa ugacaauuuu guaat                                              25

<210> SEQ ID NO 485
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 485
aaugacaauu uuguaauuua ggata                                              25

<210> SEQ ID NO 486
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 486
aaguguuuuu aaaugguga auuta                                               25

<210> SEQ ID NO 487
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 487
aguguuuuua aaauggugaa uuuaa                                              25
```

```
<210> SEQ ID NO 488
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 488
cuuacucugu uuauuuuaa augat                                          25

<210> SEQ ID NO 489
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 489
cucuguuuau uuuaaauga ucatc                                          25

<210> SEQ ID NO 490
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 490
ucuguuuauu uuaaaugau cauca                                          25

<210> SEQ ID NO 491
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 491
guuuauuuuu aaaugaucau cauaa                                         25

<210> SEQ ID NO 492
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 492
aucaucauaa uccuuugcuu acuat                                         25

<210> SEQ ID NO 493
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 493
gugcacuacc uacauuuuuu aaata                                         25

<210> SEQ ID NO 494
<211> LENGTH: 25
<212> TYPE: RNA
<213> ORGANISM: Artificial Sequence
<220> FEATURE:
<223> OTHER INFORMATION: Synthetic Polynucleotide
```

-continued

<400> SEQUENCE: 494
gcuagguuuu uacugauuau uuuca 25

<210> SEQ ID NO 495
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 495
cuagguuuuu acugauuauu uucat 25

<210> SEQ ID NO 496
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 496
agguuuuuac ugauuauuuu cautt 25

<210> SEQ ID NO 497
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 497
cugauuauuu ucauuuuuca caugc 25

<210> SEQ ID NO 498
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 498
auggacauuu augucacuuu ugaaa 25

<210> SEQ ID NO 499
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 499
gacauuuaug ucacuuuuga aauct 25

<210> SEQ ID NO 500
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 500
acauuuaugu cacuuuugaa aucta 25

<210> SEQ ID NO 501

```
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 501
uagaauugau guguaauua augca                                              25

<210> SEQ ID NO 502
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 502
agaauugaug uuguaauuaa ugcaa                                             25

<210> SEQ ID NO 503
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 503
gaauugaugu uguaauuaau gcaag                                             25

<210> SEQ ID NO 504
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 504
accaucuuac uguaacauuu uucta                                             25

<210> SEQ ID NO 505
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 505
caucuuacug uaacauuuuu cuatt                                             25

<210> SEQ ID NO 506
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 506
ucuuacugua acauuuuucu auugt                                             25

<210> SEQ ID NO 507
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 507
```
cuuacuguaa cauuuucua uugtt                                              25

<210> SEQ ID NO 508
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 508
uuacuguaac auuuucuau ugutt                                              25

<210> SEQ ID NO 509
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 509
acuguaacau uuucuauug uuuaa                                              25

<210> SEQ ID NO 510
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 510
cuguaacauu uuucuauugu uuaaa                                             25

<210> SEQ ID NO 511
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 511
uguaacauuu uucuauuguu uaaat                                             25

<210> SEQ ID NO 512
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 512
guaacauuuu ucuauuguuu aaata                                             25

<210> SEQ ID NO 513
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 513
uaacauuuuu cuauuguuua aauag                                             25

<210> SEQ ID NO 514
<211> LENGTH: 25
<212> TYPE: RNA

```
<213> ORGANISM: Artificial Sequence
<220> FEATURE:
<223> OTHER INFORMATION: Synthetic Polynucleotide

<400> SEQUENCE: 514 aacauuuuc uauuguuuaa auaga                                           25

<210> SEQ ID NO 515
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 515
acauuuuucu auuguuuaaa uagaa                                          25

<210> SEQ ID NO 516
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 516 cauuuucua uuguuuaaau agaaa                                           25

<210> SEQ ID NO 517
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 517
gucaaucuuc auagaugaua acutg                                          25

<210> SEQ ID NO 518
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 518
ucugaaucac aguauagaug ccuccaa                                        27

<210> SEQ ID NO 519
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 519
uugucugaau cacaguauag augccuc                                        27

<210> SEQ ID NO 520
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 520
uuugucugaa ucacaguaua gaugccu                                        27
```

```
<210> SEQ ID NO 521
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 521
uucauauuau gcucaaaaua uggaccu                                              27

<210> SEQ ID NO 522
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 522
agucuucaua uuaugcucaa aauaugg                                              27

<210> SEQ ID NO 523
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 523
gaaaauuucu uaacauucaa gccguuu                                              27

<210> SEQ ID NO 524
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 524
ugaaaauuuc uuaacauuca agccguu                                              27

<210> SEQ ID NO 525
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 525
gcacugcuga aaauucuua acauuca                                               27

<210> SEQ ID NO 526
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 526
augcacugcu gaaaauuucu uaacauu                                              27

<210> SEQ ID NO 527
<211> LENGTH: 27
<212> TYPE: RNA
<213> ORGANISM: Artificial Sequence
<220> FEATURE:
```

<223> OTHER INFORMATION: Synthetic Polynucleotide

<400> SEQUENCE: 527
caugcacugc ugaaaauuuc uuaacau                                              27

<210> SEQ ID NO 528
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 528
auucaguucu uauauucacc augcagc                                              27

<210> SEQ ID NO 529
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 529
auguagaauu caguucuuau auucacc                                              27

<210> SEQ ID NO 530
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 530
cauguagaau ucaguucuua uauucac                                              27

<210> SEQ ID NO 531
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 531
auuuuaaaua auuagucuua cuuugcu                                              27

<210> SEQ ID NO 532
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 532
uauuuuaaau aauuagucuu acuuugc                                              27

<210> SEQ ID NO 533
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 533
caaaauuguc auucacucaa uuucuuc                                              27

```
<210> SEQ ID NO 534
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 534
uacaaaauug ucauucacuc aauuucu                                          27

<210> SEQ ID NO 535
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 535
auuacaaaau ugucauucac ucaauuu                                          27

<210> SEQ ID NO 536
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 536
uauccuaaau uacaaaauug ucauuca                                          27

<210> SEQ ID NO 537
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 537
uaaauucacc auuuuaaaaa cacuuuu                                          27

<210> SEQ ID NO 538
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 538
uuaaauucac cauuuuaaaa acacuuu                                          27

<210> SEQ ID NO 539
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 539
aucauuuaaa aauaaacaga guaagag                                          27

<210> SEQ ID NO 540
<211> LENGTH: 27
<212> TYPE: RNA
<213> ORGANISM: Artificial Sequence
<220> FEATURE:
<223> OTHER INFORMATION: Synthetic Polynucleotide
```

```
<400> SEQUENCE: 540
gaugaucauu uaaaaauaaa cagagua                                              27

<210> SEQ ID NO 541
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 541
ugaugaucau uuaaaaauaa acagagu                                              27

<210> SEQ ID NO 542
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 542
uuaugaugau cauuuaaaaa uaaacag                                              27

<210> SEQ ID NO 543
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 543
auaguaagca aaggauuaug augauca                                              27

<210> SEQ ID NO 544
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 544
uauuuaaaaa auguagguag ugcacau                                              27

<210> SEQ ID NO 545
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 545
ugaaaauaau caguaaaaac cuagcua                                              27

<210> SEQ ID NO 546
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 546
augaaaauaa ucaguaaaaa ccuagcu                                              27

<210> SEQ ID NO 547
<211> LENGTH: 27
```

```
<212> TYPE: RNA
<213> ORGANISM: Artificial Sequence
<220> FEATURE:
<223> OTHER INFORMATION: Synthetic Polynucleotide

<400> SEQUENCE: 547
aaaugaaaau aaucaguaaa aaccuag                                        27

<210> SEQ ID NO 548
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 548
gcaugugaaa aaugaaaaua aucagua                                        27

<210> SEQ ID NO 549
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 549
uuucaaaagu gacauaaaug uccauua                                        27

<210> SEQ ID NO 550
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 550
agauuucaaa agugacauaa augucca                                        27

<210> SEQ ID NO 551
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 551
uagauuucaa aagugacaua aaugucc                                        27

<210> SEQ ID NO 552
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 552
ugcauuaauu acaacaucaa uucuaga                                        27

<210> SEQ ID NO 553
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 553
```
uugcauuaau uacaacauca auucuag          27

<210> SEQ ID NO 554
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 554
cuugcauuaa uuacaacauc aauucua          27

<210> SEQ ID NO 555
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 555
uagaaaaaug uuacaguaag auggugg          27

<210> SEQ ID NO 556
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 556
aauagaaaaa uguuacagua agauggu          27

<210> SEQ ID NO 557
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 557
acaauagaaa aauguuacag uaagaug          27

<210> SEQ ID NO 558
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 558
aacaauagaa aaauguuaca guaagau          27

<210> SEQ ID NO 559
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 559
aaacaauaga aaauguuac aguaaga          27

<210> SEQ ID NO 560
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 560
uuaaacaaua gaaaaauguu acaguaa 27

<210> SEQ ID NO 561
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 561
uuuaaacaau agaaaaaugu uacagua 27

<210> SEQ ID NO 562
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 562
auuuaaacaa uagaaaaaug uuacagu 27

<210> SEQ ID NO 563
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 563
uauuuaaaca auagaaaaau guuacag 27

<210> SEQ ID NO 564
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 564
cuauuuaaac aauagaaaaa uguuaca 27

<210> SEQ ID NO 565
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 565
ucuauuuaaa caauagaaaa auguuac 27

<210> SEQ ID NO 566
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 566
uucuauuuaa acaauagaaa aauguua 27

<210> SEQ ID NO 567
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 567
uuucuauuua aacaauagaa aaauguu                                       27

<210> SEQ ID NO 568
<211> LENGTH: 27
<212> TYPE: RNA
<213> ORGANISM: Artificial Sequence
<220> FEATURE:
<223> OTHER INFORMATION: Synthetic Polynucleotide

<400> SEQUENCE: 568
caaguuauca ucuaugaaga uugacca                                       27

<210> SEQ ID NO 569
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 569
ggcaucuaua cugugauuca gcagccgaaa ggcugc                             36

<210> SEQ ID NO 570
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 570
gcaucuauac ugugauucag gcagccgaaa ggcugc                             36

<210> SEQ ID NO 571
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 571
gcagcaaaua uugauuucua gcagccgaaa ggcugc                             36

<210> SEQ ID NO 572
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 572
cugaaauaac agcaauagaa gcagccgaaa ggcugc                             36

<210> SEQ ID NO 573
<211> LENGTH: 36
<212> TYPE: RNA
<213> ORGANISM: Artificial Sequence
<220> FEATURE:
<223> OTHER INFORMATION: Synthetic Polynucleotide

```
<400> SEQUENCE: 573
acggcuugaa uguuaagaaa gcagccgaaa ggcugc                               36

<210> SEQ ID NO 574
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 574
aguguuuuua aaauggugaa gcagccgaaa ggcugc                              36

<210> SEQ ID NO 575
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 575
ugaaucacag uauagaugcc gg                                             22

<210> SEQ ID NO 576
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 576
cugaaucaca guauagaugc gg                                             22

<210> SEQ ID NO 577
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 577
uagaaaucaa uauuugcugc gg                                             22

<210> SEQ ID NO 578
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 578
uucuauugcu guuauuucag gg                                             22

<210> SEQ ID NO 579
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 579
uuucuuaaca uucaagccgu gg                                             22

<210> SEQ ID NO 580
```

```
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 580
uucaccauuu uaaaaacacu gg                                                   22

<210> SEQ ID NO 581
<211> LENGTH: 35
<212> TYPE: RNA
<213> ORGANISM: Artificial Sequence
<220> FEATURE:
<223> OTHER INFORMATION: Synthetic Polynucleotide

<400> SEQUENCE: 581
gaauguuaag aaauuuucag cagccgaaag gcugc                                     35

<210> SEQ ID NO 582
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 582
ugcaugaguu ucaaaaucua gcagccgaaa ggcugc                                    36

<210> SEQ ID NO 583
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 583
ucgagaugau cuaacaauua gcagccgaaa ggcugc                                    36

<210> SEQ ID NO 584
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 584
agacuaauua uuuaaaauaa gcagccgaaa ggcugc                                    36

<210> SEQ ID NO 585
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 585
agaauugaug uuguaauuaa gcagccgaaa ggcugc                                    36

<210> SEQ ID NO 586
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 586
```
uaaauuucuu aacauucaag gg                                         22

<210> SEQ ID NO 587
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 587
aaauuucuua acauucaagg g                                          21

<210> SEQ ID NO 588
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 588
uucaccaugc agcuuuuucu gg                                         22

<210> SEQ ID NO 589
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 589
ucaccaugca gcuuuuucug g                                          21

<210> SEQ ID NO 590
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 590
ugaaaauuuc uuaacauuca gg                                         22

<210> SEQ ID NO 591
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 591
uucaguucuu auauucacca gg                                         22

<210> SEQ ID NO 592
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 592
aaaauuucuu aacauucaag gg                                         22

<210> SEQ ID NO 593
<211> LENGTH: 21
<212> TYPE: RNA

-continued

```
<213> ORGANISM: Artificial Sequence
<220> FEATURE:
<223> OTHER INFORMATION: Synthetic Polynucleotide

<400> SEQUENCE: 593
ugaaaauuuc uuaacauucg g                                                   21

<210> SEQ ID NO 594
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 594
uagauuuuga aacucaugca gg                                                  22

<210> SEQ ID NO 595
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 595
uaauuguuag aucaucucga gg                                                  22

<210> SEQ ID NO 596
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 596
uuauuuuaaa uaauuagucu gg                                                  22

<210> SEQ ID NO 597
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 597
uuaauuacaa caucaauucu gg                                                  22

<210> SEQ ID NO 598
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 598
utcaguucuu auauucacca ug                                                  22

<210> SEQ ID NO 599
<211> LENGTH: 40
<212> TYPE: DNA
<213> ORGANISM: Homo sapiens

<400> SEQUENCE: 599
gatagaagga agtccttatg tggtactttt tgacataggc                               40
```

```
<210> SEQ ID NO 600
<211> LENGTH: 48
<212> TYPE: DNA
<213> ORGANISM: Homo sapiens

<400> SEQUENCE: 600
gaccgagaag ccaatgatat gctgatattt ggatctttaa ctgcctgg            48

<210> SEQ ID NO 601
<211> LENGTH: 37
<212> TYPE: DNA
<213> ORGANISM: Homo sapiens

<400> SEQUENCE: 601
tccaaacggc ttgaatgtta agaaattttc agcagtg                        37

<210> SEQ ID NO 602
<211> LENGTH: 37
<212> TYPE: DNA
<213> ORGANISM: Homo sapiens

<400> SEQUENCE: 602
ttgttcgagg tcatttctat ggtcatctcg actttga                        37

<210> SEQ ID NO 603
<211> LENGTH: 56
<212> TYPE: DNA
<213> ORGANISM: Homo sapiens

<400> SEQUENCE: 603
tgcacattct gtgaaggaaa agtttggaaa aaaactctat gatgcattat taagag    56

<210> SEQ ID NO 604
<211> LENGTH: 43
<212> TYPE: DNA
<213> ORGANISM: Homo sapiens

<400> SEQUENCE: 604
aagctgcatg gtgaatataa gaactgaatt ctacatgtgc tgc                 43

<210> SEQ ID NO 605
<211> LENGTH: 47
<212> TYPE: DNA
<213> ORGANISM: Homo sapiens

<400> SEQUENCE: 605
gtggaagaaa ttgagtgaat gacaattttg taatttagga taagatc             47

<210> SEQ ID NO 606
<211> LENGTH: 39
<212> TYPE: DNA
<213> ORGANISM: Homo sapiens

<400> SEQUENCE: 606
tttctcttac tctgtttatt tttaaatgat catcataat                      39

<210> SEQ ID NO 607
<211> LENGTH: 44
<212> TYPE: DNA
<213> ORGANISM: Homo sapiens

<400> SEQUENCE: 607
tagctaggtt tttactgatt attttcattt ttcacatgca tcag                44
```

<210> SEQ ID NO 608
<211> LENGTH: 37
<212> TYPE: DNA
<213> ORGANISM: Homo sapiens

<400> SEQUENCE: 608
tcttactgta acatttttct attgtttaaa tagaaag         37

<210> SEQ ID NO 609
<211> LENGTH: 3132
<212> TYPE: DNA
<213> ORGANISM: Homo sapiens

<400> SEQUENCE: 609

| | | | |
|---|---|---|---|
| agatactgac agggcagata ccgtcctcac aatacctgcc cagaaagacg agaaagagga | 60 |
| ggaagaattc ctccttccac caggaattct gtgggaagca cataagattt catgctacta | 120 |
| gtttattccc aagagaagct accaaagcct ggtaactcta ccaactctaa cttttgtgcc | 180 |
| tgtaagttct cttctcctgg gattacaact aattgaaaca ggaattcaaa ggagtctcgg | 240 |
| aggactgtaa gaagaatgct tcgaggccga tccctctctg taacatccct gggtgggctt | 300 |
| ccccagtggg aagtcgaaga acttcctgtg gaggagttac tgctctttga agttgcttgg | 360 |
| gaagtgacca ataaagttgg aggcatctat actgtgattc agacaaaggc caaaacaaca | 420 |
| gcagatgaat ggggagagaa ctattttctg ataggtccat attttgagca taatatgaag | 480 |
| actcaggtgg aacagtgtga acctgtaaat gatgctgtca agagcagt ggacgcaatg | 540 |
| aataagcatg gctgccaggt gcattttgga agatggctga tagaaggaag tccttatgtg | 600 |
| gtacttttg acataggcta ttcagcttgg aatctggaca ggtggaaggg tgacctctgg | 660 |
| gaagcatgca gtgtcggcat tcctatcat gaccgagaag ccaatgatat gctgatattt | 720 |
| ggatctttaa ctgcctggtt cttaaaagag gtgacagatc atgcagatgg taaatatgtc | 780 |
| gttgcccaat ccatgaatg gcaggctgga attggactga tccttctcg agccaggaaa | 840 |
| cttcctattg ccacaatatt tacaacccac gctacactac ttgggaggta tctctgtgca | 900 |
| gcaaatattg atttctacaa ccatcttgat aagtttaaca ttgacaaaga ggctgggaa | 960 |
| aggcagattt accaccggta ctgcatggag cgagcttccg ttcattgcgc tcacgtgttc | 1020 |
| accacggttt ctgaaataac agcaatagaa gctgaacata tgctgaagag aaagcctgat | 1080 |
| gtagttactc caaacggctt gaatgttaag aaattttcag cagtgcatga gtttcaaaat | 1140 |
| ctacatgcca tgtacaaggc cagaatccaa gattttgttc gaggtcattt ctatggtcat | 1200 |
| ctcgactttg atcttgaaaa gactttgttc ctttttcattg ctgggaggta tgagttttca | 1260 |
| aacaaaggag ctgacatctt cctagaatcc ttatccaggc taaatttcct gctgaggatg | 1320 |
| cataaaagtg acatcacagt gatggtgttt ttcattatgc ctgccaagac aaataatttc | 1380 |
| aacgtggaaa ccctgaaagg acaagcagtg cgaaaacagc tgtgggatgt tgcacattct | 1440 |
| gtgaaggaaa agtttggaaa aaaactctat gatgcattat taagaggaga aattcctgac | 1500 |
| ctgaacgata ttttagatcg agatgatcta acaattatga aaagagccat cttttcaact | 1560 |
| cagcgacagt cattgccccc agtgaccacg cacaacatga ttgatgactc caccgacccc | 1620 |
| atcctcagca ccattagacg gattggactt ttcaacaacc gcacagatag agtcaaggtg | 1680 |
| attttgcacc cagagtttct atcctccacc agtcccttac tacccatgga ctatgaagag | 1740 |
| tttgttagag ttgtcatctc tggagtattt ccatcatact atgaaccctg ggttatact | 1800 |
| ccagctgaat gcactgtgat gggtatcccc agtgtgacca cgaatctctc cgggtttggc | 1860 |

```
tgtttcatgc aggagcacgt ggctgatcct actgcttacg gtatttacat cgttgacagg    1920
cggttccgtt ctccagatga ttcttgcaat cagctgacta agtttctcta tggattttgc    1980
aaacagtcac gccgccaaag gattatccag aggaacagaa ctgagaggct ctcagatctt    2040
ctggattgga gatacttagg cagatattac cagcatgcca gacacctgac attaagcaga    2100
gcttttccag ataaattcca tgtggaacta acatcaccac caacgacaga aggatttaaa    2160
tatcccaggc cttcctcagt accaccttct ccttcagggt ctcaggcctc cagtcctcag    2220
agcagtgatg tggaagatga agtggaggat gagagatacg atgaggaaga ggaggctgaa    2280
agggatcggt taaatatcaa gtcaccattt tcactgagcc acgttcctca tgggaagaaa    2340
aagctgcatg gtgaatataa gaactgaatt ctacatgtgc tgcatgaaga gctaatttaa    2400
aaaagcaaag taagactaat tatttaaaat aaaaatgcca caaatttcat tttctccttc    2460
taagtattac aatggagttt attctctgcc taaaaagtgg aagaaattga gtgaatgaca    2520
attttgtaat ttaggataag atccaagtta ttttcccaa ctcttgtttc ccccataaag     2580
ttaggcatga ggaggagcac tcattaaagg cagaagacgg aaaagtgttt ttaaaatggt    2640
gaatttaagt ggtaaggatt ttctcttact ctgtttattt ttaaatgatc atcataatcc    2700
tttgcttact atttatgcag cttctctacc ccaccacaca aatttcccat ttccccccg     2760 aaaaccttga tcttacccat gaatgtgcac tacctacatt ttttaaatag ctaggttttt    2820
actgattatt ttcattttc acatgcatca gaaccatgat ttagatgtag ttttgcagag    2880
acaaaaatcc atgagtgaat agctatccta agtccatatt ttgatgcata ttaatggaca    2940
tttatgtcac ttttgaaatc tagaattgat gttgtaatta atgcaagata ttaccatgta    3000
catggtacca ccatcttact gtaacatttt tctattgttt aaatagaaag ccttttaaa    3060 atttggtcaa tcttcataga tgataacttg taaaatccaa gtaaataaac acattaatat    3120
ttaataactt aa    3132
```

<210> SEQ ID NO 610
<211> LENGTH: 3149
<212> TYPE: DNA
<213> ORGANISM: Macaca mulatta

<400> SEQUENCE: 610

```
agatactggt agggcagaaa cttcctaaca atacctgccc agaaagacgg gaaagaggag      60
gaaaaattcc tctttccacc aggaattctc tgggaagcac ataggatttc acgctactag     120
tttattccca agagaagcta ccaaagcttg gtaactacca actcttaact tttgtgtctc     180
taagtacact tctcctggga ttacaacaaa ttgaaccagg gatttaacgg aatctcagag     240
gaccgtaaga agaatgcttc gaggccgatc cctgtctgta acatccctga gtgggctgcc     300
ccggtgggaa gtcaaagaac ttcctgtgga ggagttactg ctctttgaag ttgcttggga     360
ggtgaccaat aaagttggag gcatctatac tgtgattcag acaaaggcca aaacaacagc     420
agatgaatgg ggagacaact atttctgat aggtccatat tttgagcata atatgaagac     480
tcaggtggaa caatgtgaac ctgtaaatga tgctgtcaga agagcagtgg atgcaatgaa     540
taagcatggc tgccaggtgc atttggaag atggctgata gaaggaagtc cttatgtggt     600 acttttgac ataggctttt cagcttggaa tctggatagg tggaagggtg acctctggga     660
agcatgcagt gtcggcattc cttatcatga ccgagaagcc aatgtatagc tgatatttgg     720
atctttaact gcctggttct taaaagaggt gacagatcac gcagatgata aacatgtcgt     780
```

```
tgcccaattc catgaatggc aggctggaat tggactgatc ctttctcgag ccaggaaact    840
tcctattgcc acaatattta caacccacgc tacactactc gggaggtatc tctgtgcagc    900
aaatattgat ttctacaacc atcttgataa gtttaacata gacaaagagg ctggggaaag    960
gcagatttac caccggtact gcatggagcg agcctccgtt cattgcgctc atgtgttcac   1020
cacggtttct gaaataacag caatagaggc cgaacacatg ctgaagagaa agcctgatgt   1080
agttactcca aatggcttga atgttaagaa attttcagca gtgcatgagt ttcaaaatct   1140
acatgccatg tacaaggcca gaatccaaga ttttgttcga ggtcatttct atggtcatct   1200
ggactttgat cttgaaaaga ctttgttcct tttcattgct gggagatatg agttttcaaa   1260
caaaggagct gacatcttcc tagaatcctt atccaggcta aatttcctgc tgaggatgca   1320
taaaagtgac gtcacagtgg tggtgttttt cattatgcct gccaagacaa ataatttcaa   1380
cgtggaaacc ctgaaaggac aagcagtgcg aaaacaactg tgggacattg cacattctgt   1440
gaaggaaaag tttggaaaaa aactctatga tgcattatta agaggagaaa ttcctgacat   1500
gaacaatatt ttagatcgag atgatctaac aattatgaaa gagccatctc tttcaactca   1560
gcgacagtca ttgcccccag tgaccacgca caacatgatt gatgactcca ccgaccccat   1620
cctcagcacc attagacgga tcggactttt caacaaccgc acagacagag tcaaggtgat   1680
tttgcacccg gaatttctat cctccaccag tcccctacta cccatggact atgaagagtt   1740
cgtcagaggt tgtcaccttg gagtatttcc atcatactat gaaccctggg ttatactcc    1800 agctgaatgc acagtgatgg gtatccccag tgtgaccacg aatctctccg ggtttggctg   1860
tttcatgcag gagcatgtgg ctgatcctac tgcttacggt atttacatcg ttgacaggcg   1920
gttccgttct ccagatgatt cttgcaatca gctgactcag tttctttatg gattttgcaa   1980
acagtcacgc cgccaaagga ttatccgaga gaacagaact gagaggctct cagatcttct   2040
ggattggaga tacttaggca gatattacca gcatgccaga cacctgacat taagcagagc   2100 tttttccagat aaattccatg tggaactaac atcaccacca atgacagaag gatttaaata   2160
tcccaggcct tcctcagtac caccttctcc ttcagggtct caggcctcca gtcctcagag   2220
cagtgatgtg gaagacgaag tggaggatga gagatacgat gaggaaaagg aggctgaaag   2280
ggatcggtta aatatcaagt caccatttgc actgagccac gttcctcgtg ggaagaaaaa   2340
gctgcatggt gaatataaga actgaattct acatgtgctg agaagagcta atttcataaa   2400
gcaaagtaag actaattatt taaaataaaa atgccacaca tttcattttc tccttctaag   2460
tattacaatg gaatttatta tctgcctaaa aagtggaaga aattgagtga atgacaattt   2520
cataatttag aataagatcc aagttgtttt ccccaactct tgttttcccc gtaaaagtta   2580
ggcatgagga ggagcactca ttaaaggcag aagatggaaa agtgttttta aaatggtgaa   2640
tttaagtggt aaggattttc tcttactctg tttattttta aattatcacc ataatccttt   2700
gcttactatt tatgcagctt ctctacccca ccacacaaat ttctcatttc cctctgaaaa   2760
ccttgatctt tcccatgaat gtgcactacc tacatatttt aaatagctag atttttactg   2820
attattttca tttttcacat gcatcagaac catgatttat atgtagtgtt gcagagacaa   2880
aatccatgtg tgaacagcta tcctaagttc atattttgat gcatactaat gcacatttat   2940
gtcacttttg aactctagaa tttatgttgt aattaatgga agatattatc atgtgaatgg   3000
aagatattac catgtgcatg gtaccaacat cttactgtaa catttttcta ttgtttaaat   3060
agaaagactt taaaaaaatt tggtcaatct tcatagatga taagttgtta aatcccagta   3120
aataaatgca ttaatatttta ataacttaa                                    3149
```

<210> SEQ ID NO 611
<211> LENGTH: 2671
<212> TYPE: DNA
<213> ORGANISM: Mus musculus

<400> SEQUENCE: 611

| | | | | | |
|---|---|---|---|---|---|
| tcatgctcag | tctgtcctct | ggctacctgc | cctgctgtga | atagtcaggt | ttcagctgcg | 60 |
| atttttgtt | ttgttttgtc | ttgttttttt | tgttttggg | tgtctgtgtg | gattataact | 120 |
| gtgaggcact | gccctctcct | gaaaggcagc | aaggagctgg | gcacgcttca | tccagctgcg | 180 |
| ctgggttcat | gtgacctcag | attgctggct | caccctgtag | aggctatccc | aaggctgctg | 240 |
| cttttctca | gtgctgactg | cagtcagctg | aatcaggtcc | caaacggcac | cacacagctg | 300 |
| gaagaagaat | gctcagaggc | cgctccttgt | cggtgacatc | ccttggtggg | ctccctgtgt | 360 |
| gggaagctga | aagactccct | gtggaagact | tactgcttt | tgaagtttct | tgggaggtga | 420 |
| ccaacaaagt | tggggcatc | tgtactgtga | tccagaccaa | ggccaaaacg | acagccgatg | 480 |
| agtggggaga | gaattacttc | ctgataggtc | cgtactttga | gcataatatg | aagactcaag | 540 |
| tagaacaatg | tgagcccacc | aacgatgctg | tcagaaaagc | tgtggatgcg | atgaataaac | 600 |
| atggctgcca | ggtgcatttt | ggaagatggc | tcatagaagg | gagtccctac | gtggtgctct | 660 |
| ttgacatcag | ctcctcagca | tggaacctgg | acagatggaa | gggtgacttc | tgggaagctt | 720 |
| gtggcgttgg | catccctcat | catgaccgag | aagctaacga | catgctcata | tttgggtctt | 780 |
| taactgcctg | gttcttaaag | gaggtgacag | accacgcaga | cggtaaacac | gtcattgccc | 840 |
| aattccatga | atggcaggct | gggactgggc | tgatcctttc | tcgtgccagg | aaactcccca | 900 |
| ttgccacagt | atttacaacc | catgccacac | tgcttgggcg | ttatctctgt | gcagcaaata | 960 |
| ttgacttcta | caaccagctt | gacaagttcg | acattgacaa | agaggccggg | gagaggcaga | 1020 |
| tataccaccg | ctactgcatg | gagcgggcat | ccgtgcactg | tgcgcacgtg | ttcaccacag | 1080 |
| tgtcagaaat | cacagccatc | gaggcagagc | acatgctgaa | gaggaagcct | gatgtagtga | 1140 |
| ctccaaatgg | tttgaatgtt | aagaagtttt | ctgcagtgca | tgaatttcaa | aatctccacg | 1200 |
| ccatgtacaa | ggccaggata | caggatttcg | ttcgaggtca | tttctatggt | catctggact | 1260 |
| ttgatcttga | aagacttta | tttcctcttca | ttgctgggag | atatgaattc | tcaaacaaag | 1320 |
| gagcagacat | cttcctggag | tccttatcca | ggcttaattt | cctcctgagg | atgcataaga | 1380 |
| gtaacgtcac | cgtggtagtg | tttttcatca | tgcctgccaa | gacaaacaat | tcaacgtgg | 1440 |
| aaaccctgaa | gggccaggca | gtgcggaaac | agctgtggga | cactgtgcat | tgtttgaagg | 1500 |
| agaagtttgg | gaagaaactc | tatgacgggt | tattaagagg | agaaattcct | gacatgaata | 1560 |
| gtattttgga | tcgagatgac | ttaacaatta | tgaaaagggc | catttttca | actcagagac | 1620 |
| agtctttgcc | tcctgtgacc | actcacaata | tgatcgatga | ttccacggat | cccatcctca | 1680 |
| gcaccattag | acgaatcgga | cttttcaaca | atcgtgcaga | cagagtcaag | gtgatttac | 1740 |
| acccagaatt | cctgtcctcc | accagccctc | tattgcccat | ggattatgaa | agtttgtcc | 1800 |
| gaggttgtca | ccttggggtg | tttccatcgt | actatgaacc | ctgggttac | acaccagctg | 1860 |
| aatgcacagt | gatgggcatc | cccagtgtga | ctacaaacct | ctccggtttt | gggtgtttcg | 1920 |
| tgcaggagca | tgtggctgac | cctactgcat | acggtattta | catcgtggac | agacgcttcc | 1980 |
| gctctccaga | cgattcttgc | aaccagctga | ctcagttcct | ctacggggttt | tgtaaacagt | 2040 |
| cacgccggca | aaggatcatt | cagaggaacc | gcacggagag | gctctcagat | ctcctggact | 2100 |

```
ggagatacct gggcagatat taccagcatg ccagacacct gacactgagc agggcttttc    2160
cagacaaatt ccacctagag cccacatcac caccaacgac ggatggcttt aagtatccca    2220
ggccctcctc agtaccacct tctccgtcag gatcccaggc ctccagtcct cagtgcagtg    2280
atgcggaaga cgaagaagat gaggatgaga ggtatgatga ggaagaggag gctgagaggg    2340
atcggctaaa tatcaagtca ccgttttctc tgaaccactt tccaaggggg aagaaaaagc    2400
ttcatggaga atataagaac tgactgagct caaacgaaat gattcagaat ccacaagaaa    2460
atgagctgcc ccaagtccac accctgatgc agaccaacag atatttacat cctgacatct    2520
gaaatctaga atttgtatcc agatcattga taggaacttg tagccaccaa tgtgagtcac    2580
cttactgtaa cggtactttt gttgtctaat tggaaatttc aatctgttag agataataaa    2640
ttgccaaatt caaatgaaaa aaaaaaaaa a                                    2671
```

<210> SEQ ID NO 612
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 612
ugggagguau gaguuuucaa gcagccgaaa ggcugc    36

<210> SEQ ID NO 613
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 613
aggaaaaguu uggaaaaaaa gcagccgaaa ggcugc    36

<210> SEQ ID NO 614
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 614
uggucaaucu ucauagauga gcagccgaaa ggcugc    36

<210> SEQ ID NO 615
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 615
gguuucugaa auaacagcaa gcagccgaaa ggcugc    36

<210> SEQ ID NO 616
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 616
gugaauauaa gaacugaauu gcagccgaaa ggcugc    36

<210> SEQ ID NO 617
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 617
auugagugaa ugacaauuuu gcagccgaaa ggcugc                                36

<210> SEQ ID NO 618
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 618
aaugacaauu uuguaauuua gcagccgaaa ggcugc                                36

<210> SEQ ID NO 619
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 619
gaauugaugu uguaauuaau gcagccgaaa ggcugc                                36

<210> SEQ ID NO 620
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 620
uugaaaacuc auaccuccca gg                                               22

<210> SEQ ID NO 621
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 621
uuuuuuucca aacuuuuccu gg                                               22

<210> SEQ ID NO 622
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 622
ucaucuauga agauugacca gg                                               22

<210> SEQ ID NO 623
<211> LENGTH: 22
<212> TYPE: RNA
<213> ORGANISM: Artificial Sequence
<220> FEATURE:

```
<223> OTHER INFORMATION: Synthetic Polynucleotide

<400> SEQUENCE: 623
uugcuguuau uucagaaacc gg                                              22

<210> SEQ ID NO 624
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 624
aauucaguuc uuauauucac gg                                              22

<210> SEQ ID NO 625
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 625
aaaauuguca uucacucaau gg                                              22

<210> SEQ ID NO 626
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 626
uaaauuacaa aauugucauu gg                                              22

<210> SEQ ID NO 627
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 627
auuaauuaca acaucaauuc gg                                              22
```

US 11,572,562 B2

COMPOSITIONS AND METHODS FOR INHIBITING GYS2 EXPRESSION

RELATED APPLICATION

This application claims the benefit under 35 U.S.C. § 119(e) to U.S. Provisional Application No. 62/637,574, filed Mar. 2, 2018, and entitled "COMPOSITIONS AND METHODS FOR INHIBITING GYS2 EXPRESSION," the entire contents of which are incorporated herein by reference.

FIELD OF THE INVENTION

The present application relates to oligonucleotides and uses thereof, particularly uses relating to the treatment of glycogen storage diseases and associated conditions.

REFERENCE TO THE SEQUENCE LISTING

The present application is being filed along with a Sequence Listing in electronic format. The Sequence Listing is provided as a file entitled D0800.70014WO00-SEQ.txt created on Feb. 15, 2019 which is 132 kilobytes in size. The information in electronic format of the sequence listing is incorporated herein by reference in its entirety.

BACKGROUND OF THE INVENTION

Glycogen is a complex sugar used by the body to store glucose. When the body requires more glucose to function, it normally breaks down the stored glycogen for use in cellular processes. Several enzymes participate in the processes that are used to store glucose as glycogen (glycogen synthesis) and break down glycogen to glucose (glycogen breakdown). When one or more of these enzymes are inhibited, it can result in a glycogen storage disease in which a dearth of glycogen storage, a buildup of glycogen in affected cells (e.g., liver and/or muscle cells), or the formation of abnormally structured glycogen may be observed. When a disorder of glycogen storage or breakdown occurs, those affected may suffer from a number of symptoms including, but not limited to: hepatomegaly, increased liver toxicity (e.g., higher levels of AST, ALT, and/or ALP), liver fibrosis, fatty acid deposition in the liver, hepatic hyperplasia, hepatocellular adenoma, and/or hepatocellular carcinoma. A non-limiting set of exemplary glycogen storage diseases may include: GSDI (e.g., GSDIa), GSDIII, GSDIV, GSDVI, and GSDIX.

BRIEF SUMMARY OF THE INVENTION

Aspects of the disclosure relate to oligonucleotides and related methods for treating a glycogen storage disease (e.g., a disease or disorder affecting glycogen breakdown or storage such as GSDIa, GSDIII, GSDIV, GSDVI, or GSDIX) in a subject. In some embodiments, potent RNAi oligonucleotides have been developed for selectively inhibiting GYS2 expression in a subject. In some embodiments, the RNAi oligonucleotides are useful for reducing overall GYS2 activity in hepatocytes, and thereby decreasing or preventing hepatomegaly, liver toxicity (e.g., levels of AST, ALT, and/or ALP), liver fibrosis, fatty acid deposition in the liver, hepatic hyperplasia, hepatocellular adenoma, and/or hepatocellular carcinoma. In some embodiments, key regions of GYS2 mRNA (referred to as hotspots) have been identified herein that are particularly amenable to targeting using such oligonucleotide-based approaches (See, e.g., Example 1).

One aspect of the present disclosure provides oligonucleotides for reducing expression of GYS2. In some embodiments, the oligonucleotides comprise an antisense strand comprising a sequence as set forth in any one of SEQ ID NOs: 193-384, 417-466, 518-568, 575-580, 586-598, or 620-627. In some embodiments, the antisense strand consists of a sequence as set forth in any one of SEQ ID NOs: 193-384, 417-466, 518-568, 575-580, 586-598, or 620-627. In some embodiments, the antisense strand comprises, or consists of, a sequence as set forth in any one of SEQ ID NOs: 417-466, 575-580, 586-598, 620-627. In some embodiments, the oligonucleotides further comprise a sense strand that comprises a sequence as set forth in any one of SEQ ID NOs: 1-192, 385-416, 467-517, 569-574, 581-585, or 612-619. In some embodiments, the sense strand consists of a sequence as set forth in any one of SEQ ID NOs: 1-192, 385-416, 467-517, 569-574, 581-585, or 612-619. In some embodiments, the sense strand comprises, or consists of, a sequence as set forth in any one of SEQ ID NOs: 385-416, 569-574, 581-585, 612-619.

One aspect of the present disclosure provides oligonucleotides for reducing expression of GYS2, in which the oligonucleotides comprise an antisense strand of 15 to 30 nucleotides in length. In some embodiments, the antisense strand has a region of complementarity to a target sequence of GYS2 as set forth in any one of SEQ ID NOs: 599-608. In some embodiments, the region of complementarity is at least 15, at least 16, at least 17, at least 18, at least 19, at least 20, at least 21, or at least 22 contiguous nucleotides in length. In some embodiments, the region of complementarity is fully complementary to the target sequence of GYS2. In some embodiments, the region of complementarity to GYS2 is at least 19 contiguous nucleotides in length.

In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the antisense strand is 27 nucleotides in length and the sense strand is 25 nucleotides in length. In some embodiments, the duplex region is at least 15, at least 16, at least 17, at least 18, at least 19, at least 20, or at least 21 nucleotides in length. In some embodiments, the antisense strand and sense strand form a duplex region of 25 nucleotides in length.

In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide further comprises a 3'-overhang sequence on the antisense strand of two nucleotides in length. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

In some embodiments, the sense strand comprises a sequence as set forth in any one of SEQ ID NOs: 1-192, 385-416, 467-517, 569-574, 581-585, or 612-619. In some embodiments, the sense strand consists of a sequence as set forth in any one of SEQ ID NOs: 1-192, 385-416, 467-517, 569-574, 581-585, or 612-619. In some embodiments, the antisense strand comprises a sequence as set forth in any one of SEQ ID NOs: 193-384, 417-466, 518-568, 575-580, 586-598, or 620-627. In some embodiments, the antisense strand consists of a sequence as set forth in any one of SEQ ID NOs: 193-384, 417-466, 518-568, 575-580, 586-598, or 620-627.

In some embodiments, the sense strand comprises at its 3'-end a stem-loop set forth as: S1-L-S2, in which S1 is complementary to S2, and in which L forms a loop between S1 and S2 of 3 to 5 nucleotides in length.

Another aspect of the present disclosure provides an oligonucleotide for reducing expression of GYS2, the oligonucleotide comprising an antisense strand and a sense strand, in which the antisense strand is 21 to 27 nucleotides in length and has a region of complementarity to GYS2, in which the sense strand comprises at its 3'-end a stem-loop set forth as: S1-L-S2, in which S1 is complementary to S2, and in which L forms a loop between S1 and S2 of 3 to 5 nucleotides in length, and in which the antisense strand and the sense strand form a duplex structure of at least 19 nucleotides in length but are not covalently linked (see, e.g., FIG. 3). In some embodiments, the region of complementarity is fully complementary to at least 15, at least 16, at least 17, at least 18, at least 19, at least 20, or at least 21 contiguous nucleotides of GYS2 mRNA. In some embodiments, L is a tetraloop. In some embodiments, L is 4 nucleotides in length. In some embodiments, L comprises a sequence set forth as GAAA.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in a decreased level or prevention of hepatomegaly, liver nodule formation, liver toxicity (e.g., levels of AST, ALT, and/or ALP), liver fibrosis, hepatocellular proliferation, fatty acid deposition in the liver, hepatic hyperplasia, hepatocellular adenoma, and/or hepatocellular carcinoma. Another aspect of the present disclosure provides a method for treating a glycogen storage disease or one or more symptoms of a glycogen storage disease. A non-limiting set of exemplary glycogen storage diseases may include: GSDI (e.g., GSDIa), GSDIII, GSDIV, GSDVI, and GSDIX.

Another aspect of the present disclosure provides an oligonucleotide for reducing expression of GYS2, the oligonucleotide comprising a sense strand of 15 to 40 nucleotides in length and an antisense strand of 15 to 30 nucleotides in length, in which the sense strand forms a duplex region with the antisense strand, in which the sense strand comprises a sequence as set forth in any one of SEQ ID NOs: 1-192, 385-416, 467-517, 569-574, 581-585, or 612-619, and results in a the antisense strand comprises a complementary sequence selected from SEQ ID NOs: 193-384, 417-466, 518-568, 575-580, 586-598, or 620-627.

In some embodiments, the oligonucleotide comprises a pair of sense and antisense strands selected from a row of the table set forth in Table 4.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIGS. 1A and 1B are graphs showing the percentage of GYS2 mRNA remaining after a screen of 264 GYS2 conjugates in HEK-293 cells. The nucleotide position in NM_021957.3 that corresponds to the 3' end of the sense strand of each siRNA is indicated on the x axis.

DETAILED DESCRIPTION OF THE INVENTION

Figure 1A:
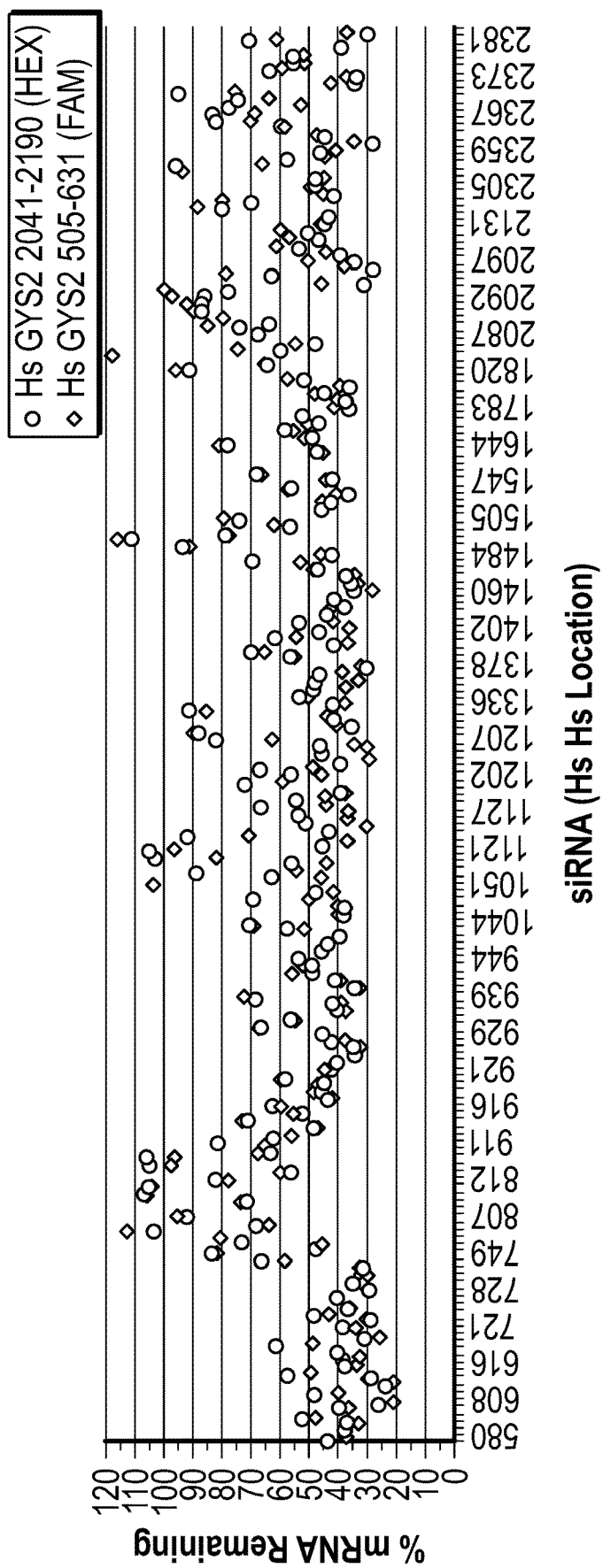

According to some aspects, the disclosure provides oligonucleotides targeting GYS2 mRNA that are effective for reducing GYS2 expression in cells, particularly liver cells (e.g., hepatocytes) for the treatment of a glycogen storage disease (e.g., GSDIa, GSDIII, GSDIV, GSDVI, and GSDIX) or one or more symptoms of a glycogen storage disease. Accordingly, in related aspects, the disclosure provided methods of treating a glycogen storage disease (e.g., GSDIa, GSDIII, GSDIV, GSDVI, and GSDIX) or one or more symptoms of a glycogen storage disease that involve selectively reducing GYS2 gene expression in liver. In certain embodiments, GYS2 targeting oligonucleotides provided herein are designed for delivery to selected cells of target tissues (e.g., liver hepatocytes) to treat a glycogen storage disease (e.g., GSDIa, GSDIII, GSDIV, GSDVI, and GSDIX) or one or more symptoms of a glycogen storage disease in a subject.

Further aspects of the disclosure, including a description of defined terms, are provided below.

I. Definitions

Administering: As used herein, the terms "administering" or "administration" means to provide a substance (e.g., an oligonucleotide) to a subject in a manner that is pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Complementary: As used herein, the term "complementary" refers to a structural relationship between nucleotides (e.g., two nucleotide on opposing nucleic acids or on opposing regions of a single nucleic acid strand) that permits the nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have nucleotide sequences that are complementary to each other so as to form regions of complementarity, as described herein.

Deoxyribonucleotide: As used herein, the term "deoxyribonucleotide" refers to a nucleotide having a hydrogen at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Glycogen Storage Disease: As used herein, the term "glycogen storage disease," "GSD," or "glycogen storage diseases" refers to metabolic disorders caused by enzyme deficiencies affecting glycogen synthesis, glycogen breakdown, and/or glucose breakdown (glycolysis). Various types of glycogen storage diseases have been characterized, including GSD 0, GSD I (also known as GSD 1 or von Gierke's disease; e.g., GSDIa), GSD II (also known as Pompe disease or acid maltase deficiency disease), GSD III (also known as GSD 3, Cori's disease, or Forbes' disease), GSD IV (GSD 4 or Andersen disease), GSD V (also known as McArdle disease), GSD VI (also known as GSD 6 or Hers' disease), GSD VII (also known as GSD 7 or Tarui's disease), GSD VIII, and GSD IX (also known as GSD 9). In some embodiments, individuals having a glycogen storage disease exhibit one or more of a number of symptoms including, but not limited to: hepatomegaly, increased liver toxicity (e.g., higher levels of AST, ALT, and/or ALP), liver fibrosis, fatty acid deposition in the liver, hepatic hyperplasia, hepatocellular adenoma, and/or hepatocellular carcinoma.

GYS2: as used herein, the term "GYS2" or "glycogen synthase 2" refers to the liver glycogen synthase gene. This gene encodes a protein, liver glycogen synthase, that catalyzes a rate-limiting stem in the synthesis of glycogen (i.e., the transfer of a glucose molecule from UDP-glucose to a terminal branch of the glycogen molecule). GYS2 is expressed in liver cells, e.g., hepatocytes. Homologs of GYS2 are conserved across a range of species, including human, mouse, rat, non-human primate species, and others (see, e.g., NCBI HomoloGene: 56580.) In humans, GYS2 encodes multiple transcripts, namely as set forth in GenBank accession numbers NM_021957.3 (SEQ ID NO: 609), XM_006719063.3, and XM_017019245.1, each encoding a different isoform, GenBank accession numbers NP_068776.2, XP_006719126.1 (isoform X1) and XP 016874734.1 (isoform X2), respectively. An example monkey (Rhesus macaque) transcript sequence is set forth in GenBank accession number XM_001098578.2 (SEQ ID NO: 610). An example mouse transcript is set forth in GenBank accession number NM_145572.2 (SEQ ID NO: 611).

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. In certain embodiments, a modified nucleotide comprises a 2'-O-methyl or a 2'-F substitution at the 2' position of the ribose ring.

Nicked Tetraloop Structure: A "nicked tetraloop structure" is a structure of a RNAi oligonucleotide characterized by the presence of separate sense (passenger) and antisense (guide) strands, in which the sense strand has a region of complementarity to the antisense strand such that the two strands form a duplex, and in which at least one of the strands, generally the sense strand, extends from the duplex in which the extension contains a tetraloop and two self-complementary sequences forming a stem region adjacent to the tetraloop, in which the tetraloop is configured to stabilize the adjacent stem region formed by the self-complementary sequences of the at least one strand.

Oligonucleotide: As used herein, the term "oligonucleotide" refers to a short nucleic acid, e.g., of less than 100 nucleotides in length. An oligonucleotide can comprise ribonucleotides, deoxyribonucleotides, and/or modified nucleotides including, for example, modified ribonucleotides. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, International Patent Application PCT/US2017/049909, filed on Sep. 1, 2017, U.S. Provisional Application Nos. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to GYS2 mRNA sequence) may result in a decrease in the amount of RNA transcript, protein and/or enzymatic activity (e.g., encoded by the GYS2 gene) compared to a cell that is not treated with the double-stranded oligonucleotide. Similarly, "reducing expression" as used herein refers to an act that results in reduced expression of a gene (e.g., GYS2).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides (e.g., a target nucleotide sequence within an mRNA) to permit hybridization between the two sequences of nucleotides under appropriate hybridization conditions, e.g., in a phosphate buffer, in a cell, etc. A region of complementarity may be fully complementary to a nucleotide sequence (e.g., a target nucleotide sequence present within an mRNA or portion thereof). For example, a region of complementarity that is fully complementary to a nucleotide sequence present in an mRNA has a contiguous sequence of nucleotides that is complementary, without any mismatches or gaps, to a corresponding sequence in the mRNA. Alternatively, a region of complementarity may be partially complementary to a nucleotide sequence (e.g., a nucleotide sequence present in an mRNA or portion thereof). For example, a region of complementary that is partially complementary to a nucleotide sequence present in an mRNA has a contiguous sequence of nucleotides that is complementary to a corresponding sequence in the mRNA but that contains one or more mismatches or gaps (e.g., 1, 2, 3, or more mismatches or gaps) compared with the corresponding sequence in the mRNA, provided that the region of complementarity remains capable of hybridizing with the mRNA under appropriate hybridization conditions.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C., or at least 75° C. in 10 mM $NaHPO_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include, but are not limited to: non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine) or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors i. GYS2 Targeting Oligonucleotides

Potent oligonucleotides have been identified herein through examination of the GYS2 mRNA, including mRNAs of different species (human and Rhesus macaque, (see, e.g., Example 1)) and in vitro and in vivo testing. Such oligonucleotides can be used to achieve therapeutic benefit for subjects with a glycogen storage disease (e.g., GSDIa, GSDIII, GSDIV, GSDVI, and GSDIX) or one or more symptoms of a glycogen storage disease by reducing GYS2 activity, and consequently, by decreasing or preventing hepatomegaly, liver toxicity (demonstrated, e.g., levels of AST, ALT, and/or ALP), liver fibrosis, fatty acid deposition in the liver, hepatic hyperplasia, hepatocellular adenoma, and/or hepatocellular carcinoma. For example, potent RNAi oligonucleotides are provided herein that have a sense strand comprising, or consisting of, a sequence as set forth in any one of SEQ ID NOs: 1-192, 385-416, 467-517, 569-574, 581-585, or 612-619, and an antisense strand comprising, or consisting of, a complementary sequence selected from SEQ ID NOs: 193-384, 417-466, 518-568, 575-580, 586-598, or 620-627, as is also arranged the table provided in Table 4 (e.g., a sense strand comprising a sequence as set forth in SEQ ID NO: 1 and an antisense strand comprising a sequence as set forth in SEQ ID NO: 193).

The sequences can be put into multiple different oligonucleotide structures (or formats) as described herein.

In some embodiments, it has been discovered that certain regions of GYS2 mRNA are hotspots for targeting because they are more amenable than other regions to oligonucleotide-based inhibition. In some embodiments, a hotspot region of GYS2 consists of a sequence as forth in any one of SEQ ID NOs: 599-608. These regions of GYS2 mRNA may be targeted using oligonucleotides as discussed herein for purposes of inhibiting GYS2 mRNA expression.

Accordingly, in some embodiments, oligonucleotides provided herein are designed so as to have regions of complementarity to GYS2 mRNA (e.g., within a hotspot of GYS2 mRNA) for purposes of targeting the mRNA in cells and inhibiting its expression. The region of complementarity is generally of a suitable length and base content to enable annealing of the oligonucleotide (or a strand thereof) to GYS2 mRNA for purposes of inhibiting its expression.

In some embodiments, an oligonucleotide disclosed herein comprises a region of complementarity (e.g., on an antisense strand of a double-stranded oligonucleotide) that is at least partially complementary to a sequence as set forth in SEQ ID NOs: 1-192, 385-416, 467-517, 569-574, 581-585, or 612-619, which include sequences mapping to within hotspot regions of GYS2 mRNA. In some embodiments, an oligonucleotide disclosed herein comprises a region of complementarity (e.g., on an antisense strand of a double-stranded oligonucleotide) that is fully complementary to a sequence as set forth in SEQ ID NOs: 1-192, 385-416, 467-517, 569-574, 581-585, or 612-619. In some embodiments, a region of complementarity of an oligonucleotide that is complementary to contiguous nucleotides of a sequence as set forth in SEQ ID NOs: 1-192, 385-416, 467-517, 569-574, 581-585, or 612-619 spans the entire length of an antisense strand. In some embodiments, a region of complementarity of an oligonucleotide that is complementary to contiguous nucleotides of a sequence as set forth in any one of SEQ ID NOs: 1-192, 385-416, 467-517, 569-574, 581-585, or 612-619 spans a portion of the entire length of an antisense strand (e.g., all but two nucleotides at the 3' end of the antisense strand). In some embodiments, an oligonucleotide disclosed herein comprises a region of complementarity (e.g., on an antisense strand of a double-stranded oligonucleotide) that is at least partially (e.g., fully) complementary to a contiguous stretch of nucleotides spanning nucleotides 1-19 of a sequence as set forth in SEQ ID NOs: 1-192, 385-416, 467-517, 569-574, 581-585, or 612-619.

In some embodiments, the region of complementarity is at least 12, at least 13, at least 14, at least 15, at least 16, at least 17, at least 18, at least 19, at least 20, at least 21, at least 22, at least 23, at least 24, or at least 25 nucleotides in length. In some embodiments, an oligonucleotide provided herein has a region of complementarity to GYS2 mRNA that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to GYS2 mRNA that is 12, 13, 14, 15, 16, 17, 18, 19, 20, 21, 22, 23, 24, 25, 26, 27, 28, 29, or 30 nucleotides in length.

In some embodiments, a region of complementarity to GYS2 mRNA may have one or more mismatches compared with a corresponding sequence of GYS2 mRNA. A region of complementarity on an oligonucleotide may have up to 1, up to 2, up to 3, up to 4 etc. mismatches provided that it maintains the ability to form complementary base pairs with GYS2 mRNA under appropriate hybridization conditions. Alternatively, a region of complementarity on an oligonucleotide may have no more than 1, no more than 2, no more than 3, or no more than 4 mismatches provided that it maintains the ability to form complementary base pairs with GYS2 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with GYS2 mRNA under appropriate hybridization conditions.

Still, in some embodiments, double-stranded oligonucleotides provided herein comprise, or consist of, a sense strand having a sequence as set forth in any one of SEQ ID NOs: 1-192, 385-416, 467-517, 569-574, 581-585, or 612-619 and an antisense strand having a complementary sequence selected from SEQ ID NOs: 193-384, 417-466, 518-568, 575-580, 586-598, or 620-627, as is arranged in the table provided in Table 4 (e.g., a sense strand comprising a sequence as set forth in SEQ ID NO: 1 and an antisense strand comprising a sequence as set forth in SEQ ID NO: 193).

ii. Oligonucleotide Structures

There are a variety of structures of oligonucleotides that are useful for targeting GYS2 mRNA in the methods of the present disclosure, including RNAi, miRNA, etc. Any of the structures described herein or elsewhere may be used as a framework to incorporate or target a sequence described herein (e.g., a hotpot sequence of GYS2 such as those illustrated in SEQ ID NOs: 599-608, or a sense or antisense strand that comprises or consists of a sequence as set forth SEQ ID NOs: 1-192, 385-416, 467-517, 569-574, 581-585, or 612-619 or as set forth SEQ ID NOs: 193-384, 417-466, 518-568, 575-580, 586-598, or 620-627, respectively). Double-stranded oligonucleotides for targeting GYS2 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, sequences described herein can be incorporated into, or targeted using, oligonucleotides that comprise sense and antisense strands that are both in the range of 17 to 40 nucleotides in length. In some embodiments, oligonucleotides incorporating such sequences are provided that have a tetraloop structure within a 3' extension of their sense strand, and two terminal overhang nucleotides at the 3' end of its antisense strand. In some embodiments, the two terminal overhang nucleotides are GG. Typically, one or both of the two terminal GG nucleotides of the antisense strand is or are not complementary to the target.

In some embodiments, oligonucleotides incorporating such sequences are provided that have sense and antisense strands that are both in the range of 21 to 23 nucleotides in length. In some embodiments, a 3' overhang is provided on the sense, antisense, or both sense and antisense strands that is 1 or 2 nucleotides in length. In some embodiments, an oligonucleotide has a guide strand of 23 nucleotides and a passenger strand of 21 nucleotides, in which the 3'-end of passenger strand and 5'-end of guide strand form a blunt end and where the guide strand has a two nucleotide 3' overhang.

In some embodiments, double-stranded oligonucleotides for reducing GYS2 expression engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, oligonucleotides may be in the range of 21 to 23 nucleotides in length. In some embodiments, oligonucleotides may have an overhang (e.g., of 1, 2, or 3 nucleotides in length) in the 3' end of the sense and/or antisense strands. In some embodiments, oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. See, for example, U.S. Pat. Nos. 9,012,138, 9,012,621, and 9,193,753, the contents of each of which are incorporated herein for their relevant disclosures.

In some embodiments, an oligonucleotide of the invention has a 36 nucleotide sense strand that comprises an region extending beyond the antisense-sense duplex, where the extension region has a stem-tetraloop structure where the stem is a six base pair duplex and where the tetraloop has four nucleotides. In some embodiments, the stem-tetraloop is set forth as: $S_1$-L-$S_2$, in which $S_1$ is complementary to $S_2$ so as to form a duplex, and in which L forms a tetraloop between $S_1$ and $S_2$.

In certain of those embodiments, three or four of the tetraloop nucleotides are each conjugated to a monovalent GalNac ligand.

In some embodiments, an oligonucleotide of the invention comprises a 25 nucleotide sense strand and a 27 nucleotide antisense strand that when acted upon by a dicer enzyme results in an antisense strand that is incorporated into the mature RISC.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of GYS2 are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, an oligonucleotide disclosed herein for targeting GYS2 comprises an antisense strand comprising or consisting of a sequence as set forth in any one of SEQ ID NOs: 193-384, 417-466, 518-568, 575-580, 586-598, or 620-627. In some embodiments, an oligonucleotide comprises an antisense strand comprising or consisting of at least 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 193-384, 417-466, 518-568, 575-580, 586-598, or 620-627.

In some embodiments, a double-stranded oligonucleotide may have an antisense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least 12 nucleotides in length (e.g., at least 12, at least 15, at least 19, at least 21, at least 22, at least 25, at least 27, at least 30, at least 35, or at least 38 nucleotides in length). In some embodiments, an oligonucleotide may have an antisense strand in a range of 12 to 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide disclosed herein for targeting GYS2 comprises or consists of a sense strand sequence as set forth in in any one of SEQ ID NOs: 1-192, 385-416, 467-517, 569-574, 581-585, or 612-619. In some embodiments, an oligonucleotide has a sense strand that comprises or consists of at least 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 1-192, 385-416, 467-517, 569-574, 581-585, or 612-619.

In some embodiments, an oligonucleotide may have a sense strand (or passenger strand) of up to 40 nucleotides in length (e.g., up to 40, up to 36, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 36, or at least 38 nucleotides in length). In some embodiments, an oligonucleotide may have a sense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, a sense strand comprises a stem-loop structure at its 3'-end. In some embodiments, a sense strand comprises a stem-loop structure at its 5'-end. In some embodiments, a stem is a duplex of 2, 3, 4, 5, 6, 7, 8, 9, 10, 11, 12, 13, or 14 base pairs in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30, or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide provided herein comprises sense and antisense strands, such that there is a 3'-overhang on either the sense strand or the antisense strand, or both the sense and antisense strand. In some embodiments, oligonucleotides provided herein have one 5'end that is thermodynamically less stable compared to the other 5' end. In some embodiments, an asymmetric oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7, or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary to the target. In some embodiments, the last one or two nucleotides at the 3' end of the antisense strand are not complementary to the target. In some embodiments, the 5' end and/or the 3' end of a sense or antisense strand has an inverted cap nucleotide.

e. Mismatches

In some embodiments, there is one or more (e.g., 1, 2, 3, or 4) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

iii. Single-Stranded Oligonucleotides

In some embodiments, an oligonucleotide for reducing GYS2 expression as described herein is single-stranded. Such structures may include, but are not limited to single-stranded RNAi oligonucleotides. Recent efforts have demonstrated the activity of single-stranded RNAi oligonucleotides (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier (e.g., "naked delivery"), it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every nucleotide is modified at the 2'-position of the sugar group of that nucleotide. These modifications may be reversible or irreversible. Typically, the 2'-position modification is 2'-fluoro, 2'-O-methyl, etc. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. In certain embodiments, the 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro, 2'-O-methyl, or 2'-O-methoxyethyl. However, a large variety of 2' position modifications that have been developed for use in oligonucleotides can be employed in oligonucleotides disclosed herein. See, e.g., Bramsen et al., Nucleic Acids Res., 2009, 37, 2867-2881. In some embodiments, a modification in a sugar comprises a modification of the sugar ring, which may comprise modification of one or more carbons of the sugar ring. For example, a modification of a sugar of a nucleotide may comprise a linkage between the 2'-carbon and a 1'-carbon or 4'-carbon of the sugar. For example, the linkage may comprise an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

5'-terminal phosphate groups of oligonucleotides may or in some circumstances enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, International Patent Application PCT/US2017/049909, filed on Sep. 1, 2017, U.S. Provisional Application Nos. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—CH$_2$—PO(OH)$_2$ or —O—CH$_2$—PO(OR)$_2$, in which R is independently selected from H, CH$_3$, an alkyl group, CH$_2$CH$_2$CN, CH$_2$OCOC(CH$_3$)$_3$, CH$_2$OCH$_2$CH$_2$Si(CH$_3$)$_3$, or a protecting group. In certain embodiments, the alkyl group is CH$_2$CH$_3$. More typically, R is independently selected from H, CH$_3$, or CH$_2$CH$_3$.

c. Modified Internucleoside Linkages

In some embodiments, the oligonucleotide may comprise a modified internucleoside linkage. In some embodiments, phosphate modifications or substitutions may result in an oligonucleotide that comprises at least one (e.g., at least 1, at least 2, at least 3, at least 4, or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., Nature Biotechnology, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. J. Am. Chem. Soc. 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., International Patent Application PCT/US2017/048239, which published on Mar. 1, 2018 as International Patent Publication WO2018/039364, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5, or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a targeting ligand, as described, for example, in International Patent Application Publication WO 2016/100401, which was published on Jun. 23, 2016, the relevant contents of which are incorporated herein by reference.

In some embodiments, it is desirable to target an oligonucleotide that reduces the expression of GYS2 to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5, or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable. In some embodiments, a duplex extension (up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of GYS2. Such compositions can be suitably formulated such that when administered to a subject, either into the immediate environment of a target cell or systemically, a sufficient portion of the oligonucleotides enter the cell to reduce GYS2 expression. Any of a variety of suitable oligonucleotide formulations can be used to deliver oligonucleotides for the reduction of GYS2 as disclosed herein. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS)

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing GYS2 expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing GYS2 Expression in Cells

In some embodiments, methods are provided for delivering to a cell an effective amount any one of oligonucleotides disclosed herein for purposes of reducing expression of GYS2 in the cell. Methods provided herein are useful in any appropriate cell type. In some embodiments, a cell is any cell that expresses GYS2 (e.g., liver cells such as hepatocytes or adipose cells). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of GYS2 solely or primarily in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of GYS2 expression (e.g., RNA, protein). In some embodiments, the extent to which an oligonucleotide provided herein reduces levels of expression of GYS2 is evaluated by comparing expression levels (e.g., mRNA or protein levels of GYS2 to an appropriate control (e.g., a level of GYS2 expression in a cell or population of cells to which an oligonucleotide has not been delivered or to which a negative control has been delivered). In some embodiments, an appropriate control level of GYS2 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of GYS2 expression in a cell. In some embodiments, the reduction in levels of GYS2 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of GYS2. The appropriate control level may be a level of GYS2 expression in a cell or population of cells that has not been contacted with an oligonucleotide as described herein. In some embodiments, the effect of delivery of an oligonucleotide to a cell according to a method disclosed herein is assessed after a finite period of time. For example, levels of GYS2 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing GYS2 expression for the treatment of a glycogen storage disease in a subject. In some embodiments, the methods may comprise administering to a subject in need thereof an effective amount of any one of the oligonucleotides disclosed herein. Such treatments could be used, for example, to decrease or prevent hepatomegaly, liver toxicity (e.g., lower or decrease levels of AST, ALT, and/or ALP), liver fibrosis, fatty acid deposition in the liver, hepatic hyperplasia, hepatocellular adenoma, and/or hepatocellular carcinoma. Such treatments could also be used, for example, to treat or prevent one or more symptoms associated with a glycogen storage disease selected from the list consisting of: GSDIa, GSDIII, GSDIV, GSDVI, and GSDIX, or to treat or prevent one or more symptoms of such a glycogen storage disease. The present disclosure provides for both prophylactic and therapeutic methods of treating a subject at risk of (or susceptible to) a glycogen storage disease (e.g., GSDIa, GSDIII, GSDIV, GSDVI, and GSDIX) and/or symptoms or conditions associated with a glycogen storage disease (e.g., GSDIa, GSDIII, GSDIV, GSDVI, and GSDIX).

In certain aspects, the disclosure provides a method for preventing in a subject, a disease, disorder, symptom, or condition as described herein by administering to the subject a therapeutic agent (e.g., an oligonucleotide or vector or transgene encoding same). In some embodiments, the subject to be treated is a subject who will benefit therapeutically from a reduction in the amount of GYS2 protein, e.g., in the liver.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intramuscular injection,), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

In some embodiments, oligonucleotides are administered at a dose in a range of 0.1 mg/kg to 25 mg/kg (e.g., 1 mg/kg to 5 mg/kg). In some embodiments, oligonucleotides are administered at a dose in a range of 0.1 mg/kg to 5 mg/kg or in a range of 0.5 mg/kg to 5 mg/kg.

As a non-limiting set of examples, the oligonucleotides of the instant disclosure would typically be administered once per year, twice per year, quarterly (once every three months), bi-monthly (once every two months), monthly, or weekly.

In some embodiments, the subject to be treated is a human (e.g., a human patient) or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Example 1: Development of GYS2 Oligonucleotide Inhibitors Using Human and Mouse Cell-Based Assays Human and mouse-based assays were used to develop candidate oligonucleotides for inhibition of GYS2 expression. First, a computer-based algorithm was used to generate candidate oligonucleotide sequences (25-27-mer) for GYS2 inhibition. Cell-based assays and PCR assays were then employed for evaluation of candidate oligonucleotides for their ability to reduce GYS2 expression.

The computer-based algorithm provided oligonucleotides that were complementary to the human GYS2 mRNA (SEQ ID NO: 609, Table 1), of which certain sequences were also complementary to the Rhesus macaque GYS2 mRNA (SEQ ID NO: 610, Table 1).

TABLE 1

Sequences of human and *Rhesus macaque* GYS2 mRNA

| Species | GenBank RefSeq # | SEQ ID NO. |
|---|---|---|
| Human | NM_021957.3 | 609 |
| *Rhesus macaque* | XM_001098578.2 | 610 |

Of the oligonucleotides that the algorithm provided, 264 oligonucleotides were selected as candidates for experimental evaluation in a HEK-293 cell-based assay. In this assay, HEK-293 human embryonic kidney cells stably expressing GYS2 (referred to as HEK-GYS2 cells) were transfected with the oligonucleotides. Cells were maintained for a period of time following transfection and then levels of remaining GYS2 mRNA were interrogated using TAQMAN®-based qPCR assays. Two qPCR assays, a 3' assay and a 5' assay, were used to determine mRNA levels as measured by HEX and FAM probes, respectively. The results of the HEK-293 cell-based assay with the 264 oligonucleotides are shown in FIGS. 1A and 1B. The percent mRNA remaining is shown for each of the 3' assay (circle shapes) and the 5' assay (diamond shapes). Oligonucleotides with the lowest percentage of mRNA remaining compared to negative controls were considered hits. Oligonucleotides with low complementarity to the human genome were used as negative controls.

Based on the activity and locations of these oligonucleotides, hotspots on the human GYS2 mRNA were defined. A hotspot was identified as a stretch on the human GYS2 mRNA sequence associated with at least two oligonucleotides resulting in mRNA levels that were less than or equal to 35% in either assay compared with controls. Accordingly, the following hotspots within the human GYS2 mRNA sequence were identified: 579-618, 691-738, 1089-1125, 1175-1211, 1431-1486, 2341-2383, 2497-2543, 2660-2698, 2808-2851, and 3014-3050.

The sequences of the hotspots are outlined in Table 2.

TABLE 2

Sequences of Hotspots

| Hotspot Position In Human GYS2 mRNA | Sequence | SEQ ID NO. |
|---|---|---|
| 579-618 | GATAGAAGGAAGTCCTTATGTGGTACTTTTTGACATAGGC | 599 |
| 691-738 | GACCGAGAAGCCAATGATATGCTGATATTTGGATCTTTAACTGCCTGG | 600 |
| 1089-1125 | TCCAAACGGCTTGAATGTTAAGAAATTTTCAGCAGTG | 601 |
| 1175-1211 | TTGTTCGAGGTCATTTCTATGGICATCTCGACTTTGA | 602 |
| 1431-1486 | TGCACATTCTGTGAAGGAAAAGTTTGGAAAAAAACTCTATGATGCATTATTAAGAG | 603 |
| 2341-2383 | AAGCTGCATGGTGAATATAAGAACTGAATTCTACATGTGCTGC | 604 |
| 2497-2543 | GTGGAAGAAATTGAGTGAATGACAATTTTGTAATTTAGGATAAGATC | 605 |
| 2660-2698 | TTTCTCTTACTCTGTTTATTTTTAAATGATCATCATAAT | 606 |
| 2808-2851 | TAGCTAGGTTTTTACTGATTATTTTCATTTTTCACATGCATCAG | 607 |
| 3014-3050 | TCTTACTGTAACATTTTTCTATTGTTTAAATAGAAAG | 608 |

Dose Response Analysis

Of the 264 oligonucleotides evaluated in the initial HEK-293 cell-based assay, 71 particularly active oligonucleotides were selected as hits based on their ability to knock down GYS2 levels and were subjected to a secondary screen.

Figure 2A:
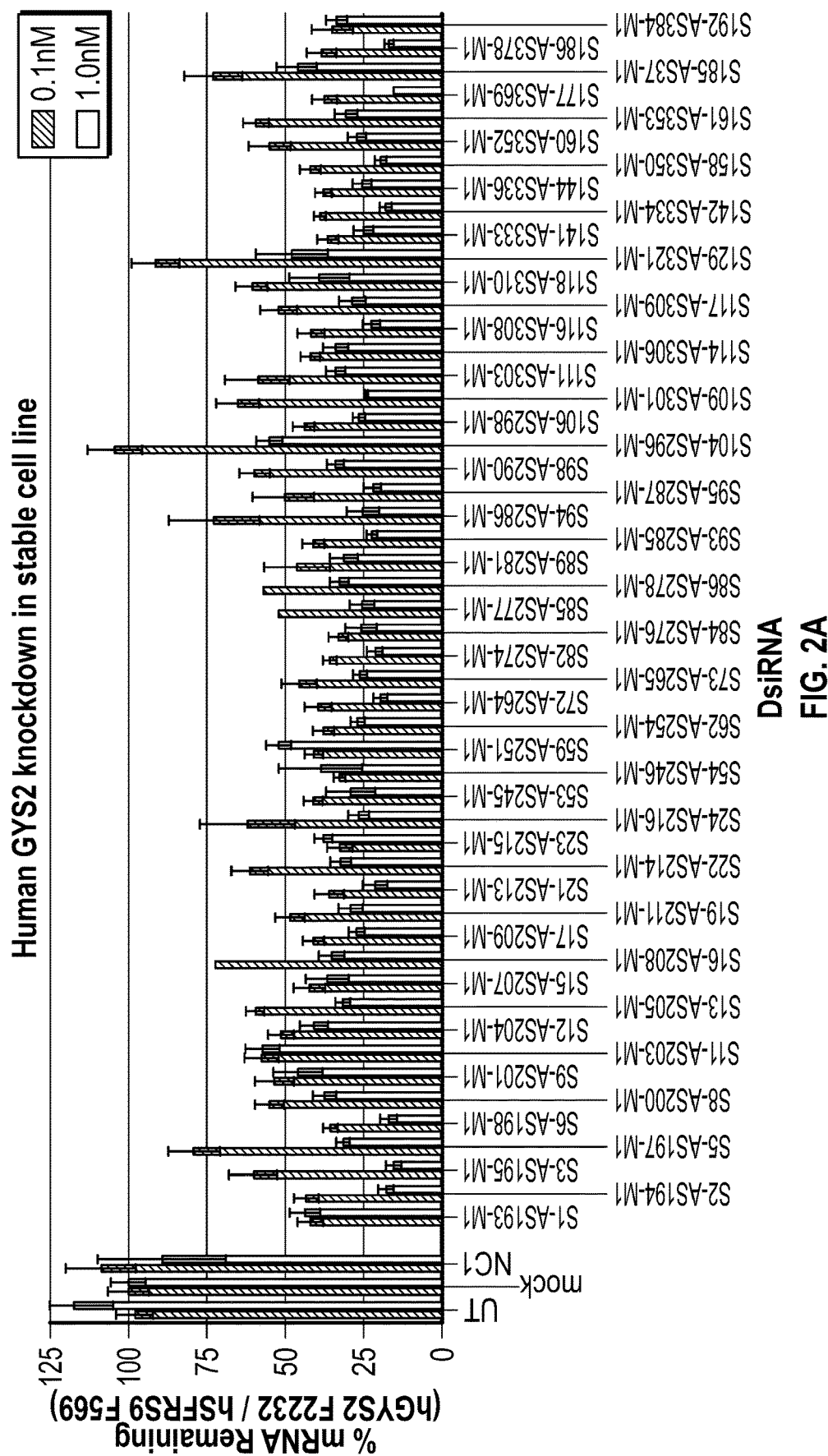
FIGS. 2A and 2B is a set of graphs showing the percentage of mRNA remaining after GYS2 oligonucleotide screening of 71 GYS2 oligonucleotides at two or three different concentrations (0.1 nM and 1.0 nM or 0.03 nM, 0.1 nM, and 1.0 nM) in HEK-293 cells.
Figure 2B:
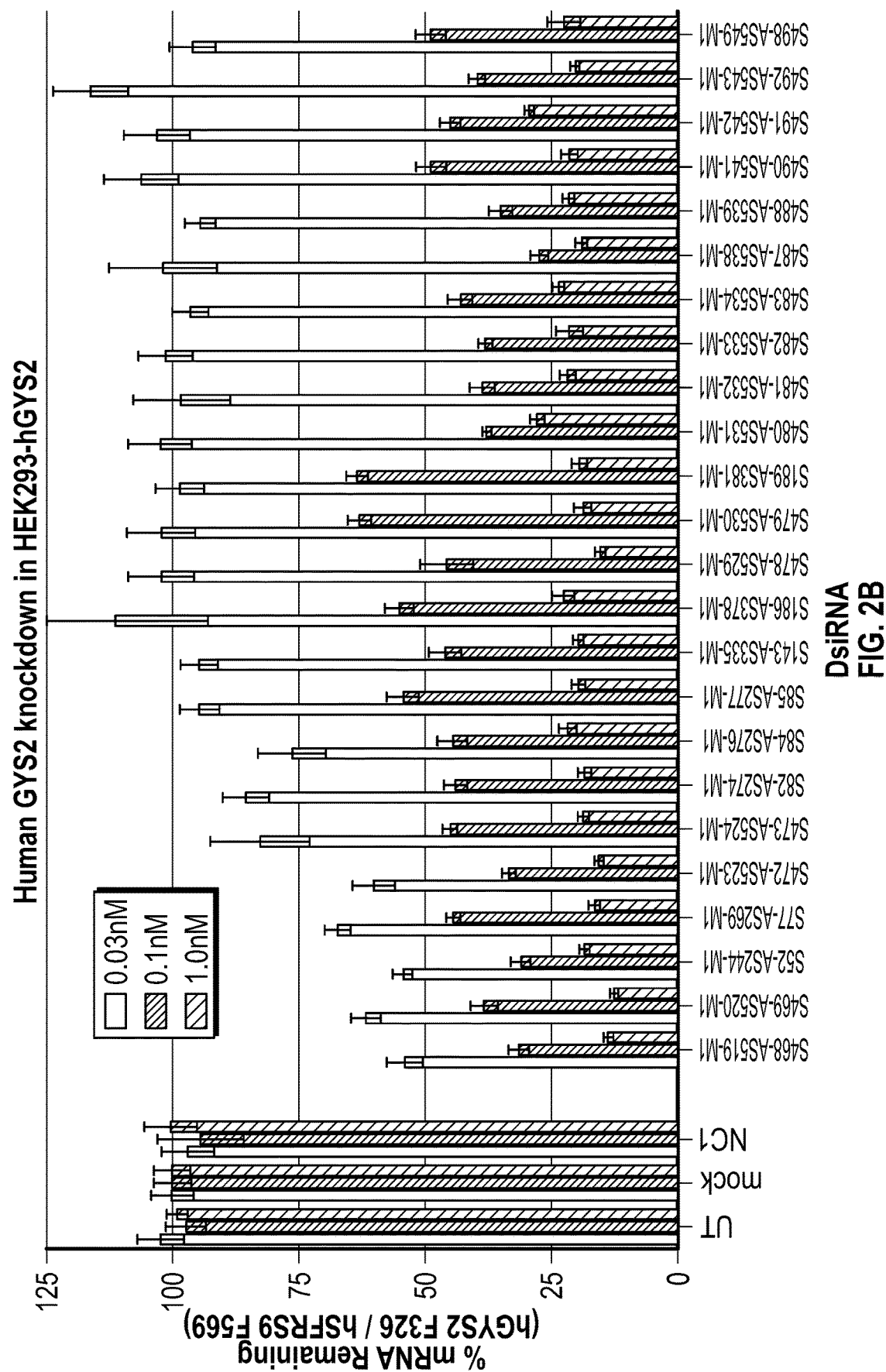

In this secondary screen, the candidate oligonucleotides were tested using the same assay as in the primary screen, but at two or three different concentrations (1 nM, 0.1 nM and 0.03 nM) (FIGS. 2A and 2B). The target mRNA levels were generally normalized based on splicing factor, arginine/serine-rich 9 (SFRS9), a housekeeping gene that provides a stable expression reference across samples, to generate the percent mRNA shown in FIGS. 2A and 2B. The tested oligonucleotides in each of FIGS. 2A and 2B are shown compared to negative control sequences (NC1) and mock transfection. All 71 oligonucleotides had the same modification pattern, designated M1, which contains a combination of ribonucleotides, deoxyribonucleotides and 2'-O-methyl modified nucleotides. The sequences of the 71 oligonucleotides tested are provided in Table 3.

TABLE 3

Candidate oligonucleotide Sequences for HEK-293 Cell-Based Assay

| Hs | Rm | Sense SEQ ID NO. | Corresponding Antisense SEQ ID NO. |
|---|---|---|---|
| X | X | 1-3, 5, 6, 8, 9, 11-13, 15-17, 19, 21-24, 52-54, 59, 62, 72, 73, 77, 82, 84-86, 89, 93-95, 98, 104, 106, 109, 111, 114, 116-118, 129, 141-144, 158, 160, 161, 177, 185, 186, 189, | 193-195, 197, 198, 200, 201, 203-205, 207-209, 211, 213-216, 244-246, 251, 254, 264, 265, 269, 274, 276-278, 281, 285-287, 290, 296, 298, 301, 303, 306, 308-310, 321, 333-336, 350, 352, 353, 369, 377, |

TABLE 3-continued

Candidate oligonucleotide Sequences
for HEK-293 Cell-Based Assay

| Hs | Rm | Sense SEQ ID NO. | Corresponding Antisense SEQ ID NO. |
|---|---|---|---|
| | | 192, 468, 469, 472, 473, 478-480, 482, 483, 487, 488, 490-492, 498 | 378, 381, 384, 519, 520, 523, 524, 529-531, 533, 534, 538, 539, 541-543, 549 |

Hs: human and Rm: *Rhesus macaque*; the sense and antisense SEQ ID NO. columns provide the sense strand and respective antisense strand, in relative order, that are hybridized to make each oligonucleotide. For example, sense strand of SEQ ID NO: 1 hybridizes with antisense strand of SEQ ID NO: 193.

Figure 3:
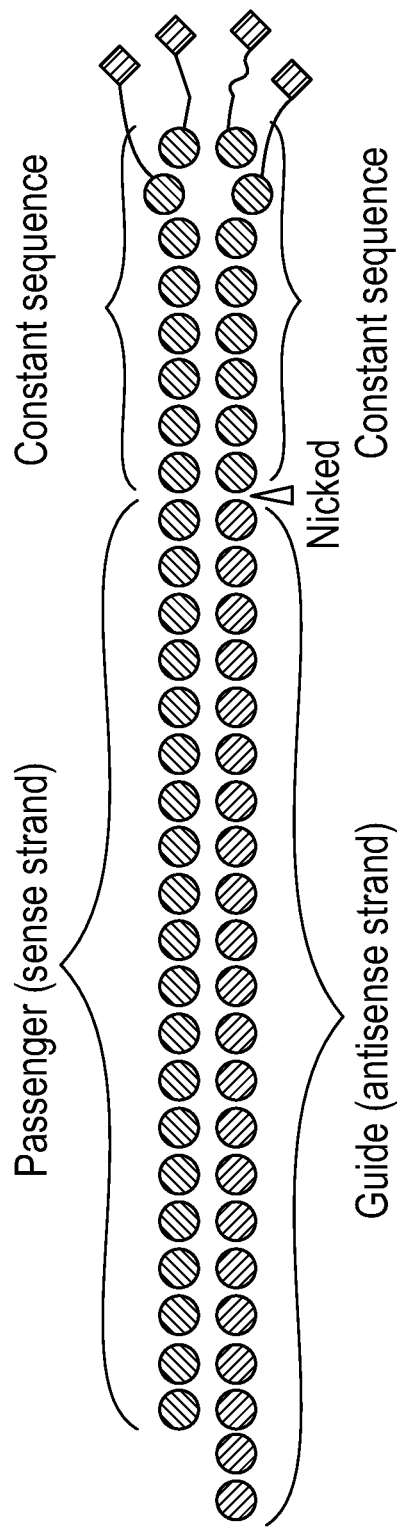
FIG. 3 is a schematic showing a non-limiting example of a double-stranded oligonucleotide with a nicked tetraloop structure that has been conjugated to four GalNAc moieties (diamond shapes).

At this stage, 36 of the most potent sequences from the testing were selected for further analysis. The selected sequences were converted to nicked tetraloop structure formats (a 36-mer passenger strand with a 22-mer guide strand). See FIG. 3 for a generic tetraloop structure. These oligonucleotides were then tested as before, evaluating each oligonucleotide at three concentrations for its ability to reduce GYS2 mRNA expression in HepG2 cells.

Figure 4:
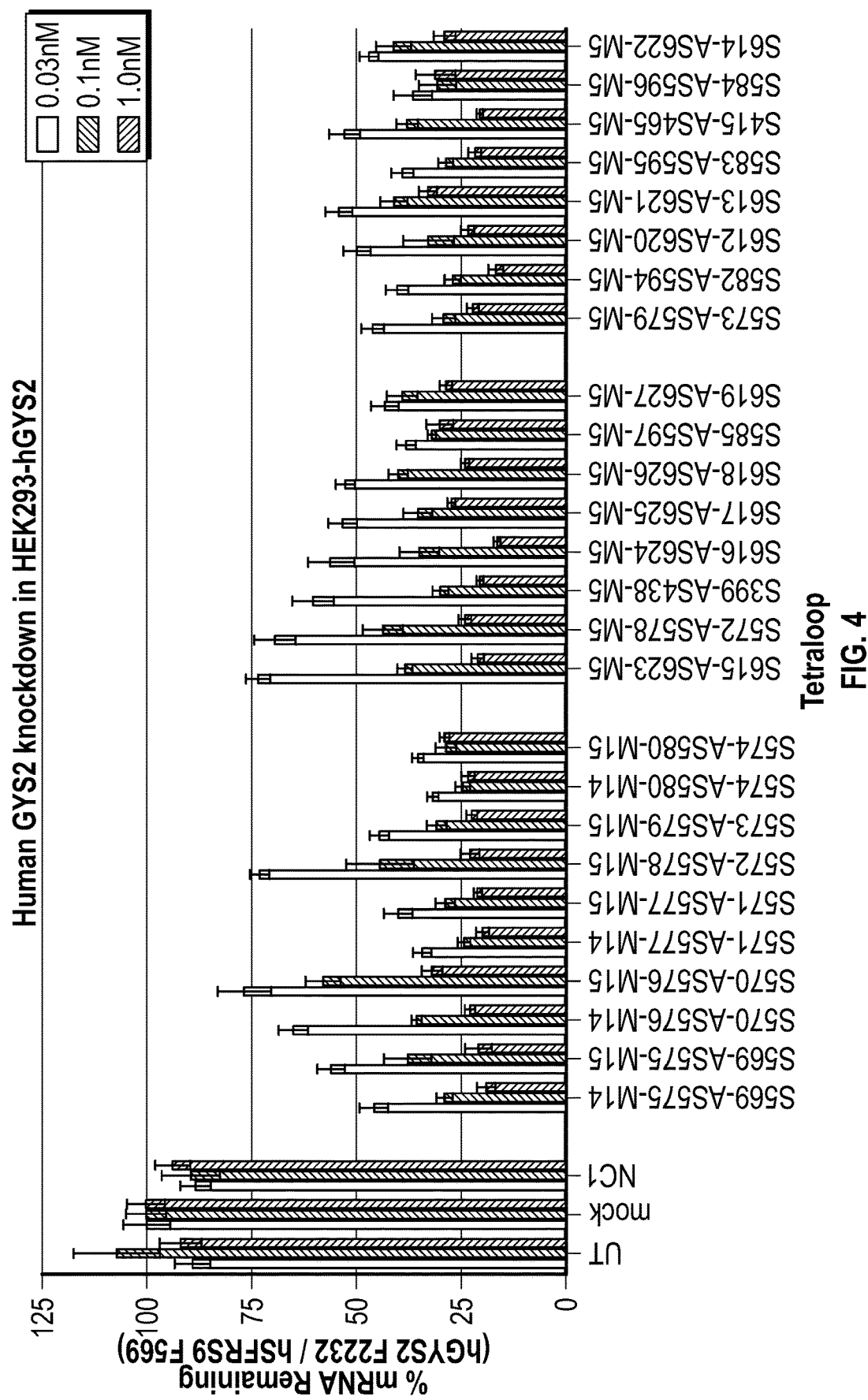
FIG. 4 is a graph showing the results of screening in HEK-293 cells using GYS2 oligonucleotides of different base sequences in one or two different modification patterns. The X-axis lists the 3' end of the sense strand targeted by the oligonucleotide evaluated. A negative control sequence (NCI), untransfected cells, and mock transfected cells are shown at left as controls.

FIG. 4 shows data for oligonucleotides made from different base sequences with nicked tetraloop structures, each adapted to one or two different modification patterns. The X-axis lists the 3' end of the sense strand targeted by the oligonucleotide evaluated. The target mRNA levels were normalized as described above to generate the percent mRNA shown in FIG. 4, and the tested oligonucleotides are shown compared to negative control sequences (NC1) and mock transfection.

Figure 5:
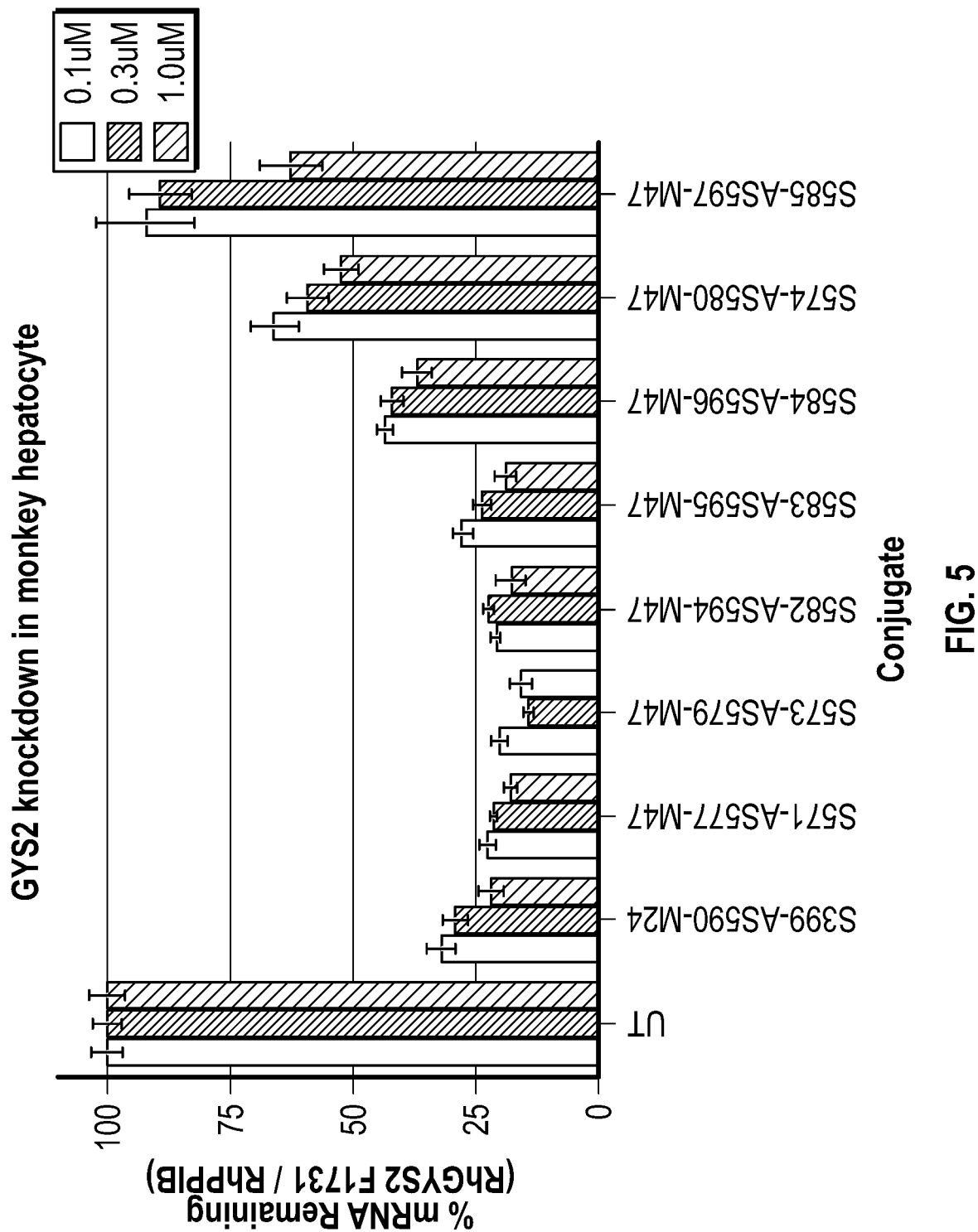
FIG. 5 is a graph showing the results of screening in monkey hepatocyte cells using GYS2 oligonucleotides of different base sequences in the nicked tetraloop structure. The same modification pattern was used, and the oligonucleotides were tested at three different concentrations (0.1 μM, 0.3 μM, and 1.0 μM). Untransfected cells are shown as a control at left.
Figure 6A:
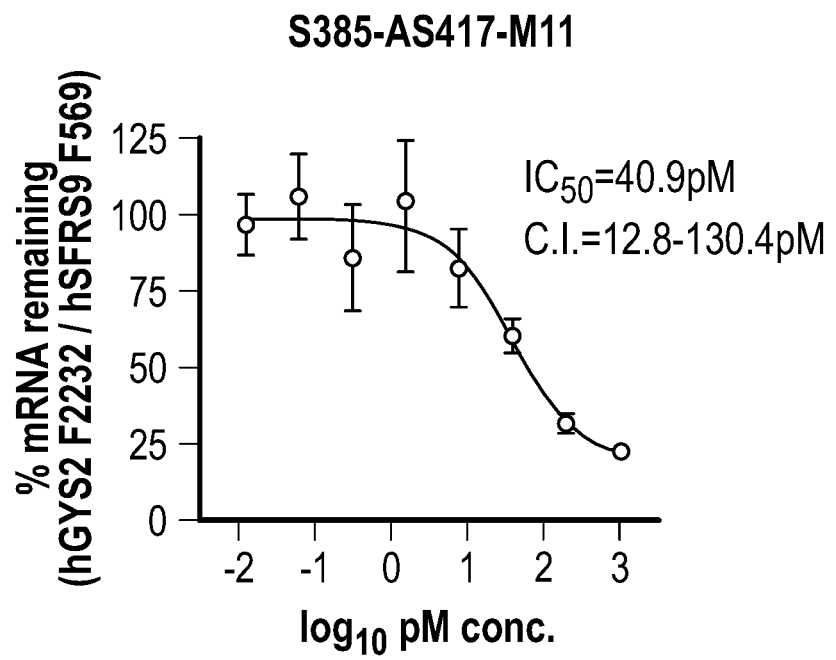
FIGS. 6A and 6B are a series of graphs showing the $IC_{50}$ results for GYS2 oligonucleotides selected from dose response curve screening in HEK-293 cells.
Figure 6A:
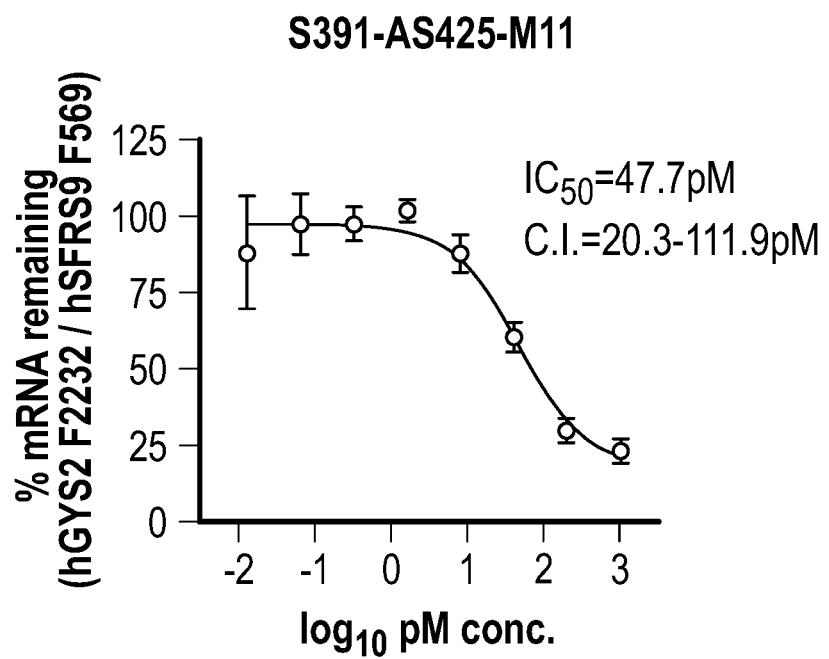
Figure 6A:
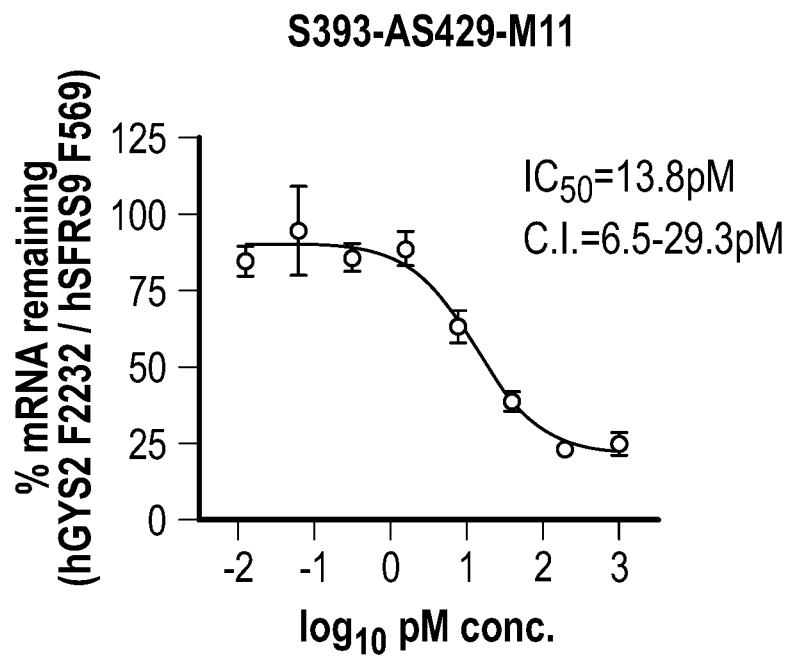
Figure 6A:
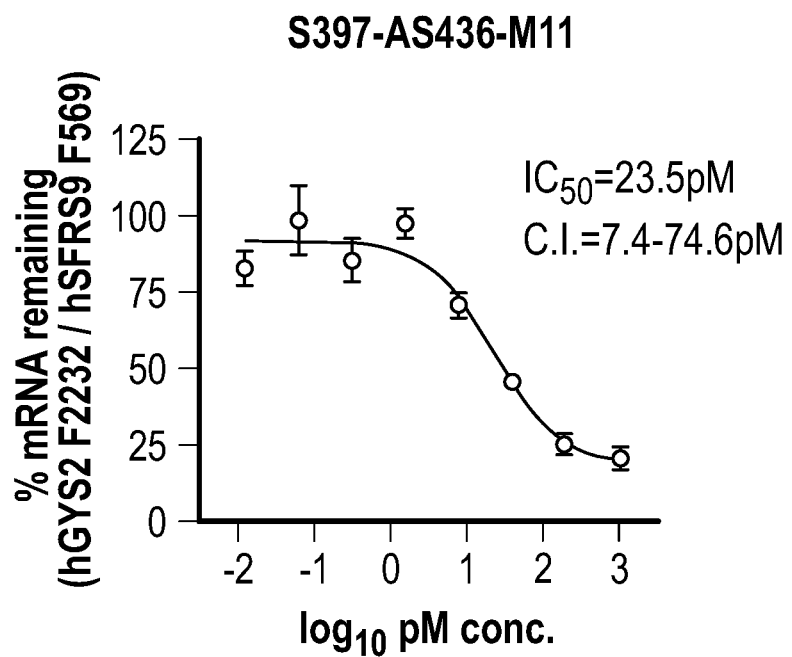
Figure 6A:
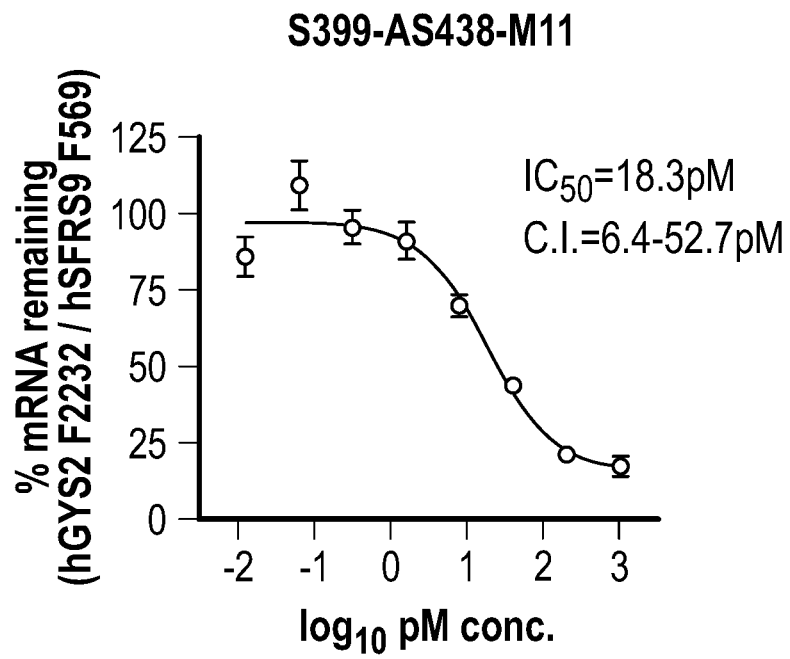
Figure 6A:
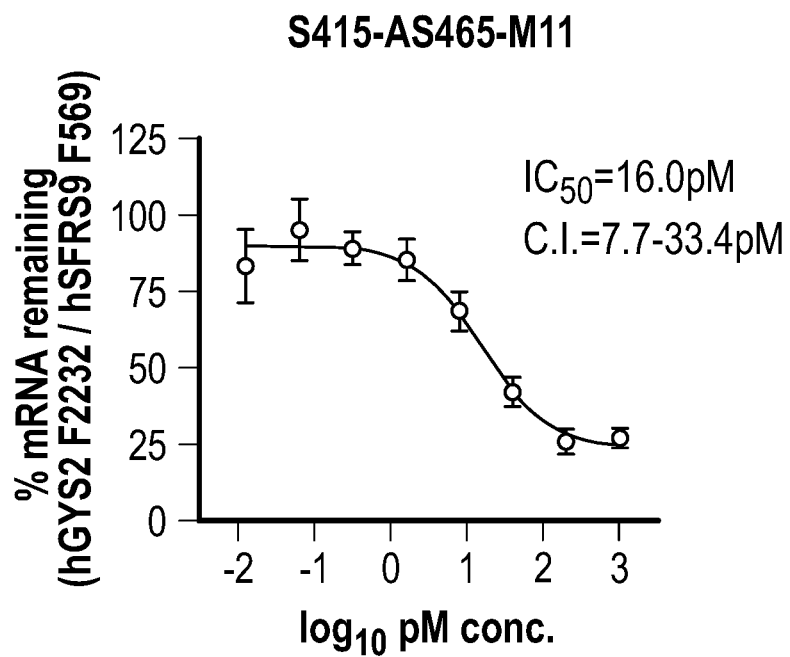
Figure 6B:
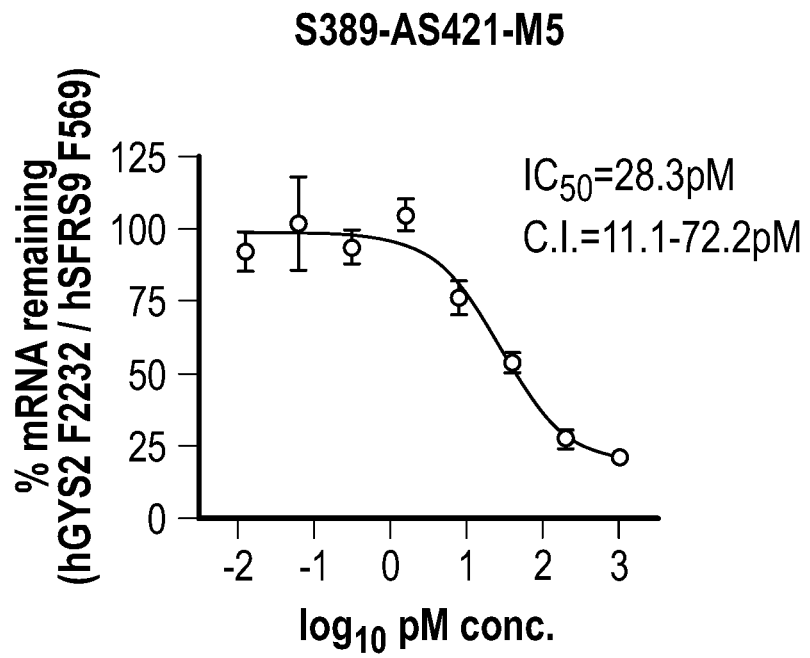
Figure 6B:
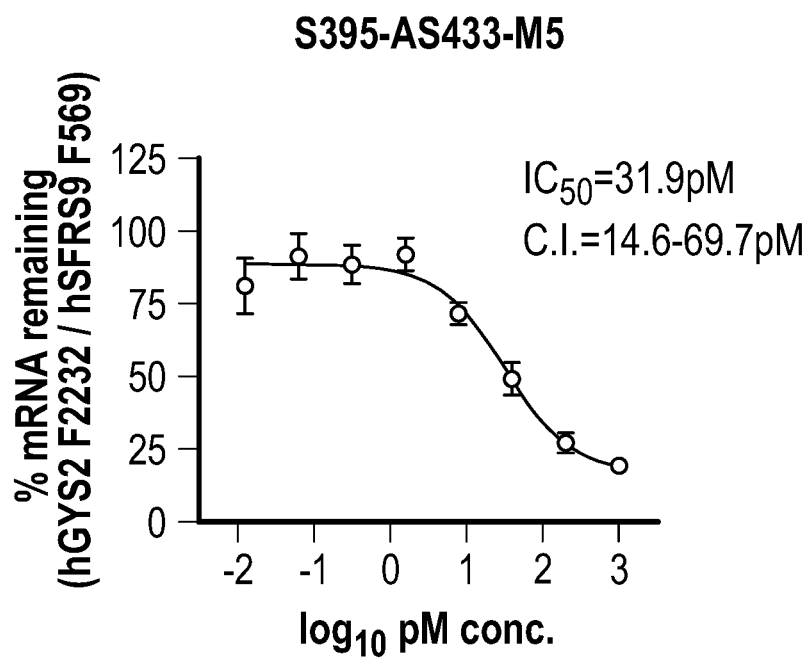
Figure 6B:
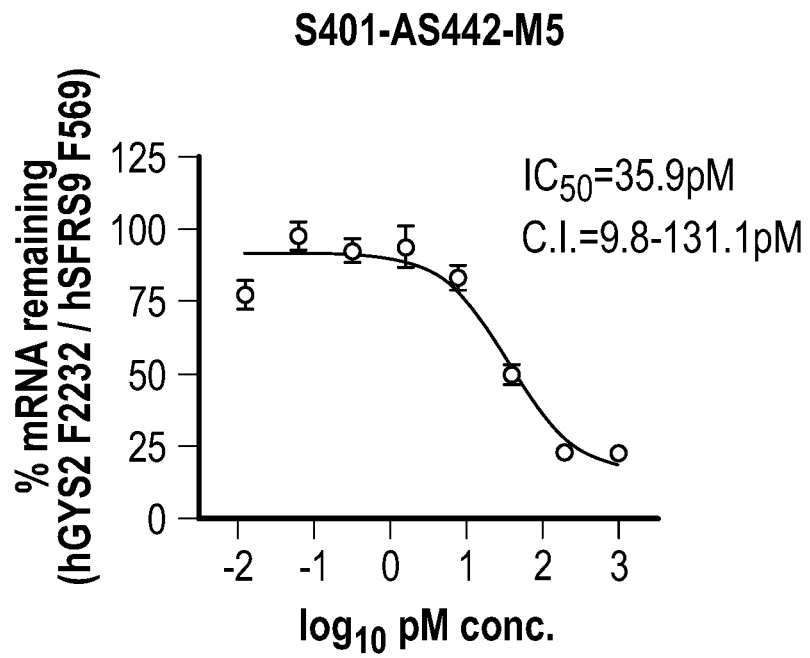
Figure 6B:
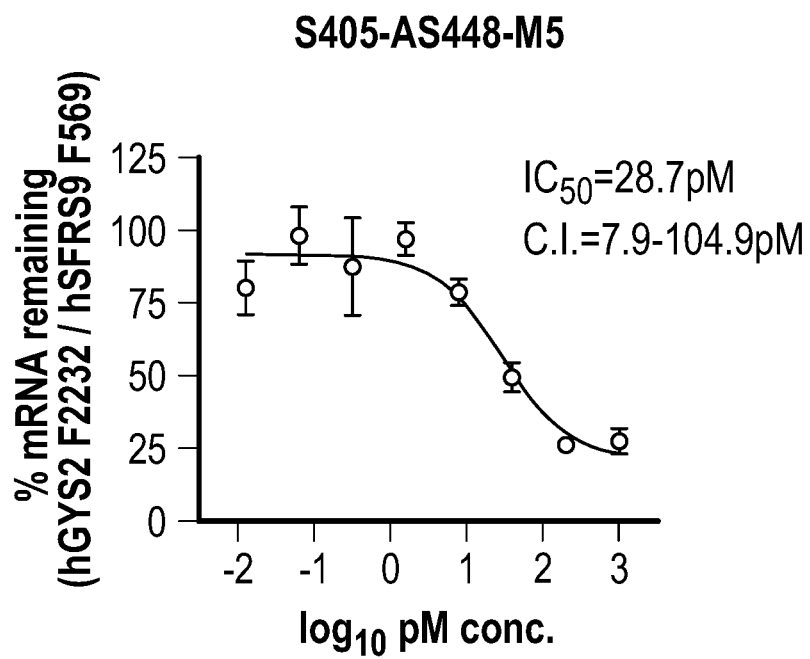
Figure 6B:
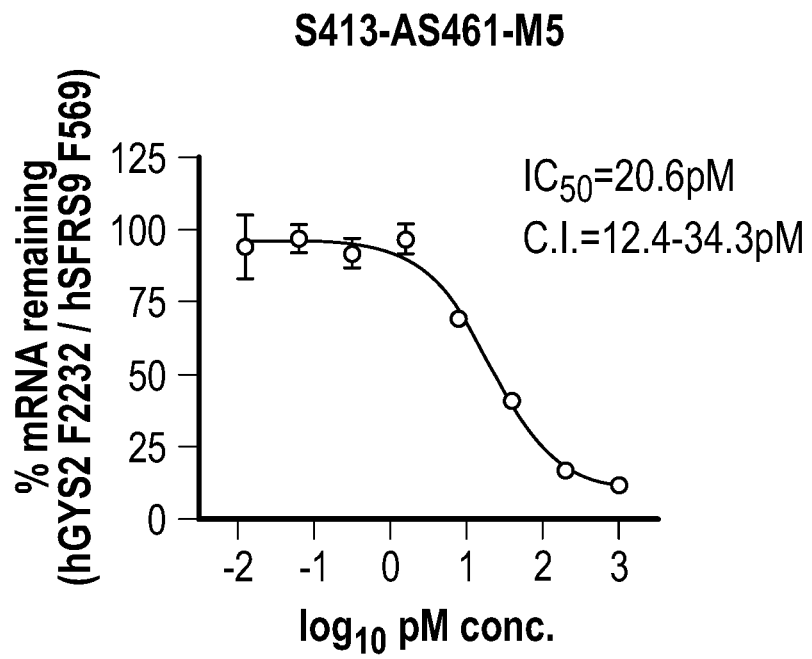
Figure 6B:
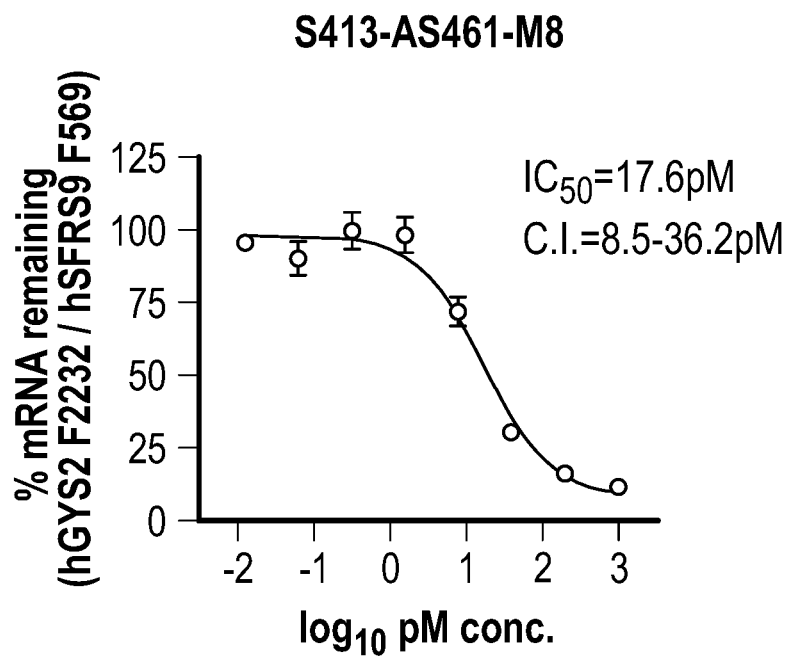

Certain tetraloop-modified oligonucleotides were further tested in monkey hepatocyte cells using the same modification patterns for each compound (FIG. 5) at 0.1 µM, 0.3 µM, and 1.0 µM. The tested oligonucleotides in FIG. 5 are shown compared untransfected cells. Certain oligonucleotides were further tested using a full dose response curve in HEK-293 cells in order to determine the half maximal inhibitory concentration (IC$_{50}$) for each compound (see FIGS. 6A and 6B).

In Vivo Murine Screening

Data from the above in vitro experiments were assessed to identify tetraloops and modification patterns that would improve delivery properties while maintaining activity for reduction of GYS2 expression in the mouse hepatocytes. Based on this analysis, select oligonucleotides were then conjugated to GalNAc moieties. Four GalNAc moieties were conjugated to nucleotides in the tetraloop of the sense strand. Conjugation was performed using a click linker. The GalNAc used was as shown below:

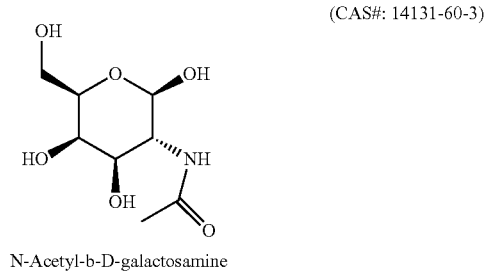

(CAS#: 14131-60-3)

N-Acetyl-b-D-galactosamine

A total of 65 potent GalNAc-conjugated GYS2 oligonucleotides from 18 different base sequences and having different modification patterns with nicked tetraloop structures were tested. Selected GYS2 oligonucleotide sequences were active against human and monkey mRNA sequences but not mouse Gys2. GYS2 oligonucleotides were subcutaneously administered to CD-1 mice transiently expressing human GYS2 mRNA by hydrodynamic injection of a human GYS2 expression plasmid at 0.5-5 mg/kg. Mice were euthanized on day 4 following administration. Liver samples were obtained and RNA was extracted to evaluate GYS2 mRNA levels by RT-qPCR. The percent GYS2 mRNA as compared to PBS control mRNA was determined based on these measurements.

Figure 7:
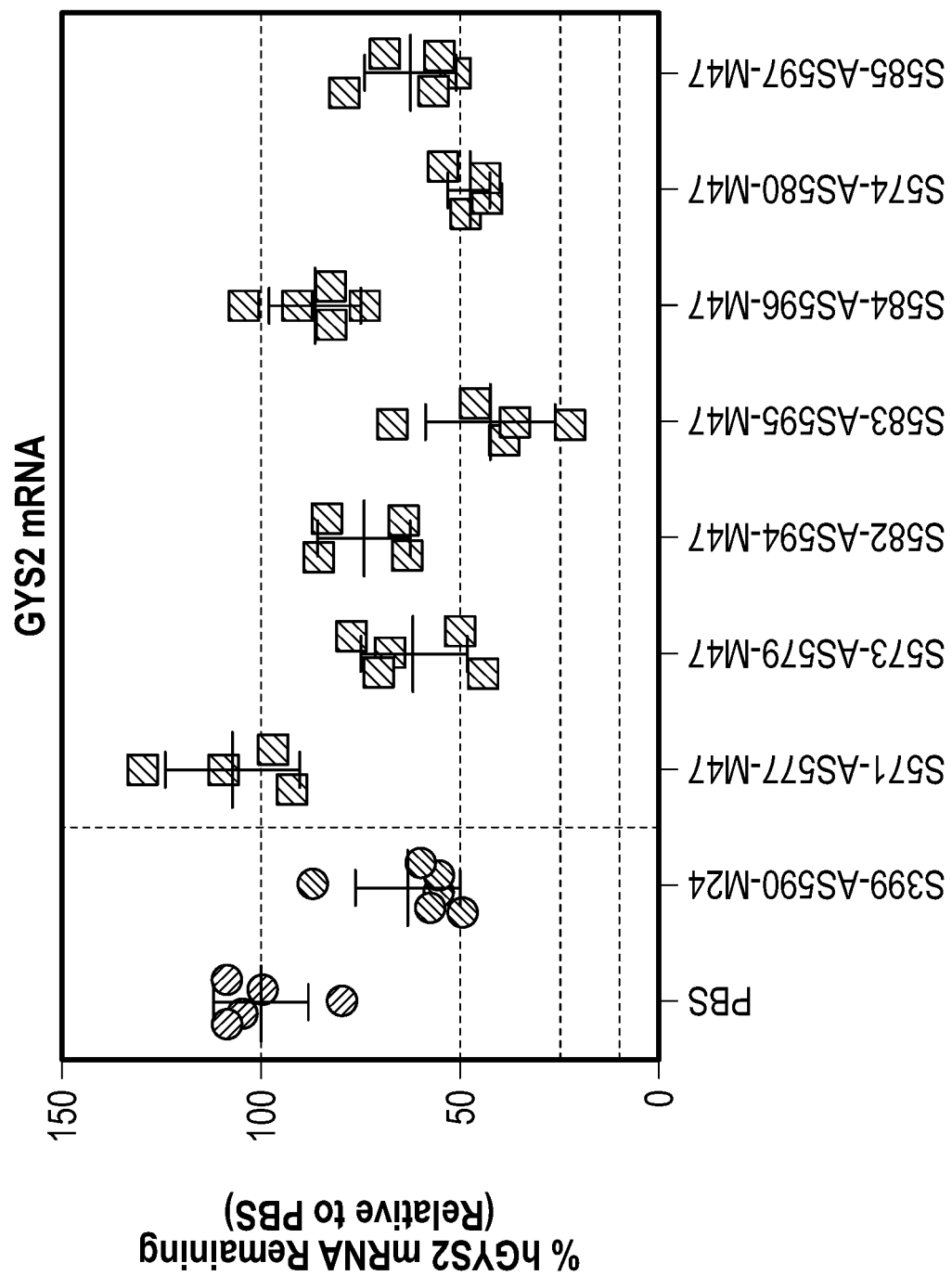
FIG. 7 is a graph showing an in vivo activity evaluation of GalNAc-conjugated GYS2 oligonucleotides in a nicked tetraloop structure. Eight different oligonucleotide sequences were tested. Oligonucleotides were subcutaneously administered to mice expressed human GYS2, at 0.5 mg/kg. The data show the amount of GYS2 mRNA remaining at day 4 following administration normalized to PBS control.

From the 65 conjugates tested, the eight most potent base sequences were identified and each tested with the same modification pattern by subcutaneous injection at 0.5 mg/kg to CD-1 mice transiently expressing human GYS2 mRNA. Mice were euthanized on day 4 following administration. Liver samples were obtained and RNA was extracted to evaluate GYS2 mRNA levels by RT-qPCR. The percent GYS2 mRNA as compared to PBS control mRNA was determined based on these measurements and is shown in FIG. 7.

Materials and Methods

Transfection

For the first screen, Lipofectamine RNAiMAX™ was used to complex the oligonucleotides for efficient transfection. Oligonucleotides, RNAiMAX and Opti-MEM incubated together at room temperature for 20 minutes and then 50 µL of this mix was added per well to plates prior to transfection. Media was aspirated from a flask of actively passaging cells and the cells were incubated at 37° C. in the presence of trypsin for 3-5 minutes. After cells no longer adhered to the flask, cell growth media (lacking penicillin and streptomycin) was added to neutralize the trypsin and to suspend the cells. A 10 µL aliquot was removed and counted with a hemocytometer to quantify the cells on a per milliliter basis. For cells, 10,000 or 25,000 cells/well were seeded per well in media (e.g., 100 µL of media). A diluted cell suspension was added to the 96-well transfection plates, which already contained the oligonucleotides in Opti-MEM. The transfection plates were then incubated for 24 hours at 37° C. After 24 hours of incubation, media was aspirated from each well. Cells were lysed using the lysis buffer from the Promega RNA Isolation kit. The lysis buffer was added to each well. The lysed cells were then transferred to the Corbett XtractorGENE (QIAxtractor) for RNA isolation or stored at −80° C.

For subsequent screens and experiments, e.g., the secondary screen, Lipofectamine RNAiMAx was used to complex the oligonucleotides for reverse transfection. The complexes were made by mixing RNAiMAX and siRNAs in OptiMEM medium for 15 minutes. The transfection mixture was transferred to multi-well plates and cell suspension was added to the wells. After 24 hours incubation the cells were washed once with PBS and then lysed using lysis buffer from the Promega SV96 kit. The RNA was purified using the SV96 plates in a vacuum manifold. Four microliters of the purified RNA was then heated at 65° C. for 5 minutes and cooled to 4° C. The RNA was then used for reverse transcription using the High Capacity Reverse Transcription kit (Life Technologies) in a 10 microliter reaction. The cDNA was then diluted to 50 µL with nuclease free water and used for quantitative PCR with multiplexed 5'-endonuclease assays and SSoFast qPCR mastermix (Bio-Rad laboratories).

cDNA Synthesis

RNA was isolated from mammalian cells in tissue culture using the Corbett X-tractor Gene™ (QIAxtractor). A modified SuperScript II protocol was used to synthesize cDNA from the isolated RNA. Isolated RNA (approximately 5 ng/μL) was heated to 65° C. for five minutes and incubated with dNPs, random hexamers, oligo dTs, and water. The mixture was cooled for 15 seconds. An "enzyme mix," consisting of water, 5× first strand buffer, DTT, SUPERase•In™ (an RNA inhibitor), and SuperScript II RTase was added to the mixture. The contents were heated to 42° C. for one hour, then to 70° C. for 15 minutes, and then cooled to 4° C. using a thermocycler. The resulting cDNA was then subjected to SYBR®-based qPCR. The qPCR reactions were multiplexed, containing two 5' endonuclease assays per reaction.

qPCR Assays

Primer sets were initially screened using SYBR®-based qPCR. Assay specificity was verified by assessing melt curves as well as "minus RT" controls. Dilutions of cDNA template (10-fold serial dilutions from 20 ng and to 0.02 ng per reaction) from HeLa and Hepa1-6 cells were used to test human (Hs) and mouse (Mm) assays, respectively. qPCR assays were set up in 384-well plates, covered with MicroAmp film, and run on the 7900HT from Applied Biosystems. Reagent concentrations and cycling conditions included the following: 2×SYBR mix, 10 μM forward primer, 10 μM reverse primer, DD $H_2O$, and cDNA template up to a total volume of 10 μL.

Cloning

PCR amplicons that displayed a single melt-curve were ligated into the pGEM®-T Easy vector kit from Promega according to the manufacturer's instructions. Following the manufacturer's protocol, JM109 High Efficiency cells were transformed with the newly ligated vectors. The cells were then plated on LB plates containing ampicillin and incubated at 37° C. overnight for colony growth.

PCR Screening and Plasmid Mini-Prep

PCR was used to identify colonies of *E. coli* that had been transformed with a vector containing the ligated amplicon of interest. Vector-specific primers that flank the insert were used in the PCR reaction. All PCR products were then run on a 1% agarose gel and imaged by a transilluminator following staining. Gels were assessed qualitatively to determine which plasmids appeared to contain a ligated amplicon of the expected size (approximately 300 bp, including the amplicon and the flanking vector sequences specific to the primers used).

The colonies that were confirmed transformants by PCR screening were then incubated overnight in cultures consisting of 2 mL LB broth with ampicillin at 37° C. with shaking. *E. coli* cells were then lysed, and the plasmids of interest were isolated using Promega's Mini-Prep kit. Plasmid concentration was determined by UV absorbance at 260 nm.

Plasmid Sequencing and Quantification

Purified plasmids were sequenced using the BigDye® Terminator sequencing kit. The vector-specific primer, T7, was used to give read lengths that span the insert. The following reagents were used in the sequencing reactions: water, 5× sequencing buffer, BigDye terminator mix, T7 primer, and plasmid (100 ng/μL) to a volume of 10 μL. The mixture was held at 96° C. for one minute, then subjected to 15 cycles of 96° C. for 10 seconds, 50° C. for 5 seconds, 60° C. for 1 minute, 15 seconds; 5 cycles of 96° C. for 10 seconds, 50° C. for 5 seconds, 60° C. for 1 minute, 30 seconds; and 5 cycles of 96° C. for 10 seconds, 50° C. for 5 seconds, and 60° C. for 2 minutes. Dye termination reactions were then sequenced using Applied Biosystems' capillary electrophoresis sequencers.

Sequence-verified plasmids were then quantified. They were linearized using a single cutting restriction endonuclease. Linearity was confirmed using agarose gel electrophoresis. All plasmid dilutions were made in TE buffer (pH 7.5) with 100 μg of tRNA per mL buffer to reduce non-specific binding of plasmid to the polypropylene vials.

The linearized plasmids were then serially diluted from 1,000,000 to 01 copies per μL and subjected to qPCR. Assay efficiency was calculated and the assays were deemed acceptable if the efficiency was in the range of 90-110%.

Multi-Plexing Assays

For each target, mRNA levels were quantified by two 5' nuclease assays. In general, several assays are screened for each target. The two assays selected displayed a combination of good efficiency, low limit of detection, and broad 5'→3' coverage of the gene of interest (GOI). Both assays against one GOI could be combined in one reaction when different fluorophores were used on the respective probes. Thus, the final step in assay validation was to determine the efficiency of the selected assays when they were combined in the same qPCR or "multi-plexed."

Linearized plasmids for both assays in 10-fold dilutions were combined and qPCR was performed. The efficiency of each assay was determined as described above. The accepted efficiency rate was 90-110%. While validating multi-plexed reactions using linearized plasmid standards, $C_q$ values for the target of interest were also assessed using cDNA as the template. For human or mouse targets, HeLa and Hepa1-6 cDNA were used, respectively. The cDNA, in this case, was derived from RNA isolated on the Corbett (~5 ng/μl in water) from untransfected cells. In this way, the observed $C_q$ values from this sample cDNA were representative of the expected $C_q$ values from a 96-well plate transfection. In cases where $C_q$ values were greater than 30, other cell lines were sought that exhibit higher expression levels of the gene of interest. A library of total RNA isolated from via high-throughput methods on the Corbett from each human and mouse line was generated and used to screen for acceptable levels of target expression.

Description of Oligonucleotide Nomenclature

All oligonucleotides described herein are designated either $SN_1$-$ASN_2$-$MN_3$. The following designations apply:

$N_1$: sequence identifier number of the sense strand sequence $N_2$: sequence identifier number of the antisense strand sequence $N_3$: reference number of modification pattern, in which each number represents a pattern of modified nucleotides in the oligonucleotide.

For example, S27-AS219-M1 represents an oligonucleotide with a sense sequence that is set forth by SEQ ID NO: 27, an antisense sequence that is set forth by SEQ ID NO: 219, and which is adapted to a modification pattern identified as M1.

TABLE 4

GYS2 RNAi oligonucleotides

| App Name | Sense Sequence | S SEQ ID NO | Antisense Sequence | AS SEQ ID NO |
|---|---|---|---|---|
| S1-AS193-M1 | CAGGUGCAUUUUGGAAGAUGGCUGA | 1 | UCAGCCAUCUUCCAAAAUGCACCUGGC | 193 |
| S2-AS194-M1 | AGGUGCAUUUUGGAAGAUGGCUGAT | 2 | AUCAGCCAUCUUCCAAAAUGCACCUGG | 194 |
| S3-AS195-M1 | GGUGCAUUUUGGAAGAUGGCUGATA | 3 | UAUCAGCCAUCUUCCAAAAUGCACCUG | 195 |
| S4-AS196-M1 | GUGCAUUUUGGAAGAUGGCUGAUAG | 4 | CUAUCAGCCAUCUUCCAAAAUGCACCU | 196 |
| S5-AS197-M1 | UGCAUUUUGGAAGAUGGCUGAUAGA | 5 | UCUAUCAGCCAUCUUCCAAAAUGCACC | 197 |
| S6-AS198-M1 | AAGGAAGUCCUUAUGUGGUACUUTT | 6 | AAAAGUACCACAUAAGGACUUCCUUCU | 198 |
| S7-AS199-M1 | GAAGUCCUUAUGUGGUACUUUUUGA | 7 | UCAAAAGUACCACAUAAGGACUUCCU | 199 |
| S8-AS200-M1 | AAGUCCUUAUGUGGUACUUUUUGAC | 8 | GUCAAAAGUACCACAUAAGGACUUCC | 200 |
| S9-AS201-M1 | AGUCCUUAUGUGGUACUUUUUGACA | 9 | UGUCAAAAGUACCACAUAAGGACUUC | 201 |
| S10-AS202-M1 | GUCCUUAUGUGGUACUUUUUGACAT | 10 | AUGUCAAAAGUACCACAUAAGGACUU | 202 |
| S11-AS203-M1 | CCUUAUGUGGUACUUUUUGACAUAG | 11 | CUAUGUCAAAAGUACCACAUAAGGAC | 203 |
| S12-AS204-M1 | GUACUUUUUGACAUAGGCUAUUCAG | 12 | CUGAAUAGCCUAUGUCAAAAGUACCA | 204 |
| S13-AS205-M1 | CGAGAAGCCAAUGAUAUGCUGAUAT | 13 | AUAUCAGCAUAUCAUUGGCUUCUCGGU | 205 |
| S14-AS206-M1 | GAGAAGCCAAUGAUAUGCUGAUAUT | 14 | AAUAUCAGCAUAUCAUUGGCUUCUCGG | 206 |
| S15-AS207-M1 | AGAAGCCAAUGAUAUGCUGAUAUTT | 15 | AAAUAUCAGCAUAUCAUUGGCUUCUCG | 207 |
| S16-AS208-M1 | GAAGCCAAUGAUAUGCUGAUAUUTG | 16 | CAAAUAUCAGCAUAUCAUUGGCUUCUC | 208 |
| S17-AS209-M1 | AGCCAAUGAUAUGCUGAUAUUUGGA | 17 | UCCAAAUAUCAGCAUAUCAUUGGCUUC | 209 |
| S18-AS210-M1 | GCCAAUGAUAUGCUGAUAUUUGGAT | 18 | AUCCAAAUAUCAGCAUAUCAUUGGCUU | 210 |
| S19-AS211-M1 | CCAAUGAUAUGCUGAUAUUUGGATC | 19 | GAUCCAAAUAUCAGCAUAUCAUUGGCU | 211 |
| S20-AS212-M1 | AAUGAUAUGCUGAUAUUUGGAUCTT | 20 | AAGAUCCAAAUAUCAGCAUAUCAUUGG | 212 |
| S21-AS213-M1 | AUGAUAUGCUGAUAUUUGGAUCUTT | 21 | AAAGAUCCAAAUAUCAGCAUAUCAUUG | 213 |
| S22-AS214-M1 | UGAUAUGCUGAUAUUUGGAUCUUTA | 22 | UAAAGAUCCAAAUAUCAGCAUAUCAUU | 214 |
| S23-AS215-M1 | AUAUGCUGAUAUUUGGAUCUUUAAC | 23 | GUUAAAGAUCCAAAUAUCAGCAUAUCA | 215 |
| S24-AS216-M1 | AUGCUGAUAUUUGGAUCUUUAACTG | 24 | CAGUUAAAGAUCCAAAUAUCAGCAUAU | 216 |
| S25-AS217-M1 | UCUUUAACUGCCUGGUUCUUAAAAG | 25 | CUUUUAAGAACCAGGCAGUUAAAGAUC | 217 |

TABLE 4-continued

GYS2 RNAi oligonucleotides

| App Name | Sense Sequence | S SEQ ID NO | Antisense Sequence | AS SEQ ID NO |
|---|---|---|---|---|
| S26-AS218-M1 | CUUUAACUGCCUGGUUCUUAAAAGA | 26 | UCUUUUAAGAACCAGGCAGUUAAAGAU | 218 |
| S27-AS219-M1 | UUUAACUGCCUGGUUCUUAAAAGAG | 27 | CUCUUUUAAGAACCAGGCAGUUAAAGA | 219 |
| S28-AS220-M1 | UUAACUGCCUGGUUCUUAAAAGAGG | 28 | CCUCUUUUAAGAACCAGGCAGUUAAAG | 220 |
| S29-AS221-M1 | UAACUGCCUGGUUCUUAAAAGAGGT | 29 | ACCUCUUUUAAGAACCAGGCAGUUAAA | 221 |
| S30-AS222-M1 | UUGCCCAAUUCCAUGAAUGGCAGGC | 30 | GCCUGCCAUUCAUGGAAUUGGGCAACG | 222 |
| S31-AS223-M1 | UGCCCAAUUCCAUGAAUGGCAGGCT | 31 | AGCCUGCCAUUCAUGGAAUUGGGCAAC | 223 |
| S32-AS224-M1 | GCCCAAUUCCAUGAAUGGCAGGCTG | 32 | CAGCCUGCCAUUCAUGGAAUUGGGCAA | 224 |
| S33-AS225-M1 | CCCAAUUCCAUGAAUGGCAGGCUGG | 33 | CCAGCCUGCCAUUCAUGGAAUUGGGCA | 225 |
| S34-AS226-M1 | CCAAUUCCAUGAAUGGCAGGCUGGA | 34 | UCCAGCCUGCCAUUCAUGGAAUUGGGC | 226 |
| S35-AS227-M1 | CAAUUCCAUGAAUGGCAGGCUGGAA | 35 | UUCCAGCCUGCCAUUCAUGGAAUUGGG | 227 |
| S36-AS228-M1 | AAUUCCAUGAAUGGCAGGCUGGAAT | 36 | AUUCCAGCCUGCCAUUCAUGGAAUUGG | 228 |
| S37-AS229-M1 | AUUCCAUGAAUGGCAGGCUGGAATT | 37 | AAUUCCAGCCUGCCAUUCAUGGAAUUG | 229 |
| S38-AS230-M1 | UUCCAUGAAUGGCAGGCUGGAAUTG | 38 | CAAUUCCAGCCUGCCAUUCAUGGAAUU | 230 |
| S39-AS231-M1 | UCCAUGAAUGGCAGGCUGGAAUUGG | 39 | CCAAUUCCAGCCUGCCAUUCAUGGAAU | 231 |
| S40-AS232-M1 | GGAAACUUCCUAUUGCCACAAUAUT | 40 | AAUAUUGUGGCAAUAGGAAGUUUCCUG | 232 |
| S41-AS233-M1 | GGUAUCUCUGUGCAGCAAAUAUUGA | 41 | UCAAUAUUUGCUGCACAGAGAUACCUC | 233 |
| S42-AS234-M1 | GUAUCUCUGUGCAGCAAAUAUUGAT | 42 | AUCAAUAUUUGCUGCACAGAGAUACCU | 234 |
| S43-AS235-M1 | UAUCUCUGUGCAGCAAAUAUUGAUT | 43 | AAUCAAUAUUUGCUGCACAGAGAUACC | 235 |
| S44-AS236-M1 | AUCUCUGUGCAGCAAAUAUUGAUTT | 44 | AAAUCAAUAUUUGCUGCACAGAGAUAC | 236 |
| S45-AS237-M1 | UCUCUGUGCAGCAAAUAUUGAUUTC | 45 | GAAAUCAAUAUUUGCUGCACAGAGAUA | 237 |
| S46-AS238-M1 | CUCUGUGCAGCAAAUAUUGAUUUCT | 46 | AGAAAUCAAUAUUUGCUGCACAGAGAU | 238 |
| S47-AS239-M1 | UCUGUGCAGCAAAUAUUGAUUUCTA | 47 | UAGAAAUCAAUAUUUGCUGCACAGAGA | 239 |
| S48-AS240-M1 | CUGUGCAGCAAAUAUUGAUUUCUAC | 48 | GUAGAAAUCAAUAUUUGCUGCACAGAG | 240 |
| S49-AS241-M1 | UGUGCAGCAAAUAUUGAUUUCUACA | 49 | UGUAGAAAUCAAUAUUUGCUGCACAGA | 241 |
| S50-AS242-M1 | GUGCAGCAAAUAUUGAUUUCUACAA | 50 | UUGUAGAAAUCAAUAUUUGCUGCACAG | 242 |

TABLE 4-continued

GYS2 RNAi oligonucleotides

| App Name | Sense Sequence | S SEQ ID NO | Antisense Sequence | AS SEQ ID NO |
|---|---|---|---|---|
| S51-AS243-M1 | UGCAGCAAAUAUUGAUUUCUACAAC | 51 | GUUGUAGAAAUCAAUAUUUGCUGCACA | 243 |
| S52-AS244-M1 | GCAGCAAAUAUUGAUUUCUACAACC | 52 | GGUUGUAGAAAUCAAUAUUUGCUGCAC | 244 |
| S53-AS245-M1 | CAGCAAAUAUUGAUUUCUACAACCA | 53 | UGGUUGUAGAAAUCAAUAUUUGCUGCA | 245 |
| S54-AS246-M1 | AGCAAAUAUUGAUUUCUACAACCAT | 54 | AUGGUUGUAGAAAUCAAUAUUUGCUGC | 246 |
| S55-AS247-M1 | GCAAAUAUUGAUUUCUACAACCATC | 55 | GAUGGUUGUAGAAAUCAAUAUUUGCUG | 247 |
| S56-AS248-M1 | AUAUUGAUUUCUACAACCAUCUUGA | 56 | UCAAGAUGGUUGUAGAAAUCAAUAUUU | 248 |
| S57-AS249-M1 | UUGAUUUCUACAACCAUCUUGAUAA | 57 | UUAUCAAGAUGGUUGUAGAAAUCAAUA | 249 |
| S58-AS250-M1 | GAUUUCUACAACCAUCUUGAUAAGT | 58 | ACUUAUCAAGAUGGUUGUAGAAAUCAA | 250 |
| S59-AS251-M1 | AUUUCUACAACCAUCUUGAUAAGTT | 59 | AACUUAUCAAGAUGGUUGUAGAAAUCA | 251 |
| S60-AS252-M1 | UUCUACAACCAUCUUGAUAAGUUTA | 60 | UAAACUUAUCAAGAUGGUUGUAGAAAU | 252 |
| S61-AS253-M1 | CUACAACCAUCUUGAUAAGUUUAAC | 61 | GUUAAACUUAUCAAGAUGGUUGUAGAA | 253 |
| S62-AS254-M1 | UACAACCAUCUUGAUAAGUUUAACA | 62 | UGUUAAACUUAUCAAGAUGGUUGUAGA | 254 |
| S63-AS255-M1 | ACAACCAUCUUGAUAAGUUUAACAT | 63 | AUGUUAAACUUAUCAAGAUGGUUGUAG | 255 |
| S64-AS256-M1 | CAACCAUCUUGAUAAGUUUAACATT | 64 | AAUGUUAAACUUAUCAAGAUGGUUGUA | 256 |
| S65-AS257-M1 | AACCAUCUUGAUAAGUUUAACAUTG | 65 | CAAUGUUAAACUUAUCAAGAUGGUUGU | 257 |
| S66-AS258-M1 | ACCAUCUUGAUAAGUUUAACAUUGA | 66 | UCAAUGUUAAACUUAUCAAGAUGGUUG | 258 |
| S67-AS259-M1 | CCAUCUUGAUAAGUUUAACAUUGAC | 67 | GUCAAUGUUAAACUUAUCAAGAUGGUU | 259 |
| S68-AS260-M1 | CAUCUUGAUAAGUUUAACAUUGACA | 68 | UGUCAAUGUUAAACUUAUCAAGAUGGU | 260 |
| S69-AS261-M1 | AUCUUGAUAAGUUUAACAUUGACAA | 69 | UUGUCAAUGUUAAACUUAUCAAGAUGG | 261 |
| S70-AS262-M1 | GUUCACCACGGUUUCUGAAAUAACA | 70 | UGUUAUUUCAGAAACCGUGGUGAACAC | 262 |
| S71-AS263-M1 | CACCACGGUUUCUGAAAUAACAGCA | 71 | UGCUGUUAUUUCAGAAACCGUGGUGAA | 263 |
| S72-AS264-M1 | CCACGGUUUCUGAAAUAACAGCAAT | 72 | AUUGCUGUUAUUUCAGAAACCGUGGUG | 264 |
| S73-AS265-M1 | CACGGUUUCUGAAAUAACAGCAATA | 73 | UAUUGCUGUUAUUUCAGAAACCGUGGU | 265 |
| S74-AS266-M1 | CGGUUUCUGAAAUAACAGCAAUAGA | 74 | UCUAUUGCUGUUAUUUCAGAAACCGUG | 266 |
| S75-AS267-M1 | GGUUUCUGAAAUAACAGCAAUAGAA | 75 | UUCUAUUGCUGUUAUUUCAGAAACCGU | 267 |

TABLE 4-continued

GYS2 RNAi oligonucleotides

| App Name | Sense Sequence | S SEQ ID NO | Antisense Sequence | AS SEQ ID NO |
|---|---|---|---|---|
| S76-AS268-M1 | GUUUCUGAAAUAACAGCAAUAGAAG | 76 | CUUCUAUUGCUGUUAUUU CAGAAACCG | 268 |
| S77-AS269-M1 | CUGAAAUAACAGCAAUAGAAGCUGA | 77 | UCAGCUUCUAUUGCUGUU AUUUCAGAA | 269 |
| S78-AS270-M1 | AAGAGAAAGCCUGAUGUAGUUACTC | 78 | GAGUAACUACAUCAGGCU UUCUCUUCA | 270 |
| S79-AS271-M1 | AGAGAAAGCCUGAUGUAGUUACUCC | 79 | GGAGUAACUACAUCAGGC UUUCUCUUC | 271 |
| S80-AS272-M1 | GGCUUGAAUGUUAAGAAAUUUUCAG | 80 | CUGAAAAUUUCUUAACAU UCAAGCCGU | 272 |
| S81-AS273-M1 | GCUUGAAUGUUAAGAAAUUUUCAGC | 81 | GCUGAAAAUUUCUUAACA UUCAAGCCG | 273 |
| S82-AS274-M1 | CUUGAAUGUUAAGAAAUUUUCAGCA | 82 | UGCUGAAAAUUUCUUAAC AUUCAAGCC | 274 |
| S83-AS275-M1 | UUGAAUGUUAAGAAAUUUUCAGCAG | 83 | CUGCUGAAAAUUUCUUAA CAUUCAAGC | 275 |
| S84-AS276-M1 | UGAAUGUUAAGAAAUUUUCAGCAGT | 84 | ACUGCUGAAAAUUUCUUA ACAUUCAAG | 276 |
| S85-AS277-M1 | GAAUGUUAAGAAAUUUUCAGCAGTG | 85 | CACUGCUGAAAAUUUCUU AACAUUCAA | 277 |
| S86-AS278-M1 | AUGUUAAGAAAUUUUCAGCAGUGCA | 86 | UGCACUGCUGAAAAUUUC UUAACAUUC | 278 |
| S87-AS279-M1 | AGAAAUUUUCAGCAGUGCAUGAGTT | 87 | AACUCAUGCACUGCUGAAA AUUUCUUA | 279 |
| S88-AS280-M1 | AGCAGUGCAUGAGUUUCAAAAUCTA | 88 | UAGAUUUUGAAACUCAUG CACUGCUGA | 280 |
| S89-AS281-M1 | AGAUUUUGUUCGAGGUCAUUUCUAT | 89 | AUAGAAAUGACCUCGAACA AAAUCUUG | 281 |
| S90-AS282-M1 | GUUCGAGGUCAUUUCUAUGGUCATC | 90 | GAUGACCAUAGAAAUGACC UCGAACAA | 282 |
| S91-AS283-M1 | UUCGAGGUCAUUUCUAUGGUCAUCT | 91 | AGAUGACCAUAGAAAUGAC CUCGAACA | 283 |
| S92-AS284-M1 | UCGAGGUCAUUUCUAUGGUCAUCTC | 92 | GAGAUGACCAUAGAAAUG ACCUCGAAC | 284 |
| S93-AS285-M1 | CGAGGUCAUUUCUAUGGUCAUCUCG | 93 | CGAGAUGACCAUAGAAAUG ACCUCGAA | 285 |
| S94-AS286-M1 | GAGGUCAUUUCUAUGGUCAUCUCGA | 94 | UCGAGAUGACCAUAGAAA UGACCUCGA | 286 |
| S95-AS287-M1 | AGGUCAUUUCUAUGGUCAUCUCGAC | 95 | GUCGAGAUGACCAUAGAAA UGACCUCG | 287 |
| S96-AS288-M1 | GGUCAUUUCUAUGGUCAUCUCGACT | 96 | AGUCGAGAUGACCAUAGA AUGACCUC | 288 |
| S97-AS289-M1 | GUCAUUUCUAUGGUCAUCUCGACTT | 97 | AAGUCGAGAUGACCAUAGA AAUGACCU | 289 |
| S98-AS290-M1 | UGAAAAGACUUUGUUCCUUUUCATT | 98 | AAUGAAAAGGAACAAAGUC UUUUCAAG | 290 |
| S99-AS291-M1 | GAAAAGACUUUGUUCCUUUUCAUTG | 99 | CAAUGAAAAGGAACAAAGU CUUUUCAA | 291 |
| S100-AS292-M1 | AAAGACUUUGUUCCUUUUCAUUGCT | 100 | AGCAAUGAAAAGGAACAAA GUCUUUUC | 292 |

TABLE 4-continued

GYS2 RNAi oligonucleotides

| App Name | Sense Sequence | S SEQ ID NO | Antisense Sequence | AS SEQ ID NO |
| --- | --- | --- | --- | --- |
| S101-AS293-M1 | CUGAGGAUGCAUAAAAGUGACAUCA | 101 | UGAUGUCACUUUUAUGCAUCCUCAGCA | 293 |
| S102-AS294-M1 | GAGGAUGCAUAAAAGUGACAUCACA | 102 | UGUGAUGUCACUUUUAUGCAUCCUCAG | 294 |
| S103-AS295-M1 | UUUUUCAUUAUGCCUGCCAAGACAA | 103 | UUGUCUUGGCAGGCAUAAUGAAAAACA | 295 |
| S104-AS296-M1 | UCAUUAUGCCUGCCAAGACAAAUAA | 104 | UUAUUUGUCUUGGCAGGCAUAAUGAAA | 296 |
| S105-AS297-M1 | CAUUAUGCCUGCCAAGACAAAUAAT | 105 | AUUAUUUGUCUUGGCAGGCAUAAUGAA | 297 |
| S106-AS298-M1 | AUUAUGCCUGCCAAGACAAAUAATT | 106 | AAUUAUUUGUCUUGGCAGGCAUAAUGA | 298 |
| S107-AS299-M1 | AUGCCUGCCAAGACAAAUAAUUUCA | 107 | UGAAAUUAUUUGUCUUGGCAGGCAUAA | 299 |
| S108-AS300-M1 | AAUUUCAACGUGGAAACCCUGAAAG | 108 | CUUUCAGGGUUUCCACGUUGAAAUUAU | 300 |
| S109-AS301-M1 | AUUUCAACGUGGAAACCCUGAAAGG | 109 | CCUUUCAGGGUUUCCACGUUGAAAUUA | 301 |
| S110-AS302-M1 | UUUCAACGUGGAAACCCUGAAAGGA | 110 | UCCUUUCAGGGUUUCCACGUUGAAAUU | 302 |
| S111-AS303-M1 | UUCAACGUGGAAACCCUGAAAGGAC | 111 | GUCCUUUCAGGGUUUCCACGUUGAAAU | 303 |
| S112-AS304-M1 | UCAACGUGGAAACCCUGAAAGGACA | 112 | UGUCCUUUCAGGGUUUCCACGUUGAAA | 304 |
| S113-AS305-M1 | UUGCACAUUCUGUGAAGGAAAAGUU | 113 | AACUUUUCCUUCACAGAAUGUGCAACA | 305 |
| S114-AS306-M1 | UGCACAUUCUGUGAAGGAAAAGUUT | 114 | AAACUUUUCCUUCACAGAAUGUGCAAC | 306 |
| S115-AS307-M1 | GCACAUUCUGUGAAGGAAAAGUUTG | 115 | CAAACUUUUCCUUCACAGAAUGUGCAA | 307 |
| S116-AS308-M1 | AUUCUGUGAAGGAAAAGUUUGGAAA | 116 | UUUCCAAACUUUUCCUUCACAGAAUGU | 308 |
| S117-AS309-M1 | GUGAAGGAAAAGUUUGGAAAAAAAC | 117 | GUUUUUUUCCAAACUUUUCCUUCACAG | 309 |
| S118-AS310-M1 | GAAAAAACUCUAUGAUGCAUUAUT | 118 | AAUAAUGCAUCAUAGAGUUUUUUCCA | 310 |
| S119-AS311-M1 | AAAAAACUCUAUGAUGCAUUAUTA | 119 | UAAUAAUGCAUCAUAGAGUUUUUUUCC | 311 |
| S120-AS312-M1 | AAAAACUCUAUGAUGCAUUAUUAA | 120 | UUAAUAAUGCAUCAUAGAGUUUUUUUC | 312 |
| S121-AS313-M1 | AAAACUCUAUGAUGCAUUAUUAAG | 121 | CUUAAUAAUGCAUCAUAGAGUUUUUUU | 313 |
| S122-AS314-M1 | UUAUUAAGAGGAGAAAUUCCUGACC | 122 | GGUCAGGAAUUUCUCCUCUUAAUAAUG | 314 |
| S123-AS315-M1 | UAUUAAGAGGAGAAAUUCCUGACCT | 123 | AGGUCAGGAAUUUCUCCUCUUAAUAAU | 315 |
| S124-AS316-M1 | AUUAAGAGGAGAAAUUCCUGACCTG | 124 | CAGGUCAGGAAUUUCUCCUCUUAAUAA | 316 |
| S125-AS317-M1 | UUAAGAGGAGAAAUUCCUGACCUGA | 125 | UCAGGUCAGGAAUUUCUCCUCUUAAUA | 317 |

TABLE 4-continued

GYS2 RNAi oligonucleotides

| App Name | Sense Sequence | S SEQ ID NO | Antisense Sequence | AS SEQ ID NO |
|---|---|---|---|---|
| S126-AS318-M1 | UAAGAGGAGAAAUUCCUGACCUGAA | 126 | UUCAGGUCAGGAAUUUCUCCUCUUAAU | 318 |
| S127-AS319-M1 | AAGAGGAGAAAUUCCUGACCUGAAC | 127 | GUUCAGGUCAGGAAUUUCUCCUCUUAA | 319 |
| S128-AS320-M1 | CGAGAUGAUCUAACAAUUAUGAAAA | 128 | UUUUCAUAAUUGUUAGAUCAUCUCGAU | 320 |
| S129-AS321-M1 | AGAUGAUCUAACAAUUAUGAAAGA | 129 | UCUUUCAUAAUUGUUAGAUCAUCUCG | 321 |
| S130-AS322-M1 | GAUGAUCUAACAAUUAUGAAAGAG | 130 | CUCUUUCAUAAUUGUUAGAUCAUCUC | 322 |
| S131-AS323-M1 | AUGAUCUAACAAUUAUGAAAGAGC | 131 | GCUCUUUCAUAAUUGUUAGAUCAUCU | 323 |
| S132-AS324-M1 | ACAAUUAUGAAAGAGCCAUCUUTT | 132 | AAAAGAUGGCUCUUUUCAUAAUUGUUA | 324 |
| S133-AS325-M1 | GAAAAGAGCCAUCUUUUCAACUCAG | 133 | CUGAGUUGAAAAGAUGGCUCUUUUCAU | 325 |
| S134-AS326-M1 | CCCAUCCUCAGCACCAUUAGACGGA | 134 | UCCGUCUAAUGGUGCUGAGGAUGGGU | 326 |
| S135-AS327-M1 | CCAUCCUCAGCACCAUUAGACGGAT | 135 | AUCCGUCUAAUGGUGCUGAGGAUGGGG | 327 |
| S136-AS328-M1 | CAUCCUCAGCACCAUUAGACGGATT | 136 | AAUCCGUCUAAUGGUGCUGAGGAUGGG | 328 |
| S137-AS329-M1 | AUCCUCAGCACCAUUAGACGGAUTG | 137 | CAAUCCGUCUAAUGGUGCUGAGGAUGG | 329 |
| S138-AS330-M1 | UCCUCAGCACCAUUAGACGGAUUGG | 138 | CCAAUCCGUCUAAUGGUGCUGAGGAUG | 330 |
| S139-AS331-M1 | CCCAUGGACUAUGAAGAGUUUGUTA | 139 | UAACAAACUCUUCAUAGUCCAUGGGUA | 331 |
| S140-AS332-M1 | CCAUGGACUAUGAAGAGUUUGUUAG | 140 | CUAACAAACUCUUCAUAGUCCAUGGGU | 332 |
| S141-AS333-M1 | CUUGGAGUAUUUCCAUCAUACUATG | 141 | CAUAGUAUGAUGGAAAUACUCCAAGAU | 333 |
| S142-AS334-M1 | UGGAGUAUUUCCAUCAUACUAUGAA | 142 | UUCAUAGUAUGAUGGAAAUACUCCAAG | 334 |
| S143-AS335-M1 | GGAGUAUUUCCAUCAUACUAUGAAC | 143 | GUUCAUAGUAUGAUGGAAAUACUCCAA | 335 |
| S144-AS336-M1 | GAGUAUUUCCAUCAUACUAUGAACC | 144 | GGUUCAUAGUAUGAUGGAAAUACUCCA | 336 |
| S145-AS337-M1 | UAUUUCCAUCAUACUAUGAACCCTG | 145 | CAGGGUUCAUAGUAUGAUGGAAAUACU | 337 |
| S146-AS338-M1 | AUACUCCAGCUGAAUGCACUGUGAT | 146 | AUCACAGUGCAUUCAGCUGGAGUAUAA | 338 |
| S147-AS339-M1 | GGCAGAUAUUACCAGCAUGCCAGAC | 147 | GUCUGGCAUGCUGGUAAUAUCUGCCUA | 339 |
| S148-AS340-M1 | GCAGAUAUUACCAGCAUGCCAGACA | 148 | UGUCUGGCAUGCUGGUAAUAUCUGCCU | 340 |
| S149-AS341-M1 | CAGAUAUUACCAGCAUGCCAGACAC | 149 | GUGUCUGGCAUGCUGGUAAUAUCUGCC | 341 |
| S150-AS342-M1 | AGAUAUUACCAGCAUGCCAGACACC | 150 | GGUGUCUGGCAUGCUGGUAAUAUCUGC | 342 |

TABLE 4-continued

GYS2 RNAi oligonucleotides

| App Name | Sense Sequence | S SEQ ID NO | Antisense Sequence | AS SEQ ID NO |
|---|---|---|---|---|
| S151-AS343-M1 | GAUAUUACCAGCAUGCCAGACACCT | 151 | AGGUGUCUGGCAUGCUGGUAAUAUCUG | 343 |
| S152-AS344-M1 | AUAUUACCAGCAUGCCAGACACCTG | 152 | CAGGUGUCUGGCAUGCUGGUAAUAUCU | 344 |
| S153-AS345-M1 | UAUUACCAGCAUGCCAGACACCUGA | 153 | UCAGGUGUCUGGCAUGCUGGUAAUAUC | 345 |
| S154-AS346-M1 | AUUACCAGCAUGCCAGACACCUGAC | 154 | GUCAGGUGUCUGGCAUGCUGGUAAUAU | 346 |
| S155-AS347-M1 | UUACCAGCAUGCCAGACACCUGACA | 155 | UGUCAGGUGUCUGGCAUGCUGGUAAUA | 347 |
| S156-AS348-M1 | UACCAGCAUGCCAGACACCUGACAT | 156 | AUGUCAGGUGUCUGGCAUGCUGGUAAU | 348 |
| S157-AS349-M1 | ACCAGCAUGCCAGACACCUGACATT | 157 | AAUGUCAGGUGUCUGGCAUGCUGGUAA | 349 |
| S158-AS350-M1 | CCAGCAUGCCAGACACCUGACAUTA | 158 | UAAUGUCAGGUGUCUGGCAUGCUGGUA | 350 |
| S159-AS351-M1 | CAGCAUGCCAGACACCUGACAUUAA | 159 | UUAAUGUCAGGUGUCUGGCAUGCUGGU | 351 |
| S160-AS352-M1 | AGCAUGCCAGACACCUGACAUUAAG | 160 | CUUAAUGUCAGGUGUCUGGCAUGCUGG | 352 |
| S161-AS353-M1 | GCAUGCCAGACACCUGACAUUAAGC | 161 | GCUUAAUGUCAGGUGUCUGGCAUGCUG | 353 |
| S162-AS354-M1 | UGCCAGACACCUGACAUUAAGCAGA | 162 | UCUGCUUAAUGUCAGGUGUCUGGCAUG | 354 |
| S163-AS355-M1 | CCUGACAUUAAGCAGAGCUUUUCCA | 163 | UGGAAAAGCUCUGCUUAAUGUCAGGUG | 355 |
| S164-AS356-M1 | AAGCAGAGCUUUUCCAGAUAAAUTC | 164 | GAAUUUAUCUGGAAAAGCUCUGCUUAA | 356 |
| S165-AS357-M1 | GCAGAGCUUUUCCAGAUAAAUUCCA | 165 | UGGAAUUUAUCUGGAAAAGCUCUGCUU | 357 |
| S166-AS358-M1 | CCAGAUAAAUUCCAUGUGGAACUAA | 166 | UUAGUUCCACAUGGAAUUUAUCUGGAA | 358 |
| S167-AS359-M1 | CAGAUAAAUUCCAUGUGGAACUAAC | 167 | GUUAGUUCCACAUGGAAUUUAUCUGGA | 359 |
| S168-AS360-M1 | UCCUCAGUACCACCUUCUCCUUCAG | 168 | CUGAAGGAGAAGGUGGUACUGAGGAAG | 360 |
| S169-AS361-M1 | CCUCAGUACCACCUUCUCCUUCAGG | 169 | CCUGAAGGAGAAGGUGGUACUGAGGAA | 361 |
| S170-AS362-M1 | GAAAGGGAUCGGUUAAAUAUCAAGT | 170 | ACUUGAUAUUUAACCGAUCCCUUUCAG | 362 |
| S171-AS363-M1 | AGGGAUCGGUUAAAUAUCAAGUCAC | 171 | GUGACUUGAUAUUUAACCGAUCCCUUU | 363 |
| S172-AS364-M1 | AUCGGUUAAAUAUCAAGUCACCATT | 172 | AAUGGUGACUUGAUAUUUAACCGAUCC | 364 |
| S173-AS365-M1 | GGUUAAAUAUCAAGUCACCAUUUTC | 173 | GAAAAUGGUGACUUGAUAUUUAACCGA | 365 |
| S174-AS366-M1 | GUUAAAUAUCAAGUCACCAUUUUCA | 174 | UGAAAAUGGUGACUUGAUAUUUAACCG | 366 |
| S175-AS367-M1 | AAAUAUCAAGUCACCAUUUUCACTG | 175 | CAGUGAAAAUGGUGACUUGAUAUUUAA | 367 |

TABLE 4-continued

GYS2 RNAi oligonucleotides

| App Name | Sense Sequence | S SEQ ID NO | Antisense Sequence | AS SEQ ID NO |
|---|---|---|---|---|
| S176-AS368-M1 | AAGAAAAAGCUGCAUGGUGAAUAUA | 176 | UAUAUUCACCAUGCAGCUUUUUCUUCC | 368 |
| S177-AS369-M1 | AGAAAAAGCUGCAUGGUGAAUAUAA | 177 | UUAUAUUCACCAUGCAGCUUUUUCUUC | 369 |
| S178-AS370-M1 | AAAAAGCUGCAUGGUGAAUAUAAGA | 178 | UCUUAUAUUCACCAUGCAGCUUUUUCU | 370 |
| S179-AS371-M1 | AAAAGCUGCAUGGUGAAUAUAAGAA | 179 | UUCUUAUAUUCACCAUGCAGCUUUUUC | 371 |
| S180-AS372-M1 | AAGCUGCAUGGUGAAUAUAAGAACT | 180 | AGUUCUUAUAUUCACCAUGCAGCUUUU | 372 |
| S181-AS373-M1 | GCUGCAUGGUGAAUAUAAGAACUGA | 181 | UCAGUUCUUAUAUUCACCAUGCAGCUU | 373 |
| S182-AS374-M1 | CUGCAUGGUGAAUAUAAGAACUGAA | 182 | UUCAGUUCUUAUAUUCACCAUGCAGCU | 374 |
| S183-AS375-M1 | GCAUGGUGAAUAUAAGAACUGAAUU | 183 | AAUUCAGUUCUUAUAUUCACCAUGCAG | 375 |
| S184-AS376-M1 | CAUGGUGAAUAUAAGAACUGAAUUC | 184 | GAAUUCAGUUCUUAUAUUCACCAUGCA | 376 |
| S185-AS377-M1 | AUGGUGAAUAUAAGAACUGAAUUCU | 185 | AGAAUUCAGUUCUUAUAUUCACCAUGC | 377 |
| S186-AS378-M1 | UGGUGAAUAUAAGAACUGAAUUCUA | 186 | UAGAAUUCAGUUCUUAUAUUCACCAUG | 378 |
| S187-AS379-M1 | GGUGAAUAUAAGAACUGAAUUCUAC | 187 | GUAGAAUUCAGUUCUUAUAUUCACCAU | 379 |
| S188-AS380-M1 | GUGAAUAUAAGAACUGAAUUCUACA | 188 | UGUAGAAUUCAGUUCUUAUAUUCACCA | 380 |
| S189-AS381-M1 | AAUAUAAGAACUGAAUUCUACAUGT | 189 | ACAUGUAGAAUUCAGUUCUUAUAUUCA | 381 |
| S190-AS382-M1 | AUAUAAGAACUGAAUUCUACAUGTG | 190 | CACAUGUAGAAUUCAGUUCUUAUAUUC | 382 |
| S191-AS383-M1 | AUAAGAACUGAAUUCUACAUGUGCT | 191 | AGCACAUGUAGAAUUCAGUUCUUAUAU | 383 |
| S192-AS384-M1 | AAGAACUGAAUUCUACAUGUGCUGC | 192 | GCAGCACAUGUAGAAUUCAGUUCUUAU | 384 |
| S385-AS417-M2 | AGGUGCAUUUUGGAAGAUGGGCAGCCGAAAGGCUGC | 385 | CCAUCUUCCAAAAUGCACCUGG | 417 |
| S385-AS417-M3 | AGGUGCAUUUUGGAAGAUGGGCAGCCGAAAGGCUGC | 385 | CCAUCUUCCAAAAUGCACCUGG | 417 |
| S385-AS417-M4 | AGGUGCAUUUUGGAAGAUGGGCAGCCGAAAGGCUGC | 385 | CCAUCUUCCAAAAUGCACCUGG | 417 |
| S385-AS417-M5 | AGGUGCAUUUUGGAAGAUGGGCAGCCGAAAGGCUGC | 385 | CCAUCUUCCAAAAUGCACCUGG | 417 |
| S385-AS417-M6 | AGGUGCAUUUUGGAAGAUGGGCAGCCGAAAGGCUGC | 385 | CCAUCUUCCAAAAUGCACCUGG | 417 |
| S385-AS417-M7 | AGGUGCAUUUUGGAAGAUGGGCAGCCGAAAGGCUGC | 385 | CCAUCUUCCAAAAUGCACCUGG | 417 |
| S385-AS417-M8 | AGGUGCAUUUUGGAAGAUGGGCAGCCGAAAGGCUGC | 385 | CCAUCUUCCAAAAUGCACCUGG | 417 |
| S385-AS417-M9 | AGGUGCAUUUUGGAAGAUGGGCAGCCGAAAGGCUGC | 385 | CCAUCUUCCAAAAUGCACCUGG | 417 |

TABLE 4-continued

GYS2 RNAi oligonucleotides

| App Name | Sense Sequence | S SEQ ID NO | Antisense Sequence | AS SEQ ID NO |
|---|---|---|---|---|
| S385-AS417-M10 | AGGUGCAUUUUGGAAGAUGGGCAGCCGAAAGGCUGC | 385 | CCAUCUUCCAAAAUGCACCUGG | 417 |
| S385-AS417-M11 | AGGUGCAUUUUGGAAGAUGGGCAGCCGAAAGGCUGC | 385 | CCAUCUUCCAAAAUGCACCUGG | 417 |
| S386-AS418-M12 | AGGUGCAUUUUGGAAGAUGGCAGCCGAAAGGCUGC | 386 | CAUCUUCCAAAAUGCACCUGG | 418 |
| S386-AS418-M13 | AGGUGCAUUUUGGAAGAUGGCAGCCGAAAGGCUGC | 386 | CAUCUUCCAAAAUGCACCUGG | 418 |
| S387-AS419-M2 | GGUGCAUUUUGGAAGAUGGCGCAGCCGAAAGGCUGC | 387 | GCCAUCUUCCAAAAUGCACCUG | 419 |
| S387-AS419-M3 | GGUGCAUUUUGGAAGAUGGCGCAGCCGAAAGGCUGC | 387 | GCCAUCUUCCAAAAUGCACCUG | 419 |
| S387-AS419-M4 | GGUGCAUUUUGGAAGAUGGCGCAGCCGAAAGGCUGC | 387 | GCCAUCUUCCAAAAUGCACCUG | 419 |
| S387-AS419-M5 | GGUGCAUUUUGGAAGAUGGCGCAGCCGAAAGGCUGC | 387 | GCCAUCUUCCAAAAUGCACCUG | 419 |
| S387-AS419-M6 | GGUGCAUUUUGGAAGAUGGCGCAGCCGAAAGGCUGC | 387 | GCCAUCUUCCAAAAUGCACCUG | 419 |
| S387-AS419-M7 | GGUGCAUUUUGGAAGAUGGCGCAGCCGAAAGGCUGC | 387 | GCCAUCUUCCAAAAUGCACCUG | 419 |
| S387-AS419-M8 | GGUGCAUUUUGGAAGAUGGCGCAGCCGAAAGGCUGC | 387 | GCCAUCUUCCAAAAUGCACCUG | 419 |
| S387-AS419-M9 | GGUGCAUUUUGGAAGAUGGCGCAGCCGAAAGGCUGC | 387 | GCCAUCUUCCAAAAUGCACCUG | 419 |
| S387-AS419-M10 | GGUGCAUUUUGGAAGAUGGCGCAGCCGAAAGGCUGC | 387 | GCCAUCUUCCAAAAUGCACCUG | 419 |
| S387-AS419-M11 | GGUGCAUUUUGGAAGAUGGCGCAGCCGAAAGGCUGC | 387 | GCCAUCUUCCAAAAUGCACCUG | 419 |
| S388-AS420-M12 | GGUGCAUUUUGGAAGAUGGGCAGCCGAAAGGCUGC | 388 | CCAUCUUCCAAAAUGCACCUG | 420 |
| S388-AS420-M13 | GGUGCAUUUUGGAAGAUGGGCAGCCGAAAGGCUGC | 388 | CCAUCUUCCAAAAUGCACCUG | 420 |
| S389-AS421-M2 | AAGGAAGUCCUUAUGUGGUAGCAGCCGAAAGGCUGC | 389 | UACCACAUAAGGACUUCCUUCU | 421 |
| S389-AS421-M3 | AAGGAAGUCCUUAUGUGGUAGCAGCCGAAAGGCUGC | 389 | UACCACAUAAGGACUUCCUUCU | 421 |
| S389-AS421-M4 | AAGGAAGUCCUUAUGUGGUAGCAGCCGAAAGGCUGC | 389 | UACCACAUAAGGACUUCCUUCU | 421 |
| S389-AS421-M5 | AAGGAAGUCCUUAUGUGGUAGCAGCCGAAAGGCUGC | 389 | UACCACAUAAGGACUUCCUUCU | 421 |
| S389-AS422-M6 | AAGGAAGUCCUUAUGUGGUAGCAGCCGAAAGGCUGC | 389 | UACCACAUAAGGACUUCCTUCU | 422 |
| S389-AS421-M7 | AAGGAAGUCCUUAUGUGGUAGCAGCCGAAAGGCUGC | 389 | UACCACAUAAGGACUUCCUUCU | 421 |
| S389-AS421-M8 | AAGGAAGUCCUUAUGUGGUAGCAGCCGAAAGGCUGC | 389 | UACCACAUAAGGACUUCCUUCU | 421 |
| S389-AS421-M9 | AAGGAAGUCCUUAUGUGGUAGCAGCCGAAAGGCUGC | 389 | UACCACAUAAGGACUUCCUUCU | 421 |
| S389-AS421-M10 | AAGGAAGUCCUUAUGUGGUAGCAGCCGAAAGGCUGC | 389 | UACCACAUAAGGACUUCCUUCU | 421 |

TABLE 4-continued

GYS2 RNAi oligonucleotides

| App Name | Sense Sequence | S SEQ ID NO | Antisense Sequence | AS SEQ ID NO |
|---|---|---|---|---|
| S389-AS421-M11 | AAGGAAGUCCUUAUGUGGUAGCAGCCGAAAGGCUGC | 389 | UACCACAUAAGGACUUCCUUCU | 421 |
| S390-AS423-M12 | AAGGAAGUCCUUAUGUGGUGCAGCCGAAAGGCUGC | 390 | ACCACAUAAGGACUUCCTUCU | 423 |
| S390-AS424-M13 | AAGGAAGUCCUUAUGUGGUGCAGCCGAAAGGCUGC | 390 | ACCACAUAAGGACUUCCUUCU | 424 |
| S391-AS425-M2 | AUGAUAUGCUGAUAUUUGGAGCAGCCGAAAGGCUGC | 391 | UCCAAAUAUCAGCAUAUCAUUG | 425 |
| S391-AS425-M3 | AUGAUAUGCUGAUAUUUGGAGCAGCCGAAAGGCUGC | 391 | UCCAAAUAUCAGCAUAUCAUUG | 425 |
| S391-AS425-M4 | AUGAUAUGCUGAUAUUUGGAGCAGCCGAAAGGCUGC | 391 | UCCAAAUAUCAGCAUAUCAUUG | 425 |
| S391-AS425-M5 | AUGAUAUGCUGAUAUUUGGAGCAGCCGAAAGGCUGC | 391 | UCCAAAUAUCAGCAUAUCAUUG | 425 |
| S391-AS426-M6 | AUGAUAUGCUGAUAUUUGGAGCAGCCGAAAGGCUGC | 391 | UCCAAAUAUCAGCAUATCAUUG | 426 |
| S391-AS425-M7 | AUGAUAUGCUGAUAUUUGGAGCAGCCGAAAGGCUGC | 391 | UCCAAAUAUCAGCAUAUCAUUG | 425 |
| S391-AS425-M8 | AUGAUAUGCUGAUAUUUGGAGCAGCCGAAAGGCUGC | 391 | UCCAAAUAUCAGCAUAUCAUUG | 425 |
| S391-AS425-M9 | AUGAUAUGCUGAUAUUUGGAGCAGCCGAAAGGCUGC | 391 | UCCAAAUAUCAGCAUAUCAUUG | 425 |
| S391-AS425-M10 | AUGAUAUGCUGAUAUUUGGAGCAGCCGAAAGGCUGC | 391 | UCCAAAUAUCAGCAUAUCAUUG | 425 |
| S391-AS425-M11 | AUGAUAUGCUGAUAUUUGGAGCAGCCGAAAGGCUGC | 391 | UCCAAAUAUCAGCAUAUCAUUG | 425 |
| S392-AS427-M12 | AUGAUAUGCUGAUAUUUGGGCAGCCGAAAGGCUGC | 392 | CCAAAUAUCAGCAUATCAUUG | 427 |
| S392-AS428-M13 | AUGAUAUGCUGAUAUUUGGGCAGCCGAAAGGCUGC | 392 | CCAAAUAUCAGCAUAUCAUUG | 428 |
| S393-AS429-M2 | AGCAAAUAUUGAUUUCUACAGCAGCCGAAAGGCUGC | 393 | UGUAGAAAUCAAUAUUUGCUGC | 429 |
| S393-AS429-M3 | AGCAAAUAUUGAUUUCUACAGCAGCCGAAAGGCUGC | 393 | UGUAGAAAUCAAUAUUUGCUGC | 429 |
| S393-AS429-M4 | AGCAAAUAUUGAUUUCUACAGCAGCCGAAAGGCUGC | 393 | UGUAGAAAUCAAUAUUUGCUGC | 429 |
| S393-AS429-M5 | AGCAAAUAUUGAUUUCUACAGCAGCCGAAAGGCUGC | 393 | UGUAGAAAUCAAUAUUUGCUGC | 429 |
| S393-AS430-M6 | AGCAAAUAUUGAUUUCUACAGCAGCCGAAAGGCUGC | 393 | UGUAGAAAUCAATAUUTGCUGC | 430 |
| S393-AS429-M7 | AGCAAAUAUUGAUUUCUACAGCAGCCGAAAGGCUGC | 393 | UGUAGAAAUCAAUAUUUGCUGC | 429 |
| S393-AS429-M8 | AGCAAAUAUUGAUUUCUACAGCAGCCGAAAGGCUGC | 393 | UGUAGAAAUCAAUAUUUGCUGC | 429 |
| S393-AS429-M9 | AGCAAAUAUUGAUUUCUACAGCAGCCGAAAGGCUGC | 393 | UGUAGAAAUCAAUAUUUGCUGC | 429 |
| S393-AS429-M10 | AGCAAAUAUUGAUUUCUACAGCAGCCGAAAGGCUGC | 393 | UGUAGAAAUCAAUAUUUGCUGC | 429 |
| S393-AS429-M11 | AGCAAAUAUUGAUUUCUACAGCAGCCGAAAGGCUGC | 393 | UGUAGAAAUCAAUAUUUGCUGC | 429 |

TABLE 4-continued

GYS2 RNAi oligonucleotides

| App Name | Sense Sequence | S SEQ ID NO | Antisense Sequence | AS SEQ ID NO |
|---|---|---|---|---|
| S394-AS431-M12 | AGCAAAUAUUGAUUUCUACGCAGCCGAAAGGCUGC | 394 | GUAGAAAUCAAUAUUGCUGC | 431 |
| S394-AS432-M13 | AGCAAAUAUUGAUUUCUACGCAGCCGAAAGGCUGC | 394 | GUAGAAAUCAAUAUUUGCUGC | 432 |
| S395-AS433-M2 | CCACGGUUUCUGAAAUAACAGCAGCCGAAAGGCUGC | 395 | UGUUAUUUCAGAAACCGUGGUG | 433 |
| S395-AS433-M3 | CCACGGUUUCUGAAAUAACAGCAGCCGAAAGGCUGC | 395 | UGUUAUUUCAGAAACCGUGGUG | 433 |
| S395-AS433-M4 | CCACGGUUUCUGAAAUAACAGCAGCCGAAAGGCUGC | 395 | UGUUAUUUCAGAAACCGUGGUG | 433 |
| S395-AS433-M5 | CCACGGUUUCUGAAAUAACAGCAGCCGAAAGGCUGC | 395 | UGUUAUUUCAGAAACCGUGGUG | 433 |
| S395-AS433-M6 | CCACGGUUUCUGAAAUAACAGCAGCCGAAAGGCUGC | 395 | UGUUAUUUCAGAAACCGUGGUG | 433 |
| S395-AS433-M7 | CCACGGUUUCUGAAAUAACAGCAGCCGAAAGGCUGC | 395 | UGUUAUUUCAGAAACCGUGGUG | 433 |
| S395-AS433-M8 | CCACGGUUUCUGAAAUAACAGCAGCCGAAAGGCUGC | 395 | UGUUAUUUCAGAAACCGUGGUG | 433 |
| S395-AS433-M9 | CCACGGUUUCUGAAAUAACAGCAGCCGAAAGGCUGC | 395 | UGUUAUUUCAGAAACCGUGGUG | 433 |
| S395-AS433-M10 | CCACGGUUUCUGAAAUAACAGCAGCCGAAAGGCUGC | 395 | UGUUAUUUCAGAAACCGUGGUG | 433 |
| S395-AS433-M11 | CCACGGUUUCUGAAAUAACAGCAGCCGAAAGGCUGC | 395 | UGUUAUUUCAGAAACCGUGGUG | 433 |
| S396-AS434-M12 | CCACGGUUUCUGAAAUAACGCAGCCGAAAGGCUGC | 396 | GUAUUUCAGAAACCGUGGUG | 434 |
| S396-AS435-M13 | CCACGGUUUCUGAAAUAACGCAGCCGAAAGGCUGC | 396 | GUUAUUUCAGAAACCGUGGUG | 435 |
| S397-AS436-M2 | CUUGAAUGUUAAGAAAUUUGCAGCCGAAAGGCUGC | 397 | AAAAUUUCUUAACAUUCAAGCC | 436 |
| S397-AS436-M3 | CUUGAAUGUUAAGAAAUUUGCAGCCGAAAGGCUGC | 397 | AAAAUUUCUUAACAUUCAAGCC | 436 |
| S397-AS436-M4 | CUUGAAUGUUAAGAAAUUUGCAGCCGAAAGGCUGC | 397 | AAAAUUUCUUAACAUUCAAGCC | 436 |
| S397-AS436-M5 | CUUGAAUGUUAAGAAAUUUGCAGCCGAAAGGCUGC | 397 | AAAAUUUCUUAACAUUCAAGCC | 436 |
| S397-AS436-M6 | CUUGAAUGUUAAGAAAUUUGCAGCCGAAAGGCUGC | 397 | AAAAUUUCUUAACAUUCAAGCC | 436 |
| S397-AS436-M7 | CUUGAAUGUUAAGAAAUUUGCAGCCGAAAGGCUGC | 397 | AAAAUUUCUUAACAUUCAAGCC | 436 |
| S397-AS436-M8 | CUUGAAUGUUAAGAAAUUUGCAGCCGAAAGGCUGC | 397 | AAAAUUUCUUAACAUUCAAGCC | 436 |
| S397-AS436-M9 | CUUGAAUGUUAAGAAAUUUGCAGCCGAAAGGCUGC | 397 | AAAAUUUCUUAACAUUCAAGCC | 436 |
| S397-AS436-M10 | CUUGAAUGUUAAGAAAUUUGCAGCCGAAAGGCUGC | 397 | AAAAUUUCUUAACAUUCAAGCC | 436 |
| S397-AS436-M11 | CUUGAAUGUUAAGAAAUUUGCAGCCGAAAGGCUGC | 397 | AAAAUUUCUUAACAUUCAAGCC | 436 |
| S398-AS437-M12 | CUUGAAUGUUAAGAAAUUUGCAGCCGAAAGGCUGC | 398 | AAAUUUCUUAACAUUCAAGCC | 437 |

TABLE 4-continued

GYS2 RNAi oligonucleotides

| App Name | Sense Sequence | S SEQ ID NO | Antisense Sequence | AS SEQ ID NO |
|---|---|---|---|---|
| S398-AS437-M13 | CUUGAAUGUUAAGAAAUUUGCAGCCGAAAGGCUGC | 398 | AAAUUUCUUAACAUUCAAGCC | 437 |
| S399-AS438-M2 | UGAAUGUUAAGAAAUUUUCAGCAGCCGAAAGGCUGC | 399 | UGAAAAUUUCUUAACAUUCAAG | 438 |
| S399-AS438-M3 | UGAAUGUUAAGAAAUUUUCAGCAGCCGAAAGGCUGC | 399 | UGAAAAUUUCUUAACAUUCAAG | 438 |
| S399-AS438-M4 | UGAAUGUUAAGAAAUUUUCAGCAGCCGAAAGGCUGC | 399 | UGAAAAUUUCUUAACAUUCAAG | 438 |
| S399-AS438-M5 | UGAAUGUUAAGAAAUUUUCAGCAGCCGAAAGGCUGC | 399 | UGAAAAUUUCUUAACAUUCAAG | 438 |
| S399-AS439-M6 | UGAAUGUUAAGAAAUUUUCAGCAGCCGAAAGGCUGC | 399 | UGAAAAUUUCUUAACAUUCAAG | 439 |
| S399-AS438-M7 | UGAAUGUUAAGAAAUUUUCAGCAGCCGAAAGGCUGC | 399 | UGAAAAUUUCUUAACAUUCAAG | 438 |
| S399-AS438-M8 | UGAAUGUUAAGAAAUUUUCAGCAGCCGAAAGGCUGC | 399 | UGAAAAUUUCUUAACAUUCAAG | 438 |
| S399-AS438-M9 | UGAAUGUUAAGAAAUUUUCAGCAGCCGAAAGGCUGC | 399 | UGAAAAUUUCUUAACAUUCAAG | 438 |
| S399-AS438-M10 | UGAAUGUUAAGAAAUUUUCAGCAGCCGAAAGGCUGC | 399 | UGAAAAUUUCUUAACAUUCAAG | 438 |
| S399-AS438-M11 | UGAAUGUUAAGAAAUUUUCAGCAGCCGAAAGGCUGC | 399 | UGAAAAUUUCUUAACAUUCAAG | 438 |
| S400-AS440-M12 | UGAAUGUUAAGAAAUUUUCGCAGCCGAAAGGCUGC | 400 | GAAAAUUUCUUAACAUUCAAG | 440 |
| S400-AS441-M13 | UGAAUGUUAAGAAAUUUUCGCAGCCGAAAGGCUGC | 400 | GAAAAUUUCUUAACAUUCAAG | 441 |
| S401-AS442-M2 | CGAGGUCAUUUCUAUGGUCAGCAGCCGAAAGGCUGC | 401 | UGACCAUAGAAAUGACCUCGAA | 442 |
| S401-AS442-M3 | CGAGGUCAUUUCUAUGGUCAGCAGCCGAAAGGCUGC | 401 | UGACCAUAGAAAUGACCUCGAA | 442 |
| S401-AS442-M4 | CGAGGUCAUUUCUAUGGUCAGCAGCCGAAAGGCUGC | 401 | UGACCAUAGAAAUGACCUCGAA | 442 |
| S401-AS442-M5 | CGAGGUCAUUUCUAUGGUCAGCAGCCGAAAGGCUGC | 401 | UGACCAUAGAAAUGACCUCGAA | 442 |
| S401-AS443-M6 | CGAGGUCAUUUCUAUGGUCAGCAGCCGAAAGGCUGC | 401 | UGACCAUAGAAATGACCUCGAA | 443 |
| S401-AS442-M7 | CGAGGUCAUUUCUAUGGUCAGCAGCCGAAAGGCUGC | 401 | UGACCAUAGAAAUGACCUCGAA | 442 |
| S401-AS442-M8 | CGAGGUCAUUUCUAUGGUCAGCAGCCGAAAGGCUGC | 401 | UGACCAUAGAAAUGACCUCGAA | 442 |
| S401-AS442-M9 | CGAGGUCAUUUCUAUGGUCAGCAGCCGAAAGGCUGC | 401 | UGACCAUAGAAAUGACCUCGAA | 442 |
| S401-AS442-M10 | CGAGGUCAUUUCUAUGGUCAGCAGCCGAAAGGCUGC | 401 | UGACCAUAGAAAUGACCUCGAA | 442 |
| S401-AS442-M11 | CGAGGUCAUUUCUAUGGUCAGCAGCCGAAAGGCUGC | 401 | UGACCAUAGAAAUGACCUCGAA | 442 |
| S402-AS444-M12 | CGAGGUCAUUUCUAUGGUCGCAGCCGAAAGGCUGC | 402 | GACCAUAGAAATGACCUCGAA | 444 |
| S402-AS445-M13 | CGAGGUCAUUUCUAUGGUCGCAGCCGAAAGGCUGC | 402 | GACCAUAGAAAUGACCUCGAA | 445 |

TABLE 4-continued

GYS2 RNAi oligonucleotides

| App Name | Sense Sequence | S SEQ ID NO | Antisense Sequence | AS SEQ ID NO |
|---|---|---|---|---|
| S403-AS446-M2 | AUUCUGUGAAGGAAAAGUUUGCAGCCGAAAGGCUGC | 403 | AAACUUUUCCUUCACAGAAUGU | 446 |
| S403-AS446-M3 | AUUCUGUGAAGGAAAAGUUUGCAGCCGAAAGGCUGC | 403 | AAACUUUUCCUUCACAGAAUGU | 446 |
| S403-AS446-M4 | AUUCUGUGAAGGAAAAGUUUGCAGCCGAAAGGCUGC | 403 | AAACUUUUCCUUCACAGAAUGU | 446 |
| S403-AS446-M5 | AUUCUGUGAAGGAAAAGUUUGCAGCCGAAAGGCUGC | 403 | AAACUUUUCCUUCACAGAAUGU | 446 |
| S403-AS446-M6 | AUUCUGUGAAGGAAAAGUUUGCAGCCGAAAGGCUGC | 403 | AAACUUUUCCUUCACAGAAUGU | 446 |
| S403-AS446-M7 | AUUCUGUGAAGGAAAAGUUUGCAGCCGAAAGGCUGC | 403 | AAACUUUUCCUUCACAGAAUGU | 446 |
| S403-AS446-M8 | AUUCUGUGAAGGAAAAGUUUGCAGCCGAAAGGCUGC | 403 | AAACUUUUCCUUCACAGAAUGU | 446 |
| S403-AS446-M9 | AUUCUGUGAAGGAAAAGUUUGCAGCCGAAAGGCUGC | 403 | AAACUUUUCCUUCACAGAAUGU | 446 |
| S403-AS446-M10 | AUUCUGUGAAGGAAAAGUUUGCAGCCGAAAGGCUGC | 403 | AAACUUUUCCUUCACAGAAUGU | 446 |
| S403-AS446-M11 | AUUCUGUGAAGGAAAAGUUUGCAGCCGAAAGGCUGC | 403 | AAACUUUUCCUUCACAGAAUGU | 446 |
| S404-AS447-M12 | AUUCUGUGAAGGAAAAGUUGCAGCCGAAAGGCUGC | 404 | AACUUUUCCUUCACAGAAUGU | 447 |
| S404-AS447-M13 | AUUCUGUGAAGGAAAAGUUGCAGCCGAAAGGCUGC | 404 | AACUUUUCCUUCACAGAAUGU | 447 |
| S405-AS448-M2 | CUUGGAGUAUUUCCAUCAUAGCAGCCGAAAGGCUGC | 405 | UAUGAUGGAAAUACUCCAAGAU | 448 |
| S405-AS448-M3 | CUUGGAGUAUUUCCAUCAUAGCAGCCGAAAGGCUGC | 405 | UAUGAUGGAAAUACUCCAAGAU | 448 |
| S405-AS448-M4 | CUUGGAGUAUUUCCAUCAUAGCAGCCGAAAGGCUGC | 405 | UAUGAUGGAAAUACUCCAAGAU | 448 |
| S405-AS448-M5 | CUUGGAGUAUUUCCAUCAUAGCAGCCGAAAGGCUGC | 405 | UAUGAUGGAAAUACUCCAAGAU | 448 |
| S405-AS448-M6 | CUUGGAGUAUUUCCAUCAUAGCAGCCGAAAGGCUGC | 405 | UAUGAUGGAAAUACUCCAAGAU | 448 |
| S405-AS448-M7 | CUUGGAGUAUUUCCAUCAUAGCAGCCGAAAGGCUGC | 405 | UAUGAUGGAAAUACUCCAAGAU | 448 |
| S405-AS448-M8 | CUUGGAGUAUUUCCAUCAUAGCAGCCGAAAGGCUGC | 405 | UAUGAUGGAAAUACUCCAAGAU | 448 |
| S405-AS448-M9 | CUUGGAGUAUUUCCAUCAUAGCAGCCGAAAGGCUGC | 405 | UAUGAUGGAAAUACUCCAAGAU | 448 |
| S405-AS448-M10 | CUUGGAGUAUUUCCAUCAUAGCAGCCGAAAGGCUGC | 405 | UAUGAUGGAAAUACUCCAAGAU | 448 |
| S405-AS448-M11 | CUUGGAGUAUUUCCAUCAUAGCAGCCGAAAGGCUGC | 405 | UAUGAUGGAAAUACUCCAAGAU | 448 |
| S406-AS449-M12 | CUUGGAGUAUUUCCAUCAUGCAGCCGAAAGGCUGC | 406 | ATGAUGGAAAUACUCCAAGAU | 449 |
| S406-AS450-M13 | CUUGGAGUAUUUCCAUCAUGCAGCCGAAAGGCUGC | 406 | AUGAUGGAAAUACUCCAAGAU | 450 |
| S407-AS451-M2 | UGGAGUAUUUCCAUCAUACUGCAGCCGAAAGGCUGC | 407 | AGUAUGAUGGAAAUACUCCAAG | 451 |

TABLE 4-continued

GYS2 RNAi oligonucleotides

| App Name | Sense Sequence | S SEQ ID NO | Antisense Sequence | AS SEQ ID NO |
|---|---|---|---|---|
| S407-AS451-M3 | UGGAGUAUUUCCAUCAUACUGCAGCCGAAAGGCUGC | 407 | AGUAUGAUGGAAAUACUCCAAG | 451 |
| S407-AS451-M4 | UGGAGUAUUUCCAUCAUACUGCAGCCGAAAGGCUGC | 407 | AGUAUGAUGGAAAUACUCCAAG | 451 |
| S407-AS451-M5 | UGGAGUAUUUCCAUCAUACUGCAGCCGAAAGGCUGC | 407 | AGUAUGAUGGAAAUACUCCAAG | 451 |
| S407-AS452-M6 | UGGAGUAUUUCCAUCAUACUGCAGCCGAAAGGCUGC | 407 | AGUAUGAUGGAAAUACTCCAAG | 452 |
| S407-AS451-M7 | UGGAGUAUUUCCAUCAUACUGCAGCCGAAAGGCUGC | 407 | AGUAUGAUGGAAAUACUCCAAG | 451 |
| S407-AS451-M8 | UGGAGUAUUUCCAUCAUACUGCAGCCGAAAGGCUGC | 407 | AGUAUGAUGGAAAUACUCCAAG | 451 |
| S407-AS451-M9 | UGGAGUAUUUCCAUCAUACUGCAGCCGAAAGGCUGC | 407 | AGUAUGAUGGAAAUACUCCAAG | 451 |
| S407-AS451-M10 | UGGAGUAUUUCCAUCAUACUGCAGCCGAAAGGCUGC | 407 | AGUAUGAUGGAAAUACUCCAAG | 451 |
| S407-AS451-M11 | UGGAGUAUUUCCAUCAUACUGCAGCCGAAAGGCUGC | 407 | AGUAUGAUGGAAAUACUCCAAG | 451 |
| S408-AS453-M12 | UGGAGUAUUUCCAUCAUACGCAGCCGAAAGGCUGC | 408 | GTAUGAUGGAAAUACTCCAAG | 453 |
| S408-AS454-M13 | UGGAGUAUUUCCAUCAUACGCAGCCGAAAGGCUGC | 408 | GUAUGAUGGAAAUACUCCAAG | 454 |
| S409-AS455-M2 | GAGUAUUUCCAUCAUACUAUGCAGCCGAAAGGCUGC | 409 | AUAGUAUGAUGGAAAUACUCCA | 455 |
| S409-AS455-M3 | GAGUAUUUCCAUCAUACUAUGCAGCCGAAAGGCUGC | 409 | AUAGUAUGAUGGAAAUACUCCA | 455 |
| S409-AS455-M4 | GAGUAUUUCCAUCAUACUAUGCAGCCGAAAGGCUGC | 409 | AUAGUAUGAUGGAAAUACUCCA | 455 |
| S409-AS455-M5 | GAGUAUUUCCAUCAUACUAUGCAGCCGAAAGGCUGC | 409 | AUAGUAUGAUGGAAAUACUCCA | 455 |
| S409-AS456-M6 | GAGUAUUUCCAUCAUACUAUGCAGCCGAAAGGCUGC | 409 | ATAGUAUGAUGGAAAUACTCCA | 456 |
| S409-AS455-M7 | GAGUAUUUCCAUCAUACUAUGCAGCCGAAAGGCUGC | 409 | AUAGUAUGAUGGAAAUACUCCA | 455 |
| S409-AS455-M8 | GAGUAUUUCCAUCAUACUAUGCAGCCGAAAGGCUGC | 409 | AUAGUAUGAUGGAAAUACUCCA | 455 |
| S409-AS455-M9 | GAGUAUUUCCAUCAUACUAUGCAGCCGAAAGGCUGC | 409 | AUAGUAUGAUGGAAAUACUCCA | 455 |
| S409-AS455-M10 | GAGUAUUUCCAUCAUACUAUGCAGCCGAAAGGCUGC | 409 | AUAGUAUGAUGGAAAUACUCCA | 455 |
| S409-AS455-M11 | GAGUAUUUCCAUCAUACUAUGCAGCCGAAAGGCUGC | 409 | AUAGUAUGAUGGAAAUACUCCA | 455 |
| S410-AS457-M12 | GAGUAUUUCCAUCAUACUAGCAGCCGAAAGGCUGC | 410 | UAGUAUGAUGGAAAUACTCCA | 457 |
| S410-AS458-M13 | GAGUAUUUCCAUCAUACUAGCAGCCGAAAGGCUGC | 410 | UAGUAUGAUGGAAAUACUCCA | 458 |
| S411-AS459-M2 | CCAGCAUGCCAGACACCUGAGCAGCCGAAAGGCUGC | 411 | UCAGGUGUCUGGCAUGCUGGUA | 459 |
| S411-AS459-M3 | CCAGCAUGCCAGACACCUGAGCAGCCGAAAGGCUGC | 411 | UCAGGUGUCUGGCAUGCUGGUA | 459 |

TABLE 4-continued

GYS2 RNAi oligonucleotides

| App Name | Sense Sequence | S SEQ ID NO | Antisense Sequence | AS SEQ ID NO |
|---|---|---|---|---|
| S411-AS459-M4 | CCAGCAUGCCAGACACCUGAGCAGCCGAAAGGCUGC | 411 | UCAGGUGUCUGGCAUGCUGGUA | 459 |
| S411-AS459-M5 | CCAGCAUGCCAGACACCUGAGCAGCCGAAAGGCUGC | 411 | UCAGGUGUCUGGCAUGCUGGUA | 459 |
| S411-AS459-M6 | CCAGCAUGCCAGACACCUGAGCAGCCGAAAGGCUGC | 411 | UCAGGUGUCUGGCAUGCUGGUA | 459 |
| S411-AS459-M7 | CCAGCAUGCCAGACACCUGAGCAGCCGAAAGGCUGC | 411 | UCAGGUGUCUGGCAUGCUGGUA | 459 |
| S411-AS459-M8 | CCAGCAUGCCAGACACCUGAGCAGCCGAAAGGCUGC | 411 | UCAGGUGUCUGGCAUGCUGGUA | 459 |
| S411-AS459-M9 | CCAGCAUGCCAGACACCUGAGCAGCCGAAAGGCUGC | 411 | UCAGGUGUCUGGCAUGCUGGUA | 459 |
| S411-AS459-M10 | CCAGCAUGCCAGACACCUGAGCAGCCGAAAGGCUGC | 411 | UCAGGUGUCUGGCAUGCUGGUA | 459 |
| S411-AS459-M11 | CCAGCAUGCCAGACACCUGAGCAGCCGAAAGGCUGC | 411 | UCAGGUGUCUGGCAUGCUGGUA | 459 |
| S412-AS460-M12 | CCAGCAUGCCAGACACCUGGCAGCCGAAAGGCUGC | 412 | CAGGUGUCUGGCAUGCUGGUA | 460 |
| S412-AS460-M13 | CCAGCAUGCCAGACACCUGGCAGCCGAAAGGCUGC | 412 | CAGGUGUCUGGCAUGCUGGUA | 460 |
| S413-AS461-M2 | AGAAAAAGCUGCAUGGUGAAGCAGCCGAAAGGCUGC | 413 | UUCACCAUGCAGCUUUUUCUUC | 461 |
| S413-AS461-M3 | AGAAAAAGCUGCAUGGUGAAGCAGCCGAAAGGCUGC | 413 | UUCACCAUGCAGCUUUUUCUUC | 461 |
| S413-AS461-M4 | AGAAAAAGCUGCAUGGUGAAGCAGCCGAAAGGCUGC | 413 | UUCACCAUGCAGCUUUUUCUUC | 461 |
| S413-AS461-M5 | AGAAAAAGCUGCAUGGUGAAGCAGCCGAAAGGCUGC | 413 | UUCACCAUGCAGCUUUUUCUUC | 461 |
| S413-AS462-M6 | AGAAAAAGCUGCAUGGUGAAGCAGCCGAAAGGCUGC | 413 | UTCACCAUGCAGCUUUUCUUUC | 462 |
| S413-AS461-M7 | AGAAAAAGCUGCAUGGUGAAGCAGCCGAAAGGCUGC | 413 | UUCACCAUGCAGCUUUUUCUUC | 461 |
| S413-AS461-M8 | AGAAAAAGCUGCAUGGUGAAGCAGCCGAAAGGCUGC | 413 | UUCACCAUGCAGCUUUUUCUUC | 461 |
| S413-AS461-M9 | AGAAAAAGCUGCAUGGUGAAGCAGCCGAAAGGCUGC | 413 | UUCACCAUGCAGCUUUUUCUUC | 461 |
| S413-AS461-M10 | AGAAAAAGCUGCAUGGUGAAGCAGCCGAAAGGCUGC | 413 | UUCACCAUGCAGCUUUUUCUUC | 461 |
| S413-AS461-M11 | AGAAAAAGCUGCAUGGUGAAGCAGCCGAAAGGCUGC | 413 | UUCACCAUGCAGCUUUUUCUUC | 461 |
| S414-AS463-M12 | AGAAAAAGCUGCAUGGUGAGCAGCCGAAAGGCUGC | 414 | UCACCAUGCAGCUUUUUCUUC | 463 |
| S414-AS464-M13 | AGAAAAAGCUGCAUGGUGAGCAGCCGAAAGGCUGC | 414 | UCACCAUGCAGCUUUUUCUUC | 464 |
| S415-AS465-M2 | UGGUGAAUAUAAGAACUGAAGCAGCCGAAAGGCUGC | 415 | UUCAGUUCUUAUAUUCACCAUG | 465 |
| S415-AS465-M3 | UGGUGAAUAUAAGAACUGAAGCAGCCGAAAGGCUGC | 415 | UUCAGUUCUUAUAUUCACCAUG | 465 |
| S415-AS465-M4 | UGGUGAAUAUAAGAACUGAAGCAGCCGAAAGGCUGC | 415 | UUCAGUUCUUAUAUUCACCAUG | 465 |

TABLE 4-continued

GYS2 RNAi oligonucleotides

| App Name | Sense Sequence | S SEQ ID NO | Antisense Sequence | AS SEQ ID NO |
|---|---|---|---|---|
| S415-AS465-M5 | UGGUGAAUAUAAGAACUGAAGCAGCCGAAAGGCUGC | 415 | UUCAGUUCUUAUAUUCACCAUG | 465 |
| S415-AS598-M6 | UGGUGAAUAUAAGAACUGAAGCAGCCGAAAGGCUGC | 415 | UTCAGUUCUUAUAUUCACCAUG | 598 |
| S415-AS465-M7 | UGGUGAAUAUAAGAACUGAAGCAGCCGAAAGGCUGC | 415 | UUCAGUUCUUAUAUUCACCAUG | 465 |
| S415-AS465-M8 | UGGUGAAUAUAAGAACUGAAGCAGCCGAAAGGCUGC | 415 | UUCAGUUCUUAUAUUCACCAUG | 465 |
| S415-AS465-M9 | UGGUGAAUAUAAGAACUGAAGCAGCCGAAAGGCUGC | 415 | UUCAGUUCUUAUAUUCACCAUG | 465 |
| S415-AS465-M10 | UGGUGAAUAUAAGAACUGAAGCAGCCGAAAGGCUGC | 415 | UUCAGUUCUUAUAUUCACCAUG | 465 |
| S415-AS465-M11 | UGGUGAAUAUAAGAACUGAAGCAGCCGAAAGGCUGC | 415 | UUCAGUUCUUAUAUUCACCAUG | 465 |
| S416-AS466-M12 | UGGUGAAUAUAAGAACUGAGCAGCCGAAAGGCUGC | 416 | UCAGUUCUUAUAUUCACCAUG | 466 |
| S416-AS466-M13 | UGGUGAAUAUAAGAACUGAGCAGCCGAAAGGCUGC | 416 | UCAGUUCUUAUAUUCACCAUG | 466 |
| S467-AS518-M1 | GGAGGCAUCUAUACUGUGAUUCAGA | 467 | UCUGAAUCACAGUAUAGAUGCCUCCAA | 518 |
| S468-AS519-M1 | GGCAUCUAUACUGUGAUUCAGACAA | 468 | UUGUCUGAAUCACAGUAUAGAUGCCUC | 519 |
| S469-AS520-M1 | GCAUCUAUACUGUGAUUCAGACAAA | 469 | UUUGUCUGAAUCACAGUAUAGAUGCCU | 520 |
| S470-AS521-M1 | GUCCAUAUUUUGAGCAUAAUAUGAA | 470 | UUCAUAUUAUGCUCAAAAUAUGGACCU | 521 |
| S471-AS522-M1 | AUAUUUUGAGCAUAAUAUGAAGACT | 471 | AGUCUUCAUAUUAUGCUCAAAAUAUGG | 522 |
| S52-AS244-M1 | GCAGCAAAUAUUGAUUUCUACAACC | 52 | GGUUGUAGAAAUCAAUAUUUGCUGCAC | 244 |
| S55-AS247-M1 | GCAAAUAUUGAUUUCUACAACCATC | 55 | GAUGGUUGUAGAAAUCAAUAUUUGCUG | 247 |
| S75-AS267-M1 | GGUUUCUGAAAUAACAGCAAUAGAA | 75 | UUCUAUUGCUGUUAUUUCAGAAACCGU | 267 |
| S77-AS269-M1 | CUGAAAUAACAGCAAUAGAAGCUGA | 77 | UCAGCUUCUAUUGCUGUUAUUUCAGAA | 269 |
| S472-AS523-M1 | ACGGCUUGAAUGUUAAGAAAUUUUC | 472 | GAAAAUUUCUUAACAUUCAAGCCGUUU | 523 |
| S473-AS524-M1 | CGGCUUGAAUGUUAAGAAAUUUUCA | 473 | UGAAAAUUUCUUAACAUUCAAGCCGUU | 524 |
| S80-AS272-M1 | GGCUUGAAUGUUAAGAAAUUUUCAG | 80 | CUGAAAAUUUCUUAACAUUCAAGCCGU | 272 |
| S81-AS273-M1 | GCUUGAAUGUUAAGAAAUUUUCAGC | 81 | GCUGAAAAUUUCUUAACAUUCAAGCCG | 273 |
| S82-AS274-M1 | CUUGAAUGUUAAGAAAUUUUCAGCA | 82 | UGCUGAAAAUUUCUUAACAUUCAAGCC | 274 |
| S83-AS275-M1 | UUGAAUGUUAAGAAAUUUUCAGCAG | 83 | CUGCUGAAAAUUUCUUAACAUUCAAGC | 275 |
| S84-AS276-M1 | UGAAUGUUAAGAAAUUUUCAGCAGT | 84 | ACUGCUGAAAAUUUCUUAACAUUCAAG | 276 |

TABLE 4-continued

GYS2 RNAi oligonucleotides

| App Name | Sense Sequence | S SEQ ID NO | Antisense Sequence | AS SEQ ID NO |
|---|---|---|---|---|
| S85-AS277-M1 | GAAUGUUAAGAAAUUUUCAGCAGTG | 85 | CACUGCUGAAAAUUUCUUAACAUUCAA | 277 |
| S474-AS525-M1 | AAUGUUAAGAAAUUUUCAGCAGUGC | 474 | GCACUGCUGAAAAUUUCUUAACAUUCA | 525 |
| S86-AS278-M1 | AUGUUAAGAAAUUUUCAGCAGUGCA | 86 | UGCACUGCUGAAAAUUUCUUAACAUUC | 278 |
| S475-AS526-M1 | UGUUAAGAAAUUUUCAGCAGUGCAT | 475 | AUGCACUGCUGAAAAUUUCUUAACAUU | 526 |
| S476-AS527-M1 | GUUAAGAAAUUUUCAGCAGUGCATG | 476 | CAUGCACUGCUGAAAAUUUCUUAACAU | 527 |
| S143-AS335-M1 | GGAGUAUUUCCAUCAUACUAUGAAC | 143 | GUUCAUAGUAUGAUGGAAAUACUCCAA | 335 |
| S181-AS373-M1 | GCUGCAUGGUGAAUAUAAGAACUGA | 181 | UCAGUUCUUAUAUUCACCAUGCAGCUU | 373 |
| S182-AS374-M1 | CUGCAUGGUGAAUAUAAGAACUGAA | 182 | UUCAGUUCUUAUAUUCACCAUGCAGCU | 374 |
| S477-AS528-M1 | UGCAUGGUGAAUAUAAGAACUGAAT | 477 | AUUCAGUUCUUAUAUUCACCAUGCAGC | 528 |
| S183-AS375-M1 | GCAUGGUGAAUAUAAGAACUGAATT | 183 | AAUUCAGUUCUUAUAUUCACCAUGCAG | 375 |
| S184-AS376-M1 | CAUGGUGAAUAUAAGAACUGAAUTC | 184 | GAAUUCAGUUCUUAUAUUCACCAUGCA | 376 |
| S185-AS377-M1 | AUGGUGAAUAUAAGAACUGAAUUCT | 185 | AGAAUUCAGUUCUUAUAUUCACCAUGC | 377 |
| S186-AS378-M1 | UGGUGAAUAUAAGAACUGAAUUCTA | 186 | UAGAAUUCAGUUCUUAUAUUCACCAUG | 378 |
| S187-AS379-M1 | GGUGAAUAUAAGAACUGAAUUCTAC | 187 | GUAGAAUUCAGUUCUUAUAUUCACCAU | 379 |
| S188-AS380-M1 | GUGAAUAUAAGAACUGAAUUCTACA | 188 | UGUAGAAUUCAGUUCUUAUAUUCACCA | 380 |
| S478-AS529-M1 | UGAAUAUAAGAACUGAAUUCUACAT | 478 | AUGUAGAAUUCAGUUCUUAUAUUCACC | 529 |
| S479-AS530-M1 | GAAUAUAAGAACUGAAUUCUACATG | 479 | CAUGUAGAAUUCAGUUCUUAUAUUCAC | 530 |
| S189-AS381-M1 | AAUAUAAGAACUGAAUUCUACAUGT | 189 | ACAUGUAGAAUUCAGUUCUUAUAUUCA | 381 |
| S480-AS531-M1 | CAAAGUAAGACUAAUUAUUUAAAAT | 480 | AUUUUAAAUAAUUAGUCUUACUUUGCU | 531 |
| S481-AS532-M1 | AAAGUAAGACUAAUUAUUUAAAATA | 481 | UAUUUUAAAUAAUUAGUCUUACUUUGC | 532 |
| S482-AS533-M1 | AGAAAUUGAGUGAAUGACAAUUUTG | 482 | CAAAAUUGUCAUUCACUCAAUUUCUUC | 533 |
| S483-AS534-M1 | AAAUUGAGUGAAUGACAAUUUUGTA | 483 | UACAAAAUUGUCAUUCACUCAAUUUCU | 534 |
| S484-AS535-M1 | AUUGAGUGAAUGACAAUUUUGUAAT | 484 | AUUACAAAAUUGUCAUUCACUCAAUUU | 535 |
| S485-AS536-M1 | AAUGACAAUUUUGUAAUUUAGGATA | 485 | UAUCCUAAAUUACAAAAUUGUCAUUCA | 536 |
| S486-AS537-M1 | AAGUGUUUUAAAAUGGUGAAUUTA | 486 | UAAAUUCACCAUUUUAAAAACACUUUU | 537 |

TABLE 4-continued

GYS2 RNAi oligonucleotides

| App Name | Sense Sequence | S SEQ ID NO | Antisense Sequence | AS SEQ ID NO |
|---|---|---|---|---|
| S487-AS538-M1 | AGUGUUUUAAAAUGGUGAAUUUAA | 487 | UUAAAUUCACCAUUUUAA AAACACUUU | 538 |
| S488-AS539-M1 | CUUACUCUGUUUAUUUUUAAAUGAT | 488 | AUCAUUUAAAAAUAAACAG AGUAAGAG | 539 |
| S489-AS540-M1 | CUCUGUUUAUUUUUAAAUGAUCATC | 489 | GAUGAUCAUUUAAAAAUA AACAGAGUA | 540 |
| S490-AS541-M1 | UCUGUUUAUUUUUAAAUGAUCAUCA | 490 | UGAUGAUCAUUUAAAAAU AAACAGAGU | 541 |
| S491-AS542-M1 | GUUUAUUUUAAAUGAUCAUCAUAA | 491 | UUAUGAUGAUCAUUUAAA AAUAAACAG | 542 |
| S492-AS543-M1 | AUCAUCAUAAUCCUUUGCUUACUAT | 492 | AUAGUAAGCAAAGGAUUA UGAUGAUCA | 543 |
| S493-AS544-M1 | GUGCACUACCUACAUUUUUAAATA | 493 | UAUUUAAAAAUGUAGGU AGUGCACAU | 544 |
| S494-AS545-M1 | GCUAGGUUUUACUGAUUAUUUUCA | 494 | UGAAAAUAAUCAGUAAAAA CCUAGCUA | 545 |
| S495-AS546-M1 | CUAGGUUUUACUGAUUAUUUUCAT | 495 | AUGAAAAUAAUCAGUAAAA ACCUAGCU | 546 |
| S496-AS547-M1 | AGGUUUUACUGAUUAUUUUCAUTT | 496 | AAAUGAAAAUAAUCAGUAA AAACCUAG | 547 |
| S497-AS548-M1 | CUGAUUAUUUUCAUUUUUCACAUGC | 497 | GCAUGUGAAAAAUGAAAA UAAUCAGUA | 548 |
| S498-AS549-M1 | AUGGACAUUUAUGUCACUUUUGAAA | 498 | UUUCAAAAGUGACAUAAA UGUCCAUUA | 549 |
| S499-AS550-M1 | GACAUUUAUGUCACUUUUGAAAUCT | 499 | AGAUUUCAAAAGUGACAU AAAUGUCCA | 550 |
| S500-AS551-M1 | ACAUUUAUGUCACUUUUGAAAUCTA | 500 | UAGAUUUCAAAAGUGACA UAAAUGUCC | 551 |
| S501-AS552-M1 | UAGAAUUGAUGUUGUAAUUAAUGCA | 501 | UGCAUUAAUUACAACAUCA AUUCUAGA | 552 |
| S502-AS553-M1 | AGAAUUGAUGUUGUAAUUAAUGCAA | 502 | UUGCAUUAAUUACAACAUC AAUUCUAG | 553 |
| S503-AS554-M1 | GAAUUGAUGUUGUAAUUAAUGCAAG | 503 | CUUGCAUUAAUUACAACAU CAAUUCUA | 554 |
| S504-AS555-M1 | ACCAUCUUACUGUAACAUUUUUCTA | 504 | UAGAAAAAUGUUACAGUA AGAUGGUGG | 555 |
| S505-AS556-M1 | CAUCUUACUGUAACAUUUUUCUATT | 505 | AAUAGAAAAAUGUUACAG UAAGAUGGU | 556 |
| S506-AS557-M1 | UCUUACUGUAACAUUUUUCUAUUGT | 506 | ACAAUAGAAAAAUGUUACA GUAAGAUG | 557 |
| S507-AS558-M1 | CUUACUGUAACAUUUUUCUAUUGTT | 507 | AACAAUAGAAAAAUGUUAC AGUAAGAU | 558 |
| S508-AS559-M1 | UUACUGUAACAUUUUUCUAUUGUTT | 508 | AAACAAUAGAAAAAUGUUA CAGUAAGA | 559 |
| S509-AS560-M1 | ACUGUAACAUUUUUCUAUUGUUUAA | 509 | UUAAACAAUAGAAAAAUG UUACAGUAA | 560 |
| S510-AS561-M1 | CUGUAACAUUUUUCUAUUGUUUAAA | 510 | UUUAAACAAUAGAAAAAU GUUACAGUA | 561 |
| S511-AS562-M1 | UGUAACAUUUUUCUAUUGUUUAAAT | 511 | AUUUAAACAAUAGAAAAA UGUUACAGU | 562 |

TABLE 4-continued

GYS2 RNAi oligonucleotides

| App Name | Sense Sequence | S SEQ ID NO | Antisense Sequence | AS SEQ ID NO |
|---|---|---|---|---|
| S512-AS563-M1 | GUAACAUUUUCUAUUGUUUAAATA | 512 | UAUUUAAACAAUAGAAAAAUGUUACAG | 563 |
| S513-AS564-M1 | UAACAUUUUCUAUUGUUUAAAUAG | 513 | CUAUUUAAACAAUAGAAAAAUGUUACA | 564 |
| S514-AS565-M1 | AACAUUUUCUAUUGUUUAAAUAGA | 514 | UCUAUUUAAACAAUAGAAAAAUGUUAC | 565 |
| S515-AS566-M1 | ACAUUUUCUAUUGUUUAAAUAGAA | 515 | UUCUAUUUAAACAAUAGAAAAUGUUA | 566 |
| S516-AS567-M1 | CAUUUUCUAUUGUUUAAAUAGAAA | 516 | UUUCUAUUUAAACAAUAGAAAAAUGUU | 567 |
| S517-AS568-M1 | GUCAAUCUUCAUAGAUGAUAACUTG | 517 | CAAGUUAUCAUCUAUGAAGAUUGACCA | 568 |
| S569-AS575-M14 | GGCAUCUAUACUGUGAUUCAGCAGCCGAAAGGCUGC | 569 | UGAAUCACAGUAUAGAUGCCGG | 575 |
| S569-AS575-M15 | GGCAUCUAUACUGUGAUUCAGCAGCCGAAAGGCUGC | 569 | UGAAUCACAGUAUAGAUGCCGG | 575 |
| S570-AS576-M14 | GCAUCUAUACUGUGAUUCAGGCAGCCGAAAGGCUGC | 570 | CUGAAUCACAGUAUAGAUGCGG | 576 |
| S570-AS576-M15 | GCAUCUAUACUGUGAUUCAGGCAGCCGAAAGGCUGC | 570 | CUGAAUCACAGUAUAGAUGCGG | 576 |
| S571-AS577-M14 | GCAGCAAAUAUUGAUUUCUAGCAGCCGAAAGGCUGC | 571 | UAGAAAUCAAUAUUUGCUGCGG | 577 |
| S571-AS577-M15 | GCAGCAAAUAUUGAUUUCUAGCAGCCGAAAGGCUGC | 571 | UAGAAAUCAAUAUUUGCUGCGG | 577 |
| S572-AS578-M15 | CUGAAAUAACAGCAAUAGAAGCAGCCGAAAGGCUGC | 572 | UUCUAUUGCUGUUAUUUCAGGG | 578 |
| S573-AS579-M15 | ACGGCUUGAAUGUUAAGAAAGCAGCCGAAAGGCUGC | 573 | UUUCUUAACAUUCAAGCCGUGG | 579 |
| S574-AS580-M14 | AGUGUUUUUAAAAUGGUGAAGCAGCCGAAAGGCUGC | 574 | UUCACCAUUUUAAAAACACUGG | 580 |
| S574-AS580-M15 | AGUGUUUUUAAAAUGGUGAAGCAGCCGAAAGGCUGC | 574 | UUCACCAUUUUAAAAACACUGG | 580 |
| S385-AS417-M16 | AGGUGCAUUUUGGAAGAUGGGCAGCCGAAAGGCUGC | 385 | CCAUCUUCCAAAAUGCACCUGG | 417 |
| S389-AS421-M17 | AAGGAAGUCCUUAUGUGGUAGCAGCCGAAAGGCUGC | 389 | UACCACAUAAGGACUUCCUUCU | 421 |
| S391-AS425-M16 | AUGAUAUGCUGAUAUUUGGAGCAGCCGAAAGGCUGC | 391 | UCCAAAUAUCAGCAUAUCAUUG | 425 |
| S393-AS429-M16 | AGCAAAUAUUGAUUUCUACAGCAGCCGAAAGGCUGC | 393 | UGUAGAAAUCAAUAUUUGCUGC | 429 |
| S397-AS436-M16 | CUUGAAUGUUAAGAAAUUUGCAGCCGAAAGGCUGC | 397 | AAAAUUUCUUAACAUUCAAGCC | 436 |
| S397-AS586-M18 | CUUGAAUGUUAAGAAAUUUGCAGCCGAAAGGCUGC | 397 | UAAAUUUCUUAACAUUCAAGGG | 586 |
| S397-AS587-M19 | CUUGAAUGUUAAGAAAUUUGCAGCCGAAAGGCUGC | 397 | AAAAUUUCUUAACAUUCAAGGG | 587 |
| S395-AS433-M17 | CCACGGUUUCUGAAAUAACAGCAGCCGAAAGGCUGC | 395 | UGUUAUUUCAGAAACCGUGGUG | 433 |
| S399-AS438-M16 | UGAAUGUUAAGAAAUUUUCAGCAGCCGAAAGGCUGC | 399 | UGAAAAUUUCUUAACAUUCAAG | 438 |

TABLE 4-continued

GYS2 RNAi oligonucleotides

| App Name | Sense Sequence | S SEQ ID NO | Antisense Sequence | AS SEQ ID NO |
|---|---|---|---|---|
| S401-AS442-M17 | CGAGGUCAUUUCUAUGGUCAGCAGCCGAAAGGCUGC | 401 | UGACCAUAGAAAUGACCUCGAA | 442 |
| S405-AS448-M17 | CUUGGAGUAUUUCCAUCAUAGCAGCCGAAAGGCUGC | 405 | UAUGAUGGAAAUACUCCAAGAU | 448 |
| S413-AS461-M17 | AGAAAAAGCUGCAUGGUGAAGCAGCCGAAAGGCUGC | 413 | UUCACCAUGCAGCUUUUUCUUC | 461 |
| S413-AS588-M20 | AGAAAAAGCUGCAUGGUGAAGCAGCCGAAAGGCUGC | 413 | UUCACCAUGCAGCUUUUUCUGG | 588 |
| S413-AS589-M21 | AGAAAAAGCUGCAUGGUGAAGCAGCCGAAAGGCUGC | 413 | UCACCAUGCAGCUUUUUCUGG | 589 |
| S413-AS461-M22 | AGAAAAAGCUGCAUGGUGAAGCAGCCGAAAGGCUGC | 413 | UUCACCAUGCAGCUUUUUCUUC | 461 |
| S415-AS465-M16 | UGGUGAAUAUAAGAACUGAAGCAGCCGAAAGGCUGC | 415 | UUCAGUUCUUAUAUUCACCAUG | 465 |
| S393-AS589-M18 | AGCAAAUAUUGAUUUCUACAGCAGCCGAAAGGCUGC | 393 | UGUAGAAAUCAAUAUUGCUGG | 589 |
| S397-AS586-M23 | CUUGAAUGUUAAGAAAUUUAGCAGCCGAAAGGCUGC | 397 | UAAAUUUCUUAACAUUCAAGGG | 586 |
| S399-AS590-M18 | UGAAUGUUAAGAAAUUUUCAGCAGCCGAAAGGCUGC | 399 | UGAAAAUUUCUUAACAUUCAGG | 590 |
| S413-AS588-M20 | AGAAAAAGCUGCAUGGUGAAGCAGCCGAAAGGCUGC | 413 | UUCACCAUGCAGCUUUUUCUGG | 588 |
| S415-AS591-M18 | UGGUGAAUAUAAGAACUGAAGCAGCCGAAAGGCUGC | 415 | UUCAGUUCUUAUAUUCACCAGG | 591 |
| S415-AS591-M23 | UGGUGAAUAUAAGAACUGAAGCAGCCGAAAGGCUGC | 415 | UUCAGUUCUUAUAUUCACCAGG | 591 |
| S397-AS592-M24 | CUUGAAUGUUAAGAAAUUUGCAGCCGAAAGGCUGC | 397 | AAAAUUUCUUAACAUUCAAGGG | 592 |
| S397-AS592-M25 | CUUGAAUGUUAAGAAAUUUGCAGCCGAAAGGCUGC | 397 | AAAAUUUCUUAACAUUCAAGGG | 592 |
| S397-AS592-M26 | CUUGAAUGUUAAGAAAUUUGCAGCCGAAAGGCUGC | 397 | AAAAUUUCUUAACAUUCAAGGG | 592 |
| S397-AS592-M27 | CUUGAAUGUUAAGAAAUUUGCAGCCGAAAGGCUGC | 397 | AAAAUUUCUUAACAUUCAAGGG | 592 |
| S399-AS590-M24 | UGAAUGUUAAGAAAUUUUCAGCAGCCGAAAGGCUGC | 399 | UGAAAAUUUCUUAACAUUCAGG | 590 |
| S399-AS590-M25 | UGAAUGUUAAGAAAUUUUCAGCAGCCGAAAGGCUGC | 399 | UGAAAAUUUCUUAACAUUCAGG | 590 |
| S399-AS590-M26 | UGAAUGUUAAGAAAUUUUCAGCAGCCGAAAGGCUGC | 399 | UGAAAAUUUCUUAACAUUCAGG | 590 |
| S399-AS590-M27 | UGAAUGUUAAGAAAUUUUCAGCAGCCGAAAGGCUGC | 399 | UGAAAAUUUCUUAACAUUCAGG | 590 |
| S415-AS591-M28 | UGGUGAAUAUAAGAACUGAAGCAGCCGAAAGGCUGC | 415 | UUCAGUUCUUAUAUUCACCAGG | 591 |
| S415-AS591-M29 | UGGUGAAUAUAAGAACUGAAGCAGCCGAAAGGCUGC | 415 | UUCAGUUCUUAUAUUCACCAGG | 591 |
| S415-AS591-M30 | UGGUGAAUAUAAGAACUGAAGCAGCCGAAAGGCUGC | 415 | UUCAGUUCUUAUAUUCACCAGG | 591 |
| S415-AS591-M31 | UGGUGAAUAUAAGAACUGAAGCAGCCGAAAGGCUGC | 415 | UUCAGUUCUUAUAUUCACCAGG | 591 |

TABLE 4-continued

GYS2 RNAi oligonucleotides

| App Name | Sense Sequence | S SEQ ID NO | Antisense Sequence | AS SEQ ID NO |
|---|---|---|---|---|
| S397-AS592-M32 | CUUGAAUGUUAAGAAAUUUUGCAGCCGAAAGGCUGC | 397 | AAAAUUUCUUAACAUUCAAGGG | 592 |
| S399-AS590-M32 | UGAAUGUUAAGAAAUUUUCAGCAGCCGAAAGGCUGC | 399 | UGAAAAUUUCUUAACAUUCAGG | 590 |
| S415-AS591-M33 | UGGUGAAUAUAAGAACUGAAGCAGCCGAAAGGCUGC | 415 | UUCAGUUCUUAUAUUCACCAGG | 591 |
| S399-AS590-M34 | UGAAUGUUAAGAAAUUUUCAGCAGCCGAAAGGCUGC | 399 | UGAAAAUUUCUUAACAUUCAGG | 590 |
| S399-AS590-M35 | UGAAUGUUAAGAAAUUUUCAGCAGCCGAAAGGCUGC | 399 | UGAAAAUUUCUUAACAUUCAGG | 590 |
| S399-AS590-M28 | UGAAUGUUAAGAAAUUUUCAGCAGCCGAAAGGCUGC | 399 | UGAAAAUUUCUUAACAUUCAGG | 590 |
| S399-AS590-M36 | UGAAUGUUAAGAAAUUUUCAGCAGCCGAAAGGCUGC | 399 | UGAAAAUUUCUUAACAUUCAGG | 590 |
| S581-AS593-M37 | GAAUGUUAAGAAAUUUUCAGCAGCCGAAAGGCUGC | 581 | UGAAAAUUUCUUAACAUUCGG | 593 |
| S399-AS590-M38 | UGAAUGUUAAGAAAUUUUCAGCAGCCGAAAGGCUGC | 399 | UGAAAAUUUCUUAACAUUCAGG | 590 |
| S399-AS590-M39 | UGAAUGUUAAGAAAUUUUCAGCAGCCGAAAGGCUGC | 399 | UGAAAAUUUCUUAACAUUCAGG | 590 |
| S399-AS590-M40 | UGAAUGUUAAGAAAUUUUCAGCAGCCGAAAGGCUGC | 399 | UGAAAAUUUCUUAACAUUCAGG | 590 |
| S399-AS590-M41 | UGAAUGUUAAGAAAUUUUCAGCAGCCGAAAGGCUGC | 399 | UGAAAAUUUCUUAACAUUCAGG | 590 |
| S399-AS590-M42 | UGAAUGUUAAGAAAUUUUCAGCAGCCGAAAGGCUGC | 399 | UGAAAAUUUCUUAACAUUCAGG | 590 |
| S399-AS590-M43 | UGAAUGUUAAGAAAUUUUCAGCAGCCGAAAGGCUGC | 399 | UGAAAAUUUCUUAACAUUCAGG | 590 |
| S399-AS590-M24 | UGAAUGUUAAGAAAUUUUCAGCAGCCGAAAGGCUGC | 399 | UGAAAAUUUCUUAACAUUCAGG | 590 |
| S399-AS590-M44 | UGAAUGUUAAGAAAUUUUCAGCAGCCGAAAGGCUGC | 399 | UGAAAAUUUCUUAACAUUCAGG | 590 |
| S399-AS590-M28 | UGAAUGUUAAGAAAUUUUCAGCAGCCGAAAGGCUGC | 399 | UGAAAAUUUCUUAACAUUCAGG | 590 |
| S399-AS590-M45 | UGAAUGUUAAGAAAUUUUCAGCAGCCGAAAGGCUGC | 399 | UGAAAAUUUCUUAACAUUCAGG | 590 |
| S399-AS590-M40 | UGAAUGUUAAGAAAUUUUCAGCAGCCGAAAGGCUGC | 399 | UGAAAAUUUCUUAACAUUCAGG | 590 |
| S399-AS590-M46 | UGAAUGUUAAGAAAUUUUCAGCAGCCGAAAGGCUGC | 399 | UGAAAAUUUCUUAACAUUCAGG | 590 |
| S399-AS590-M38 | UGAAUGUUAAGAAAUUUUCAGCAGCCGAAAGGCUGC | 399 | UGAAAAUUUCUUAACAUUCAGG | 590 |
| S399-AS590-M46 | UGAAUGUUAAGAAAUUUUCAGCAGCCGAAAGGCUGC | 399 | UGAAAAUUUCUUAACAUUCAGG | 590 |
| S571-AS577-M47 | GCAGCAAAUAUUGAUUUCUAGCAGCCGAAAGGCUGC | 571 | UAGAAAUCAAUAUUUGCUGCGG | 577 |
| S573-AS579-M47 | ACGGCUUGAAUGUUAAGAAAGCAGCCGAAAGGCUGC | 573 | UUUCUUAACAUUCAAGCCGUGG | 579 |
| S582-AS594-M47 | UGCAUGAGUUUCAAAAUCUAGCAGCCGAAAGGCUGC | 582 | UAGAUUUUGAAACUCAUGCAGG | 594 |

TABLE 4-continued

GYS2 RNAi oligonucleotides

| App Name | Sense Sequence | S SEQ ID NO | Antisense Sequence | AS SEQ ID NO |
|---|---|---|---|---|
| S583-AS595-M47 | UCGAGAUGAUCUAACAAUUAGCAGCCGAAAGGCUGC | 583 | UAAUUGUUAGAUCAUCUCGAGG | 595 |
| S584-AS596-M47 | AGACUAAUUAUUUAAAAUAAGCAGCCGAAAGGCUGC | 584 | UUAUUUUAAAUAAUUAGUCUGG | 596 |
| S574-AS580-M47 | AGUGUUUUUAAAAUGGUGAAGCAGCCGAAAGGCUGC | 574 | UUCACCAUUUUAAAAACACUGG | 580 |
| S585-AS597-M47 | AGAAUUGAUGUUGUAAUUAAGCAGCCGAAAGGCUGC | 585 | UUAAUUACAACAUCAAUUCUGG | 597 |
| S399-AS590-M48 | UGAAUGUUAAGAAAUUUUCAGCAGCCGAAAGGCUGC | 399 | UGAAAAUUUCUUAACAUUCAGG | 590 |
| S399-AS590-M49 | UGAAUGUUAAGAAAUUUUCAGCAGCCGAAAGGCUGC | 399 | UGAAAAUUUCUUAACAUUCAGG | 590 |
| S399-AS590-M50 | UGAAUGUUAAGAAAUUUUCAGCAGCCGAAAGGCUGC | 399 | UGAAAAUUUCUUAACAUUCAGG | 590 |
| S399-AS590-M51 | UGAAUGUUAAGAAAUUUUCAGCAGCCGAAAGGCUGC | 399 | UGAAAAUUUCUUAACAUUCAGG | 590 |
| S399-AS590-M52 | UGAAUGUUAAGAAAUUUUCAGCAGCCGAAAGGCUGC | 399 | UGAAAAUUUCUUAACAUUCAGG | 590 |
| S399-AS590-M53 | UGAAUGUUAAGAAAUUUUCAGCAGCCGAAAGGCUGC | 399 | UGAAAAUUUCUUAACAUUCAGG | 590 |
| S399-AS590-M54 | UGAAUGUUAAGAAAUUUUCAGCAGCCGAAAGGCUGC | 399 | UGAAAAUUUCUUAACAUUCAGG | 590 |
| S399-AS590-M55 | UGAAUGUUAAGAAAUUUUCAGCAGCCGAAAGGCUGC | 399 | UGAAAAUUUCUUAACAUUCAGG | 590 |
| S573-AS579-M56 | ACGGCUUGAAUGUUAAGAAAGCAGCCGAAAGGCUGC | 573 | UUUCUUAACAUUCAAGCCGUGG | 579 |
| S573-AS579-M57 | ACGGCUUGAAUGUUAAGAAAGCAGCCGAAAGGCUGC | 573 | UUUCUUAACAUUCAAGCCGUGG | 579 |
| S573-AS579-M50 | ACGGCUUGAAUGUUAAGAAAGCAGCCGAAAGGCUGC | 573 | UUUCUUAACAUUCAAGCCGUGG | 579 |
| S573-AS579-M51 | ACGGCUUGAAUGUUAAGAAAGCAGCCGAAAGGCUGC | 573 | UUUCUUAACAUUCAAGCCGUGG | 579 |
| S573-AS579-M52 | ACGGCUUGAAUGUUAAGAAAGCAGCCGAAAGGCUGC | 573 | UUUCUUAACAUUCAAGCCGUGG | 579 |
| S573-AS579-M53 | ACGGCUUGAAUGUUAAGAAAGCAGCCGAAAGGCUGC | 573 | UUUCUUAACAUUCAAGCCGUGG | 579 |
| S573-AS579-M54 | ACGGCUUGAAUGUUAAGAAAGCAGCCGAAAGGCUGC | 573 | UUUCUUAACAUUCAAGCCGUGG | 579 |
| S573-AS579-M55 | ACGGCUUGAAUGUUAAGAAAGCAGCCGAAAGGCUGC | 573 | UUUCUUAACAUUCAAGCCGUGG | 579 |
| S583-AS595-M56 | UCGAGAUGAUCUAACAAUUAGCAGCCGAAAGGCUGC | 583 | UAAUUGUUAGAUCAUCUCGAGG | 595 |
| S583-AS595-M58 | UCGAGAUGAUCUAACAAUUAGCAGCCGAAAGGCUGC | 583 | UAAUUGUUAGAUCAUCUCGAGG | 595 |
| S583-AS595-M50 | UCGAGAUGAUCUAACAAUUAGCAGCCGAAAGGCUGC | 583 | UAAUUGUUAGAUCAUCUCGAGG | 595 |
| S583-AS595-M51 | UCGAGAUGAUCUAACAAUUAGCAGCCGAAAGGCUGC | 583 | UAAUUGUUAGAUCAUCUCGAGG | 595 |
| S583-AS595-M52 | UCGAGAUGAUCUAACAAUUAGCAGCCGAAAGGCUGC | 583 | UAAUUGUUAGAUCAUCUCGAGG | 595 |

TABLE 4-continued

GYS2 RNAi oligonucleotides

| App Name | Sense Sequence | S SEQ ID NO | Antisense Sequence | AS SEQ ID NO |
|---|---|---|---|---|
| S583-AS595-M53 | UCGAGAUGAUCUAACAAUUAGCAGCCGAAAGGCUGC | 583 | UAAUUGUUAGAUCAUCUCGAGG | 595 |
| S583-AS595-M54 | UCGAGAUGAUCUAACAAUUAGCAGCCGAAAGGCUGC | 583 | UAAUUGUUAGAUCAUCUCGAGG | 595 |
| S583-AS595-M55 | UCGAGAUGAUCUAACAAUUAGCAGCCGAAAGGCUGC | 583 | UAAUUGUUAGAUCAUCUCGAGG | 595 |
| S583-AS595-M59 | UCGAGAUGAUCUAACAAUUAGCAGCCGAAAGGCUGC | 583 | UAAUUGUUAGAUCAUCUCGAGG | 595 |
| S583-AS595-M60 | UCGAGAUGAUCUAACAAUUAGCAGCCGAAAGGCUGC | 583 | UAAUUGUUAGAUCAUCUCGAGG | 595 |
| S583-AS595-M61 | UCGAGAUGAUCUAACAAUUAGCAGCCGAAAGGCUGC | 583 | UAAUUGUUAGAUCAUCUCGAGG | 595 |
| S583-AS595-M62 | UCGAGAUGAUCUAACAAUUAGCAGCCGAAAGGCUGC | 583 | UAAUUGUUAGAUCAUCUCGAGG | 595 |
| S583-AS595-M63 | UCGAGAUGAUCUAACAAUUAGCAGCCGAAAGGCUGC | 583 | UAAUUGUUAGAUCAUCUCGAGG | 595 |
| S583-AS595-M64 | UCGAGAUGAUCUAACAAUUAGCAGCCGAAAGGCUGC | 583 | UAAUUGUUAGAUCAUCUCGAGG | 595 |
| S583-AS595-M65 | UCGAGAUGAUCUAACAAUUAGCAGCCGAAAGGCUGC | 583 | UAAUUGUUAGAUCAUCUCGAGG | 595 |
| S583-AS595-M66 | UCGAGAUGAUCUAACAAUUAGCAGCCGAAAGGCUGC | 583 | UAAUUGUUAGAUCAUCUCGAGG | 595 |
| S574-AS580-M56 | AGUGUUUUUAAAAUGGUGAAGCAGCCGAAAGGCUGC | 574 | UUCACCAUUUUAAAAACACUGG | 580 |
| S574-AS580-M58 | AGUGUUUUUAAAAUGGUGAAGCAGCCGAAAGGCUGC | 574 | UUCACCAUUUUAAAAACACUGG | 580 |
| S574-AS580-M50 | AGUGUUUUUAAAAUGGUGAAGCAGCCGAAAGGCUGC | 574 | UUCACCAUUUUAAAAACACUGG | 580 |
| S574-AS580-M51 | AGUGUUUUUAAAAUGGUGAAGCAGCCGAAAGGCUGC | 574 | UUCACCAUUUUAAAAACACUGG | 580 |
| S574-AS580-M52 | AGUGUUUUUAAAAUGGUGAAGCAGCCGAAAGGCUGC | 574 | UUCACCAUUUUAAAAACACUGG | 580 |
| S574-AS580-M53 | AGUGUUUUUAAAAUGGUGAAGCAGCCGAAAGGCUGC | 574 | UUCACCAUUUUAAAAACACUGG | 580 |
| S574-AS580-M54 | AGUGUUUUUAAAAUGGUGAAGCAGCCGAAAGGCUGC | 574 | UUCACCAUUUUAAAAACACUGG | 580 |
| S574-AS580-M55 | AGUGUUUUUAAAAUGGUGAAGCAGCCGAAAGGCUGC | 574 | UUCACCAUUUUAAAAACACUGG | 580 |
| S612-AS620-M5 | UGGGAGGUAUGAGUUUUCAAGCAGCCGAAAGGCUGC | 612 | UUGAAAACUCAUACCUCCCAGG | 620 |
| S613-AS621-M5 | AGGAAAAGUUUGGAAAAAAGCAGCCGAAAGGCUGC | 613 | UUUUUUUCCAAACUUUUCCUGG | 621 |
| S614-AS622-M5 | UGGUCAAUCUUCAUAGAUGAGCAGCCGAAAGGCUGC | 614 | UCAUCUAUGAAGAUUGACAGG | 622 |
| S615-AS623-M5 | GGUUUCUGAAAUAACAGCAAGCAGCCGAAAGGCUGC | 615 | UUGCUGUUAUUUCAGAAACCGG | 623 |
| S572-AS578-M5 | CUGAAAUAACAGCAAUAGAAGCAGCCGAAAGGCUGC | 572 | UUCUAUUGCUGUUAUUUCAGGG | 578 |
| S616-AS624-M5 | GUGAAUAUAAGAACUGAAUUGCAGCCGAAAGGCUGC | 616 | AAUUCAGUUCUUAUAUUCACGG | 624 |

TABLE 4-continued

GYS2 RNAi oligonucleotides

| App Name | Sense Sequence | S SEQ ID NO | Antisense Sequence | AS SEQ ID NO |
|---|---|---|---|---|
| S617-AS625-M5 | AUUGAGUGAAUGACAAUUUUGCAGCCGAAAGGCUGC | 617 | AAAAUUGUCAUUCACUCAAUGG | 625 |
| S618-AS626-M5 | AAUGACAAUUUUGUAAUUUAGCAGCCGAAAGGCUGC | 618 | UAAAUUACAAAAUUGUCAUUGG | 626 |
| S585-AS597-M5 | AGAAUUGAUGUUGUAAUUAAGCAGCCGAAAGGCUGC | 585 | UUAAUUACAACAUCAAUUCUGG | 597 |
| S619-AS627-M5 | GAAUUGAUGUUGUAAUUAAUGCAGCGAAAGGCUGC | 619 | AUUAAUUACAACAUCAAUUCGG | 627 |
| S573-AS579-M5 | ACGGCUUGAAUGUUAAGAAAGCAGCCGAAAGGCUGC | 573 | UUUCUUAACAUUCAAGCCGUGG | 579 |
| S582-AS594-M5 | UGCAUGAGUUUCAAAAUCUAGCAGCCGAAAGGCUGC | 582 | UAGAUUUUGAAACUCAUGCAGG | 594 |
| S583-AS595-M5 | UCGAGAUGAUCUAACAAUUAGCAGCCGAAAGGCUGC | 583 | UAAUUGUUAGAUCAUCUCGAGG | 595 |
| S584-AS596-M5 | AGACUAAUUAUUUAAAAUAAGCAGCCGAAAGGCUGC | 584 | UUAUUUUAAAUAAUUAGUCUGG | 596 |

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide for reducing expression of GYS2, the oligonucleotide comprising an antisense strand of 15 to 30 nucleotides in length and a sense strand of 36 to 40 nucleotides in length, wherein the sense strand forms a duplex region with the antisense strand, and wherein:

the antisense strand has a region of complementarity to a target sequence of GYS2 as set forth in any one of SEQ ID NOs: 599-608, wherein the region of complementarity is at least 15 contiguous nucleotides in length; and the sense strand comprises a sequence as set forth in any one of SEQ ID NOs: 385-416, 569-574, 581-585, and 612-619.

2. The oligonucleotide of claim 1, wherein the antisense strand comprises a sequence as set forth in any one of SEQ ID NOs: 417-466, 575-580, 586-598, and 620-627.

3. The oligonucleotide of claim 1, wherein the sense strand comprises at its 3'-end a stem-loop set forth as: $S_1$-L-$S_2$, wherein $S_1$ is complementary to $S_2$, and wherein L forms a loop between $S_1$ and $S_2$ of 3 to 5 nucleotides in length.

4. The oligonucleotide of claim 1, wherein the oligonucleotide comprises a 3'-overhang sequence of one or more nucleotides in length, wherein the 3'-overhang sequence is present on the antisense strand, the sense strand, or the antisense strand and sense strand.

5. The oligonucleotide of claim 1, wherein the oligonucleotide comprises at least one modified nucleotide and wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

6. The oligonucleotide of claim 1, wherein the oligonucleotide comprises at least one modified internucleotide linkage, wherein the at least one modified internucleotide linkage is a phosphorothioate linkage.

7. The oligonucleotide of claim 1, wherein the duplex region formed by the sense strand and the antisense strand is at least 19 nucleotides in length.

8. The oligonucleotide of claim 1, wherein the region of complementarity of the antisense strand to the target sequence of GYS2 is at least 19 contiguous nucleotides in length.

9. The oligonucleotide of claim 1, wherein the antisense strand is 21 to 27 nucleotides in length.

10. The oligonucleotide of claim 1, wherein at least one nucleotide of the oligonucleotide is conjugated to one or more targeting ligands, wherein each targeting ligand comprises a N-acetylgalactosamine (GalNAc) moiety.

11. The oligonucleotide of claim 10, wherein the GalNac moiety is a monovalent GalNAc moiety, a bivalent GalNAc moiety, a trivalent GalNAc moiety, or a tetravalent GalNAc moiety.

12. The oligonucleotide of claim 1, wherein the 4'-carbon of the sugar of the 5'-nucleotide of the antisense strand comprises a phosphate analog, and wherein the phosphate analog is oxymethylphosphonate, vinylphosphonate, or malonylphosphonate.

13. A composition comprising the oligonucleotide of claim 1 and an excipient.

14. An oligonucleotide for reducing expression of GYS2, the oligonucleotide comprising an antisense strand of 15 to 30 nucleotides in length and a sense strand of 15 to 40 nucleotides in length, wherein the sense strand forms a duplex region with the antisense strand, and wherein:
  the antisense strand has a region of complementarity to a target sequence of GYS2 as set forth in any one of SEQ ID NOs: 599-608, wherein the region of complementarity is at least 15 contiguous nucleotides in length; and
  the sense strand comprises at its 3'-end a stem-loop set forth as: $S_1$-L-$S_2$, wherein $S_1$ is complementary to $S_2$; L forms a loop between $S_1$ and $S_2$; and L is a tetraloop.

15. The oligonucleotide of claim 14, wherein the antisense strand comprises a sequence as set forth in any one of SEQ ID NOs: 417-466, 575-580, 586-598, and 620-627.

16. The oligonucleotide of claim 14, wherein the sense strand comprises a sequence as set forth in any one of SEQ ID NOs: 385-416, 569-574, 581-585, and 612-619.

17. The oligonucleotide of claim 14, wherein the duplex region formed by the sense strand and the antisense strand is at least 19 nucleotides in length.

18. The oligonucleotide of claim 14, wherein the region of complementarity of the antisense strand to the target sequence of GYS2 is at least 19 contiguous nucleotides in length.

19. The oligonucleotide of claim 14, wherein the antisense strand is 21 to 27 nucleotides in length.

20. The oligonucleotide of claim 14, wherein the oligonucleotide comprises a 3'-overhang sequence of one or more nucleotides in length, wherein the 3'-overhang sequence is present on the antisense strand, the sense strand, or the antisense strand and sense strand.

21. The oligonucleotide of claim 14, wherein the oligonucleotide comprises at least one modified nucleotide and wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

22. The oligonucleotide of claim 14, wherein the oligonucleotide comprises at least one modified internucleotide linkage, wherein the at least one modified internucleotide linkage is a phosphorothioate linkage.

23. The oligonucleotide of claim 14, wherein at least one nucleotide of the oligonucleotide is conjugated to one or more targeting ligands, wherein each targeting ligand comprises a N-acetylgalactosamine (GalNAc) moiety.

24. The oligonucleotide of claim 23, wherein the GalNac moiety is a monovalent GalNAc moiety, a bivalent GalNAc moiety, a trivalent GalNAc moiety, or a tetravalent GalNAc moiety.

25. The oligonucleotide of claim 14, wherein the 4'-carbon of the sugar of the 5'-nucleotide of the antisense strand comprises a phosphate analog, and wherein the phosphate analog is oxymethylphosphonate, vinylphosphonate, or malonylphosphonate.

26. A composition comprising the oligonucleotide of claim 14 and an excipient.

27. An oligonucleotide for reducing expression of GYS2, wherein:
  the antisense strand has a region of complementarity to a target sequence of GYS2 as set forth in any one of SEQ ID NOs: 599-608, wherein the region of complementarity is at least 15 contiguous nucleotides in length;
  the oligonucleotide comprises a 3'-overhang sequence of two nucleotides in length, wherein the 3'-overhang sequence is present on the antisense strand;
  the sense strand is 21 nucleotides in length and the antisense strand is 23 nucleotides in length, such that the sense strand and antisense strand form a duplex of 21 nucleotides in length;
  the oligonucleotide comprises at least one modified nucleotide and wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid; and
  wherein the 4'-carbon of the sugar of the 5'-nucleotide of the antisense strand comprises a phosphate analog, and wherein the phosphate analog is oxymethylphosphonate, vinylphosphonate, or malonylphosphonate.

28. The oligonucleotide of claim 27, wherein at least one nucleotide of the oligonucleotide is conjugated to one or more targeting ligands, wherein each targeting ligand comprises a N-acetylgalactosamine (GalNAc) moiety.

29. The oligonucleotide of claim 28, wherein the GalNac moiety is a monovalent GalNAc moiety, a bivalent GalNAc moiety, a trivalent GalNAc moiety, or a tetravalent GalNAc moiety.

30. The oligonucleotide of claim 27, wherein the duplex region formed by the sense strand and the antisense strand is at least 19 nucleotides in length.

31. The oligonucleotide of claim 27, wherein the region of complementarity of the antisense strand to the target sequence of GYS2 is at least 19 contiguous nucleotides in length.

32. The oligonucleotide of claim 27, wherein the oligonucleotide comprises at least one modified internucleotide linkage, wherein the at least one modified internucleotide linkage is a phosphorothioate linkage.

33. The oligonucleotide of claim 27, wherein at least one nucleotide of the oligonucleotide is conjugated to one or more targeting ligands, wherein each targeting ligand comprises a N-acetylgalactosamine (GalNAc) moiety.

34. The oligonucleotide of claim 33, wherein the GalNac moiety is a monovalent GalNAc moiety, a bivalent GalNAc moiety, a trivalent GalNAc moiety, or a tetravalent GalNAc moiety.

35. A composition comprising the oligonucleotide of claim 27 and an excipient.

* * * * *